(12) United States Patent
Ettmayer et al.

(10) Patent No.: US 8,865,703 B2
(45) Date of Patent: Oct. 21, 2014

(54) PYRIDYLTRIAZOLES

(75) Inventors: Peter Ettmayer, Ingelheim am Rhein (DE); Steffen Steurer, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/636,158

(22) PCT Filed: Mar. 25, 2011

(86) PCT No.: PCT/EP2011/054612
§ 371 (c)(1),
(2), (4) Date: Oct. 3, 2012

(87) PCT Pub. No.: WO2011/117382
PCT Pub. Date: Sep. 29, 2011

(65) Prior Publication Data
US 2013/0225562 A1    Aug. 29, 2013

(30) Foreign Application Priority Data
Mar. 26, 2010    (EP) .................................. 10158042

(51) Int. Cl.
| C07D 401/00 | (2006.01) |
| A61K 31/55 | (2006.01) |
| C07D 405/14 | (2006.01) |
| A61K 31/496 | (2006.01) |
| A61K 45/06 | (2006.01) |
| C07D 409/14 | (2006.01) |
| C07D 401/14 | (2006.01) |
| A61K 31/551 | (2006.01) |

(52) U.S. Cl.
CPC ............ C07D 401/14 (2013.01); C07D 405/14 (2013.01); A61K 31/496 (2013.01); A61K 45/06 (2013.01); C07D 409/14 (2013.01); A61K 31/551 (2013.01)
USPC .......................................... 514/218; 546/256

(58) Field of Classification Search
CPC ... C07D 401/14; C07D 405/14; C07D 409/14
See application file for complete search history.

(56) References Cited

U.S. PATENT DOCUMENTS

| 4,218,457 A | 8/1980 | Atsumi et al. |
| 5,990,133 A | 11/1999 | Gaster et al. |
| 6,492,403 B1 | 12/2002 | Illig et al. |
| 7,166,628 B2 | 1/2007 | Cogan et al. |
| 7,214,802 B2 | 5/2007 | Cogan et al. |
| 7,485,657 B2 | 2/2009 | Cogan et al. |
| 7,511,042 B2 | 3/2009 | Cogan et al. |
| 7,514,458 B2 | 4/2009 | Cogan et al. |
| 7,531,560 B2 | 5/2009 | Cogan et al. |
| 7,569,568 B2 | 8/2009 | Cogan et al. |
| 7,858,804 B2 | 12/2010 | Frutos et al. |
| 8,198,308 B2 | 6/2012 | Steurer et al. |
| 2004/0102492 A1 | 5/2004 | Cogan et al. |
| 2005/0153972 A1 | 7/2005 | Cogan et al. |
| 2005/0256113 A1 | 11/2005 | Cogan et al. |
| 2006/0079519 A1 | 4/2006 | Cogan et al. |
| 2006/0100204 A1 | 5/2006 | Cogan et al. |
| 2007/0032492 A1 | 2/2007 | Cogan et al. |
| 2007/0142371 A1 | 6/2007 | Cogan et al. |
| 2007/0155746 A1 | 7/2007 | Lang et al. |
| 2008/0009497 A1 | 1/2008 | Wittman et al. |
| 2008/0027070 A1 | 1/2008 | Noronha et al. |
| 2008/0045489 A1 | 2/2008 | Chao et al. |
| 2008/0132459 A1 | 6/2008 | Moradei et al. |
| 2008/0182837 A1 | 7/2008 | Steurer et al. |
| 2009/0127815 A1 | 5/2009 | Tani et al. |
| 2009/0239838 A1 | 9/2009 | Wittman et al. |
| 2010/0240657 A1 | 9/2010 | Sapountzis et al. |
| 2011/0059938 A1 | 3/2011 | Steurer et al. |
| 2011/0124623 A1 | 5/2011 | Wittman et al. |
| 2011/0183952 A1 | 7/2011 | Sapountzis et al. |
| 2011/0312939 A1 | 12/2011 | Steurer et al. |
| 2012/0046270 A1 | 2/2012 | Ettmayer et al. |
| 2012/0094975 A1 | 4/2012 | Mantoulidis et al. |
| 2013/0190286 A1 | 7/2013 | Steurer et al. |

FOREIGN PATENT DOCUMENTS

| EP | 1364949 A1 | 11/2003 |
| FR | 2401916 A1 | 3/1979 |

(Continued)

OTHER PUBLICATIONS

Caplus: Chan, et al., 2002, CAS: 138:198127.Subasinghe, N.L. et al., "Structure-based Design, Synthesis and SAR of a Novel Series of Thiopheneamidine Urokinase Plasminogen Activator Inhibitors", Bioorganice and Medicinal Chemistry Letters, 11, 2001, pp. 1379-1382.

(Continued)

*Primary Examiner* — Heidi Reese
(74) *Attorney, Agent, or Firm* — Michael P. Morris; Alan R. Stempel

(57) ABSTRACT

The present invention encompasses compounds of general formula (1) wherein the groups $R^0$ to $R^3$ and L are defined as in claim 1, which are suitable for the treatment of diseases characterized by excessive or abnormal cell proliferation, pharmaceutical preparations which contain such compounds and their use as medicaments.

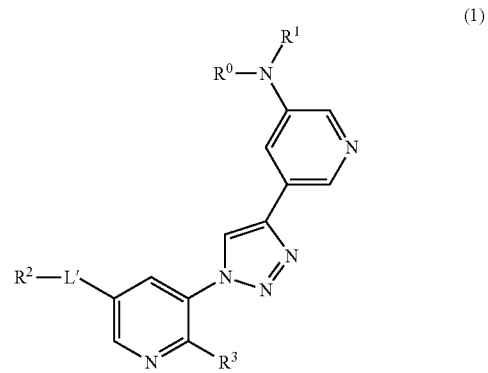

(1)

15 Claims, No Drawings

(56) References Cited

FOREIGN PATENT DOCUMENTS

| | | |
|---|---|---|
| JP | 03174153 A | 7/1991 |
| WO | 9703967 A1 | 2/1997 |
| WO | 0075120 A1 | 12/2000 |
| WO | 0162737 A2 | 8/2001 |
| WO | 03037274 A2 | 5/2003 |
| WO | 03051358 A1 | 6/2003 |
| WO | 03059886 A1 | 7/2003 |
| WO | 2004050642 A1 | 6/2004 |
| WO | 2005023761 A2 | 3/2005 |
| WO | 2005040152 A1 | 5/2005 |
| WO | 2005056535 A1 | 6/2005 |
| WO | 2005090333 A1 | 9/2005 |
| WO | 2005115991 A1 | 12/2005 |
| WO | 2006053227 A2 | 5/2006 |
| WO | 2007056016 A2 | 5/2007 |
| WO | 2007075896 A2 | 7/2007 |
| WO | 2007076474 A1 | 7/2007 |
| WO | 2007121390 A1 | 10/2007 |
| WO | 2007132010 A1 | 11/2007 |
| WO | 2008003770 A1 | 1/2008 |
| WO | 2008021388 A1 | 2/2008 |
| WO | 2008079909 A1 | 7/2008 |
| WO | 2008089034 A2 | 7/2008 |
| WO | 2008106692 A1 | 9/2008 |
| WO | 2009003998 A2 | 1/2009 |
| WO | 2009003999 A2 | 1/2009 |
| WO | 2009012283 A1 | 1/2009 |
| WO | 2010010154 A1 | 1/2010 |
| WO | 2010026262 A1 | 3/2010 |
| WO | 2010034838 A2 | 4/2010 |
| WO | 2010094695 A1 | 8/2010 |
| WO | 2011117381 A1 | 9/2011 |
| WO | 2011117382 A1 | 9/2011 |
| WO | 2012085127 A1 | 6/2012 |
| WO | 2012101238 A1 | 8/2012 |
| WO | 2012104388 A1 | 8/2012 |

OTHER PUBLICATIONS

International Search Report for PCT/EP2011/054612 mailed Jul. 28, 2011.

Patani, G.A. et al., "Bioisosterism: A Rational Approach in Drug Design", Chem Rev, 96, 1996, pp. 3147-3176.

Sparreboom, A. et al., "The Use of Oral Cytotoxic and Cytostatic Drugs in Cancer Treatment." European Journal of Cancer 38, 2002, pp. 18-22.

Williams, D.A. et al., Foye's Principles of Medicinal Chemistry, Fifth Edition, 2002, pp. 59-63.

PYRIDYLTRIAZOLES

The present invention relates to new pyridyltriazoles of general formula (1)

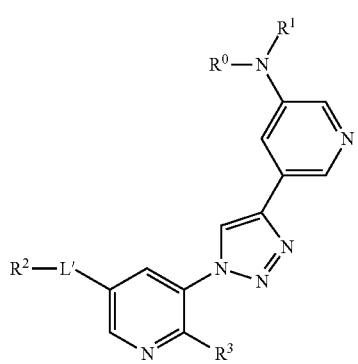

wherein the groups $R^0$ to $R^3$ and L' have the meanings given in the claims and specification, pharmaceutical preparations which contain compounds of this kind and their use as medicaments. The compounds according to the invention exhibit an inhibitory activity on the mutated serine/threonine kinase B-Raf V600E.

BACKGROUND TO THE INVENTION

Phenyl- and pyridyl-substituted five-ringed heteroaryls for inhibiting cytokines are described in WO 2007/075896, pyridyl-substituted triazoles with the same activity are described in WO 2008/021388.

The aim of the present invention is to indicate new pyridyltriazoles which may be used for the prevention and/or treatment of diseases characterised by excessive or abnormal cell proliferation. The pyridyltriazoles according to the invention are distinguished by their great inhibitory effect on B-Raf V600E and their high potency against tumour cells, e.g. melanoma cells, which is achieved by the inhibition of B-Raf V600E. In addition to the inhibitory effect and cell potency the compounds additionally have good pharmacokinetic properties and good solubility. As a result of this overall profile, the compounds according to the invention are suitable for the development of a drug.

The RAS-RAF-MAPK (mitogen-activated protein kinase) signaling pathway plays a critical role in transmitting proliferation signals generated by the cell surface receptors and cytoplasmic signaling elements to the nucleus. Constitutive activation of this pathway is involved in malignant transformation by several oncogenes. Activating mutations in RAS occur in approximately 15% of cancers, and recent data has shown that B-RAF is mutated in about 7% of cancers (Wellbrock et al., Nature Rev. Mol. Cell Biol. 2004, 5:875-885), identifying it as another important oncogene in this pathway. In mammals, the RAF family of serine/threonine kinases comprises three members: A-RAF, B-RAF and C-RAF. However, activating mutations have so far been only identified in B-RAF underlining the importance of this isoform. It is believed that B-RAF is the main isoform that couples RAS to MEK, and that C-RAF and A-RAF signal to ERK only to fine-tune cellular responses (Wellbrock et al., Nature Rev. Mol. Cell Biol. 2004, 5:875-885). The most common cancer mutation in B-RAF results in a valine to glutamic acid exchange at position 600 of the protein (V600E), which dramatically enhances B-RAF activity, presumably because its negative charge mimics activation loop phosphorylation (Wan et al., Cell 2004, 116: 855-867). The highest incidence of B-RAF V600 mutations occurs in malignant melanoma (38%), thyroid cancer (38%), colorectal cancer (10%), bilary tract cancer (12%) and ovarian cancer (12%), but they also occur at a low frequency in a wide variety of other cancers (frequencies of mutations according to COSMIC (*Catalogue Of Somatic Mutations In Cancer; Wellcome Trust Sanger Institute*) release v49, 29 Sep. 2010). Literature supported the hypothesis that B-RAF$^{V600E}$ mutated tumour cells seem to rely heavily on the continued activation of this pathway—a phenomenon termed "oncogene addiction"—whereas normal B-RAF$^{wt}$ cells use a broader range of signals. This provides an Achilles' heel that can be exploited therapeutically by treating patients with somatically mutated B-RAF$^{V600E}$ using orally available B-RAF inhibitors.

The key role of B-RAF$^{V600E}$ in aberrant ERK signaling and consequently oncogenesis has been demonstrated in several independent experimental approaches such as overexpression of oncogenic/mutated B-RAF in vitro and in vivo (Wan et al., Cell 2004, 116: 855-867; Wellbrock et al., Cancer Res. 2004, 64: 2338-2342), siRNA knock-down in vitro (Karasarides et al., Oncogene 2004, 23: 6292-6298) or in inducible short-hairpin RNA xenograft models where gain-of-function B-RAF signaling was found to be strongly associated with in vivo tumorigenicity (Hoeflich et al., Cancer Res. 2006, 66: 999-1006).

Treatment of B-RAF$^{V600E}$ mutated melanoma or colon carcinoma cells induces a B-RAF inhibition phenotype (e.g. reduction of phospho-MEK and phospho-ERK levels, reduction of cyclin D expression and induction of p27 expression). Consequently, these cells are locked in the G1-phase of the cell cycle and do not proliferate.

DETAILED DESCRIPTION OF THE INVENTION

It has now been found that, surprisingly, compounds of general formula (1) wherein the groups $R^0$ to $R^3$ and L' have the meanings given hereinafter act as inhibitors of specific signal enzymes which are involved in controlling cell proliferation. Thus, the compounds according to the invention may be used for example for the treatment of diseases connected with the activity of these signal enzymes and characterised by excessive or abnormal cell proliferation.

The present invention therefore relates to compounds of general formula (1)

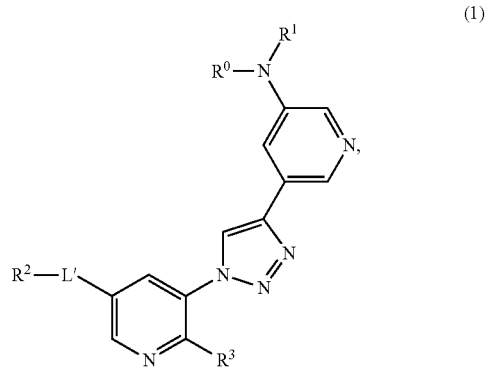

wherein (A0)

R⁰ is selected from among hydrogen and $C_{1-6}$alkyl and $R^1$ is hydrogen or a group optionally substituted by one or more, identical or different $R^{b1}$ and/or $R^{c1}$, selected from among $C_{1-6}$alkyl, $C_{2-6}$alkenyl, $C_{1-6}$alkynyl, $C_{1-6}$haloalkyl, $C_{3-6}$cycloalkyl, $C_{4-6}$-cycloalkenyl and 3-11 membered heterocyclyl;

each $R^{b1}$ is selected independently of one another from among —$OR^{c1}$, —$SR^{c1}$, —$NR^{c1}R^{c1}$, halogen, —C(O)$R^{c1}$, —C(O)O$R^{c1}$, —C(O)N$R^{c1}R^{c1}$, —CN, —NHC(O)$R^{c1}$ and —NHC(O)O$R^{c1}$;

each $R^{c1}$ independently of one another denotes hydrogen or a group selected from among $C_{1-6}$alkyl, $C_{2-6}$alkenyl, $C_{2-6}$alkinyl, $C_{3-6}$cycloalkyl, $C_{4-6}$cycloalkenyl, $C_{1-6}$alkyl-O—$C_{1-6}$alkyl, $(C_{1-4}$alkyl)HN—$C_{1-6}$alkyl, $(C_{1-4}$alkyl)$_2$N—$C_{1-6}$alkyl, $C_{1-6}$haloalkyl, 4-16 membered heterocyclylalkyl and 3-11 membered heterocyclyl, wherein heterocyclyl in the above-mentioned groups may optionally be substituted by one or more identical or different $C_{1-6}$alkyl;

or the group —$NR^0R^1$ together denotes a 3-11-membered, nitrogen-containing heterocyclyl, which is optionally substituted by one or more identical or different substituents $R^{a2}$ and/or $R^{b2}$;

each $R^{a2}$ independently denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$-cycloalkenyl and 3-11 membered heterocyclyl;

each $R^{b2}$ is independently selected from among —$OR^{c2}$, —$SR^{c2}$, —$NR^{c2}R^{c2}$, halogen, —C(O)$R^{c2}$, —C(O)O$R^{c2}$, —C(O)N$R^{c2}R^{c2}$, —CN, —NHC(O)$R^{c2}$ and —NHC(O)O$R^{c2}$;

each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-11 membered heterocyclyl, while this heterocyclyl may optionally be substituted by one or more identical or different substituents selected from among halogen, $C_{1-6}$alkyl and —C(O)—$C_{1-6}$alkyl;

(B0)

$R^2$-L'- is selected from among

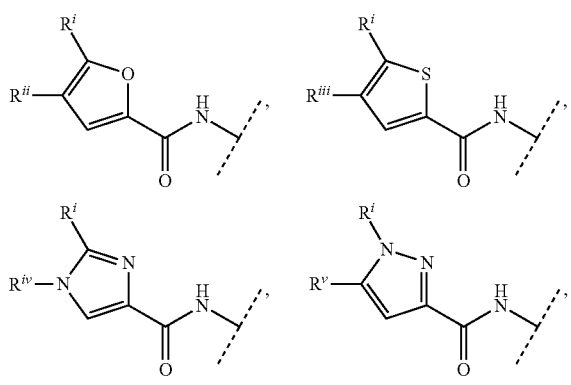

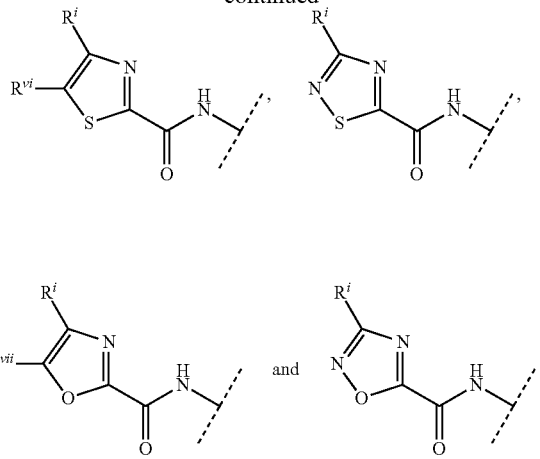

$R^I$ is selected from among tert-butyl, iso-propyl, cyclopropyl, —$CF_3$, —$CF_2(CH_3)$, —$CF(CH_3)_2$, —$CH_2CF_3$, —$CHF_2$, —$CH_2F$ and —$C(CH_3)_2CN$;

$R^{II}$, $R^{III}$ and $R^V$ are selected independently of one another from among hydrogen, methyl, ethyl, n-propyl, iso-propyl, cyclopropyl, $R^iR^{ii}N$—$CH_2$— and $R^{iii}O$—$CH_2$—;

$R^i$ is selected from among hydrogen and $C_{1-6}$alkyl;

$R^{ii}$ is selected from among $C_{1-6}$alkyl, $(C_{1-6}$alkyl)$_2$N—$C_{1-6}$alkyl-, $(C_{1-6}$alkyl)NH—$C_{1-6}$alkyl-, $C_{3-6}$cycloalkyl and 3-7 membered heterocyclyl, wherein this 3-7 membered heterocyclyl may optionally be substituted by $C_{1-6}$alkyl;

or the group —$NR^iR^{ii}$ together denotes a 3-7 membered, nitrogen-containing heterocyclyl, which may optionally be substituted by one or more identical or different $C_{1-6}$alkyl;

$R^{iii}$ is selected from among hydrogen, $C_{1-6}$alkyl, $C_{3-6}$cycloalkyl and $C_{1-6}$haloalkyl;

$R^{IV}$ is selected from among hydrogen, methyl, ethyl and n-propyl;

$R^{VI}$ and $R^{VII}$ are selected independently of one another from among hydrogen, methyl, ethyl, n-propyl, iso-propyl and cyclopropyl;

(C0)

$R^3$ is selected from among $C_{1-4}$alkyl, $C_{1-4}$haloalkyl-O, —$NH_2$, and —NH($C_{1-4}$alkyl);

wherein the compounds (1) may optionally also be present in the form of the tautomers, racemates, enantiomers, diastereomers and the mixtures thereof or as the respective salts of all the above-mentioned forms.

In one aspect (C1) the invention relates to compounds (1), wherein $R^3$ is selected from among methyl, ethyl, iso-propyl, —$CF_3$, chlorine, bromine, fluorine, methoxy and —$OCF_3$.

In another aspect (C2) the invention relates to compounds (1), wherein $R^3$ denotes methyl.

In another aspect (A1) the invention relates to compounds (1), wherein

R⁰ is selected from among hydrogen and $C_{1-6}$alkyl and $R^1$ is hydrogen or a group optionally substituted by one or more, identical or different $R^{b1}$ and/or $R^{c1}$, selected from among $C_{1-6}$alkyl, $C_{2-6}$alkenyl, $C_{2-6}$alkynyl, $C_{3-6}$cycloalkyl and 3-11 membered heterocyclyl;

each $R^{b1}$ is selected independently of one another from among —$OR^{c1}$, —$SR^{c1}$, —$NR^{c1}R^{c1}$, halogen, —C(O)$R^{c1}$, —C(O)O$R^{c1}$, —C(O)N$R^{c1}R^{c1}$, —NHC(O)$R^{c1}$ and —NHC(O)O$R^{c1}$;

each $R^{c1}$ independently of one another denotes hydrogen or a group selected from among $C_{1-6}$alkyl and 3-11 membered heterocyclyl, while this 3-11 membered heterocyclyl may optionally be substituted by one or more identical or different $C_{1-6}$alkyl;

or the group —$NR^0R^1$ together denotes a 3-11 membered, nitrogen-containing heterocyclyl, which is optionally substituted by one or more, identical or different substituents $R^{a2}$ and/or $R^{b2}$;

each $R^{a2}$ independently of one another is a group optionally substituted by one or more identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl and 3-11 membered heterocyclyl;

each $R^{b2}$ is selected independently of one another from among —$OR^{c2}$, —$SR^{c2}$, —$NR^{c2}R^{c2}$, halogen, —$C(O)R^{c2}$, —$C(O)OR^{c2}$, —$C(O)NR^{c2}R^{c2}$, —CN, —$NHC(O)R^{c2}$ and —$NHC(O)OR^{c2}$;

each $R^{c2}$ independently of one another denotes hydrogen or a group selected from among $C_{1-6}$alkyl, $C_{3-6}$cycloalkyl and 3-11 membered heterocyclyl;

In another aspect (A2) the invention relates to compounds (1), wherein $R^0$ is selected from among hydrogen and methyl and $R^1$ is hydrogen or a group optionally substituted by one or more, identical or different $R^{b1}$ and/or $R^{c1}$, selected from among methyl, ethyl, iso-propyl, n-propyl, tert-butyl, cyclopropyl, cyclobutyl, cyclopentyl, cyclohexyl and 5-7 membered heterocyclyl;

each $R^{b1}$ is independently selected from among —$OR^{c1}$, —$NR^{c1}R^{c1}$ halogen and —$C(O)OR^{c1}$;

each $R^{c1}$ independently of one another denotes hydrogen or a group, selected from among methyl, ethyl, iso-propyl and 5-7 membered heterocyclyl, wherein this 5-7 membered heterocyclyl may optionally be substituted by one or more identical or different substituents, selected from among methyl, ethyl or iso-propyl.

In another aspect (A3) the invention relates to compounds (1), wherein $R^0$ is selected from among hydrogen and methyl and $R^1$ is hydrogen or a group optionally substituted by one or more, identical or different $R^{b1}$ and/or $R^{c1}$, selected from among methyl, ethyl, iso-propyl, tert-butyl, cyclopropyl, cyclobutyl, cyclopentyl, tetrahydrofuryl, tetrahydropyranyl, pyrrolidinyl and piperidinyl;

each $R^{b1}$ is independently selected from among —$OR^{c1}$, —$NR^{c1}R^{c1}$, halogen and —$C(O)OR^{c1}$;

each $R^{c1}$ independently of one another denotes hydrogen or a group selected from among methyl, ethyl, iso-propyl, tetrahydrofuryl, tetrahydropyranyl, pyrrolidinyl, morpholinyl, homomorpholinyl, piperazinyl, homopiperazinyl and piperidinyl, wherein piperazinyl and piperidinyl may optionally be substituted by methyl, ethyl or iso-propyl.

In another aspect (A4) the invention relates to compounds (1), wherein

—$NR^0R^1$ is selected from among

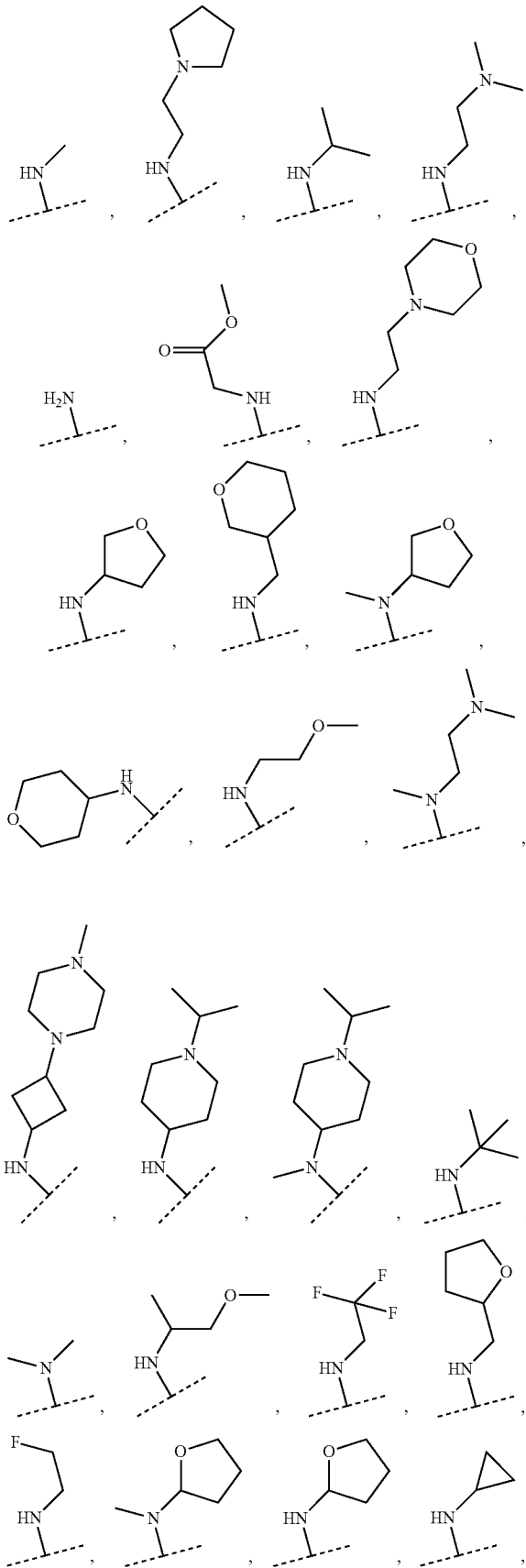

-continued

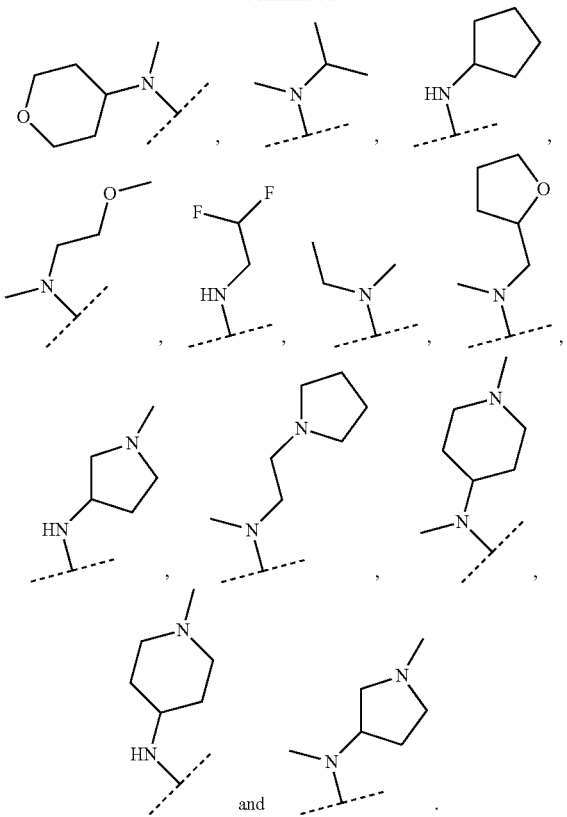

In another aspect (A5) the invention relates to compounds (1), wherein
the group —NR⁰R¹ together denotes a 3-11 membered, nitrogen-containing heterocyclyl which is optionally be substituted by one or more identical or different substituents $R^{a2}$ and/or $R^{b2}$;
- each $R^{a2}$ independently of one another denotes a group optionally substituted by one or more identical or different $R^{b2}$ and/or $R^{c2}$, selected from among iso-propyl, methyl, ethyl, tert-butyl, n-propyl, n-butyl, iso-butyl, 3-pentyl, allyl, cyclopropyl, cyclobutyl, cyclopentyl, cyclohexyl and 3-11 membered heterocyclyl;
- each $R^{b2}$ is selected independently of one another from among —OR$^{c2}$, —NR$^{c2}$R$^{c2}$, halogen, —C(O)OR$^{c2}$, —C(O)NR$^{c2}$R$^{c2}$ and —CN;
- each $R^{c2}$ independently of one another denotes hydrogen or a group selected from among methyl, ethyl, iso-propyl, tert-butyl, cyclopropyl, cyclobutyl, cyclopentyl, cyclohexyl and 3-11 membered heterocyclyl.

In another aspect (A6) the invention relates to compounds (1), wherein
the group —NR⁰R¹ together denotes a nitrogen-containing heterocyclyl, selected from among piperazinyl, homopiperazinyl, 2,7-diaza-spiro[4.4]nonyl, 3,9-diaza-spiro[5.5]undecyl, piperidinyl, morpholinyl, homomorpholinyl, azetidinyl, pyrrolidinyl and 2,5-diaza-bicyclo[2.2.1]heptyl, which is optionally substituted by one or more identical or different substituents $R^{a2}$ and/or $R^{b2}$;
- each $R^{a2}$ independently denotes a group optionally substituted by one or more, identical or different $R^{b2}$ and/or $R^{c2}$, selected from among iso-propyl, methyl, ethyl, tert-butyl, n-propyl, n-butyl, iso-butyl, 3-pentyl, allyl, cyclopropyl, cyclobutyl, cyclopentyl, morpholinyl, piperidinyl and piperazinyl;
- each $R^{b2}$ is independently selected from among —OR$^{c2}$, —NR$^{c2}$R$^{c2}$, halogen, —C(O)OR$^{c2}$, —C(O)NR$^{c2}$R$^{c2}$ and —CN;
- each $R^{c2}$ independently denotes hydrogen or a group selected from among methyl, ethyl, iso-propyl, tert-butyl, cyclopropyl, cyclobutyl, cyclopentyl, cyclohexyl, tetrahydrofuryl and morpholinyl.

In another aspect (A7) the invention relates to compounds (1), wherein
the group —NR⁰R¹ together denotes a piperazinyl or homopiperazinyl, which is substituted by a substituent selected from among methyl, ethyl, n-propyl, iso-propyl, tert-butyl, cyclopropylmethyl, methoxypropyl, ethoxyethyl, iso-propyloxyethyl and cyclopropyl.

In another aspect (A8) the invention relates to compounds (1), wherein
the group —NR⁰R¹ together denotes a piperazinyl which is substituted by a substituent selected from among methyl, ethyl, n-propyl, iso-propyl, tert-butyl, cyclopropylmethyl, methoxypropyl, ethoxyethyl, iso-propyloxyethyl and cyclopropyl.

In another aspect (A9) the invention relates to compounds (1), wherein
—NR⁰R¹ is selected from among

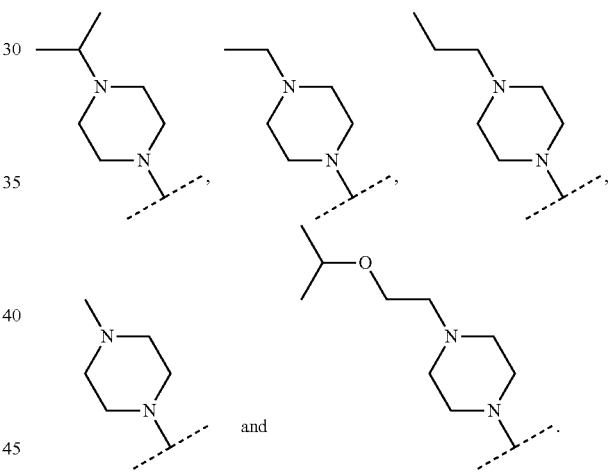

In another aspect (A10) the invention relates to compounds (1), wherein
—NR⁰R¹ is selected from among

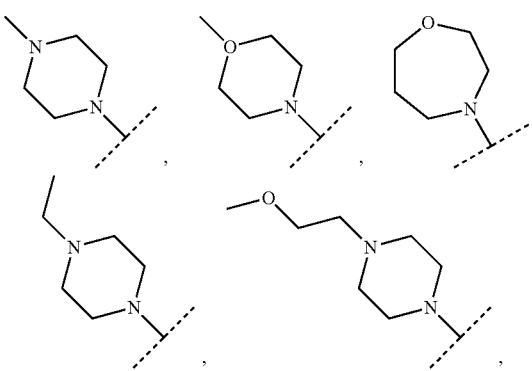

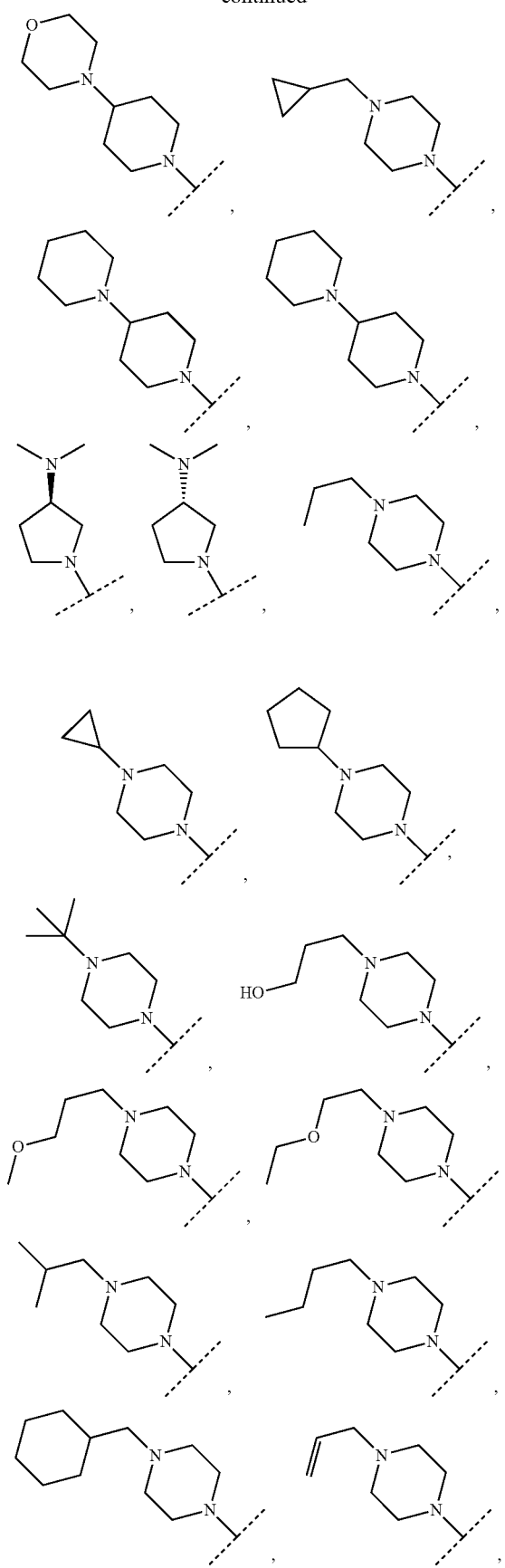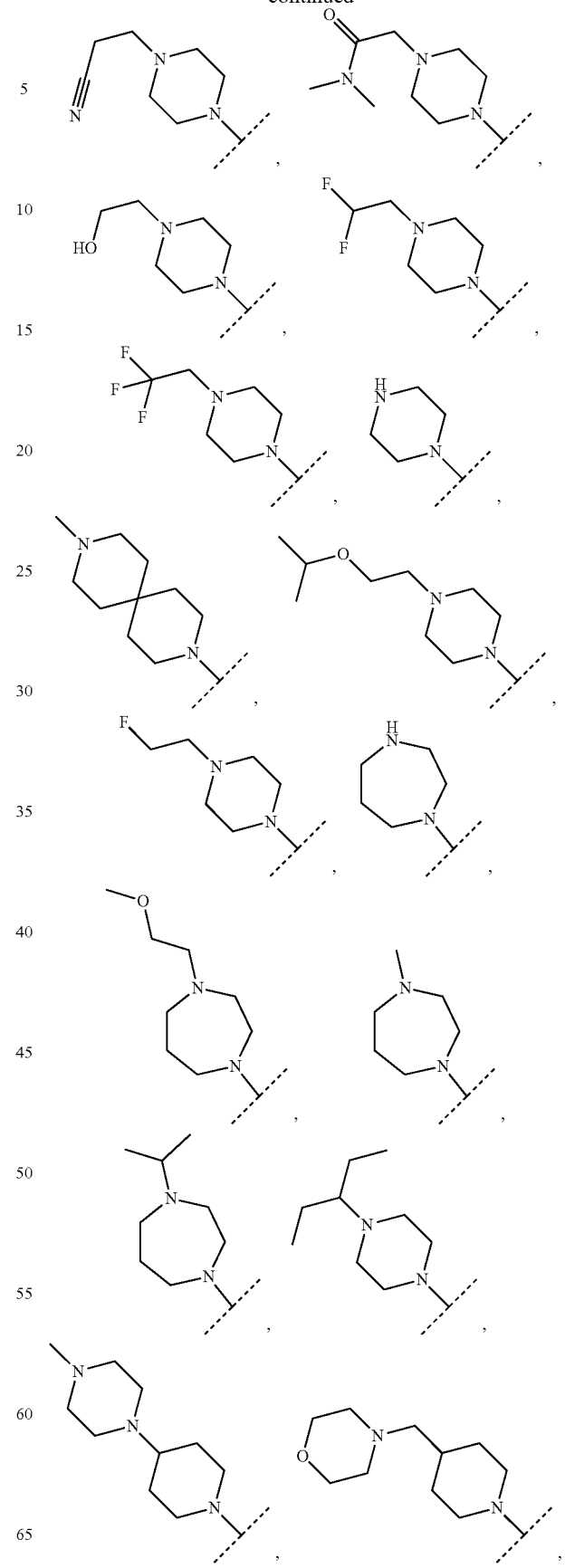

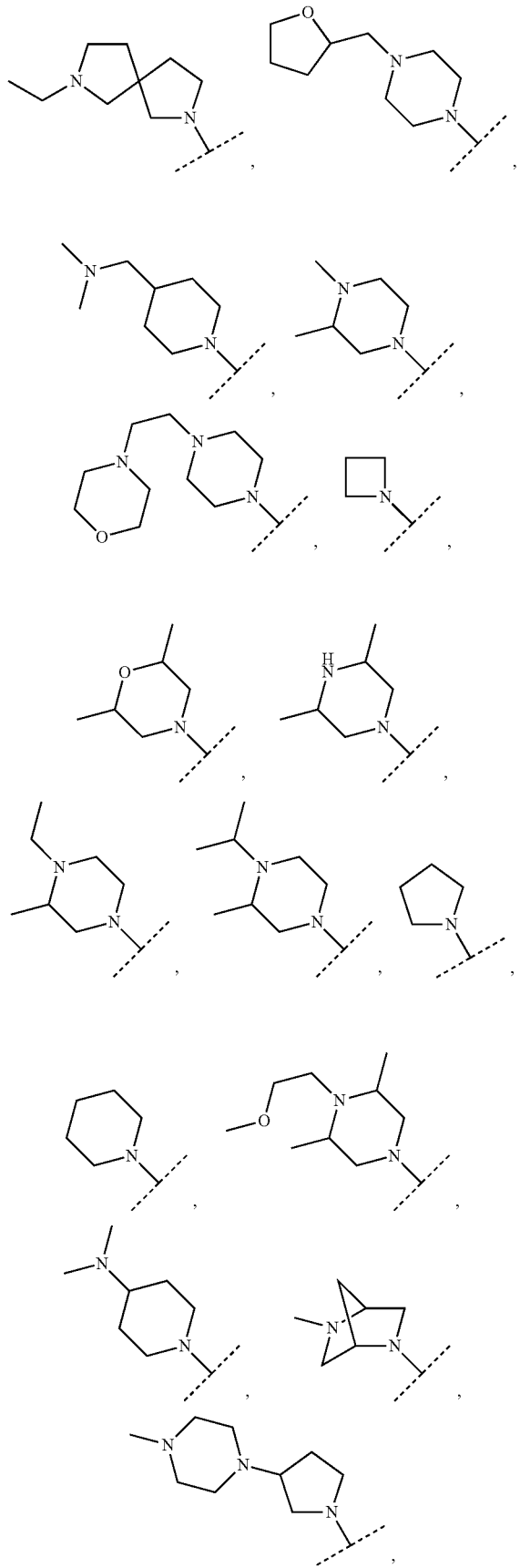
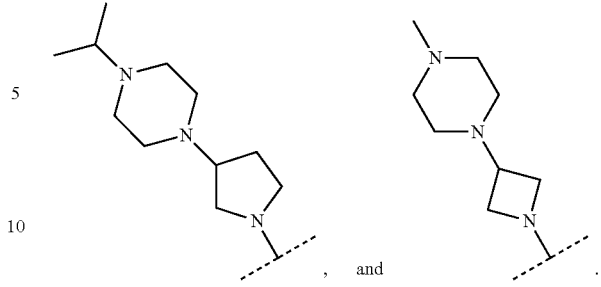
In another aspect (B1) the invention relates to compounds (1), wherein
R²-L'- is selected from among
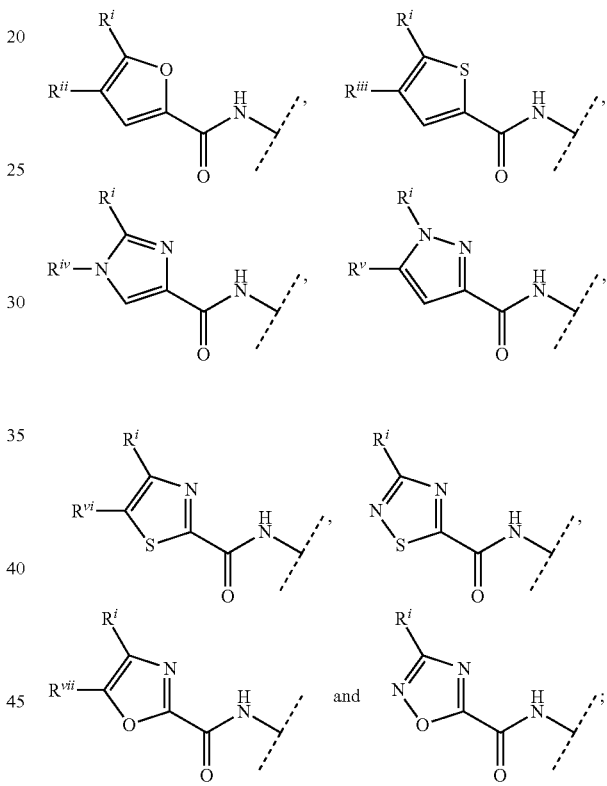
$R^I$ is selected from among tert-butyl and iso-propyl and $R^{II}, R^{III}, R^{IV}, R^V, R^{VI}$ and $R^{VII}$ are as hereinbefore defined.
In another aspect (B2) the invention relates to compounds (1), wherein
R²-L'- denotes the group
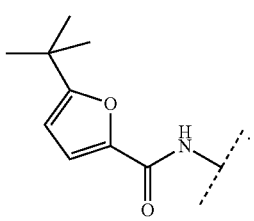

In another aspect (B3) the invention relates to compounds (1), wherein
R²-L'- denotes the group

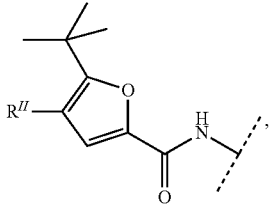

R$^{II}$ is selected from among R$^i$R$^{ii}$N—CH$_2$— and R$^{iii}$O—CH$_2$—;
R$^i$ is selected from among hydrogen and C$_{1-6}$alkyl;
R$^{ii}$ is selected from among C$_{1-6}$alkyl, (C$_{1-6}$alkyl)$_2$N—C$_{1-6}$alkyl, (C$_{1-6}$alkyl)NH—C$_{1-6}$alkyl- and 3-7 membered heterocyclyl, while this 3-7 membered heterocyclyl may optionally be substituted by one or more identical or different C$_{1-6}$alkyl;
or
the group —NR$^i$R$^{ii}$ together denotes a 3-7 membered, nitrogen-containing heterocyclyl, which is optionally substituted by one or more identical or different C$_{1-6}$alkyl;
R$^{iii}$ is selected from among hydrogen, C$_{1-6}$alkyl, C$_{3-6}$cycloalkyl and C$_{1-6}$haloalkyl.

In another aspect (B4) the invention relates to compounds (1), wherein
R²-L'- denotes the group

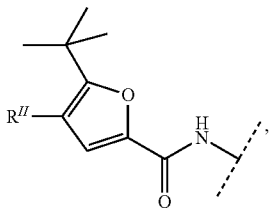

R$^{ii}$ denotes the group R$^i$R$^{ii}$N—CH$_2$—;
R$^i$ is selected from among hydrogen and methyl;
R$^{ii}$ is selected from among iso-propyl, tert-butyl, methyl, dimethylamino-C$_{1-6}$alkyl, methylamino-C$_{1-6}$alkyl- and 3-7 membered, nitrogen-containing heterocyclyl, while this 3-7 membered, nitrogen-containing heterocyclyl may optionally be substituted by one or more identical or different C$_{1-6}$alkyl.

In another aspect (B5) the invention relates to compounds (1), wherein
R²-L'- denotes the group

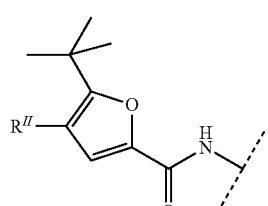

and

R$^{II}$ is selected from among

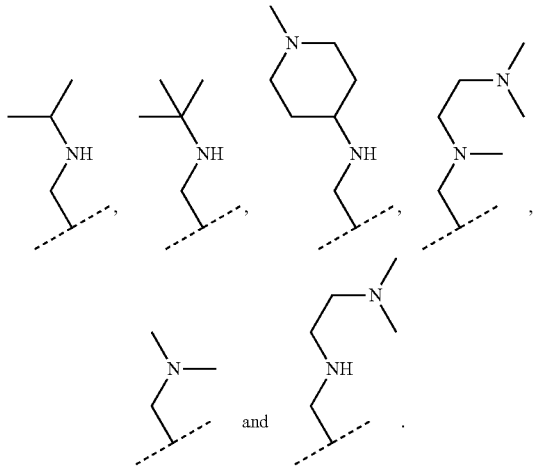

In another aspect (B6) the invention relates to compounds (1), wherein
R²-L'- denotes the group

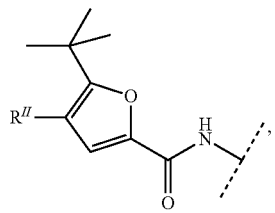

R$^{ii}$ denotes the group R$^i$R$^{ii}$N—CH$_2$— and
the group —NR$^i$R$^{ii}$ together denotes a 3-7 membered, nitrogen-containing heterocyclyl, which is optionally substituted by one or more identical or different In another aspect (B7) the invention relates to compounds (1), wherein
R²-L'- denotes the group

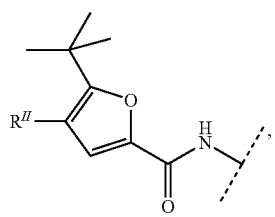

R$^{ii}$ denotes the group R$^i$R$^{ii}$N—CH$_2$— and
the group —NR$^i$R$^{ii}$ together denotes a 5-6 membered, nitrogen-containing heterocyclyl, selected from among pyrrolidinyl, piperidinyl and piperazinyl, while this 5-6 membered heterocyclyl is optionally substituted by one or more identical or different C$_{1-6}$alkyl, particularly methyl.

In another aspect (A11) the invention relates to compounds (1), wherein
the group —NR⁰R¹ together denotes morpholinyl.

In another aspect (B8) the invention relates to compounds (1), wherein
R²-L'- denotes the group

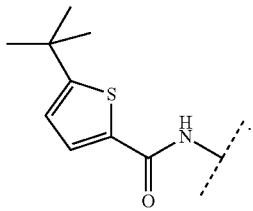

In another aspect (B9) the invention relates to compounds (1), wherein
R²-L'- denotes the group

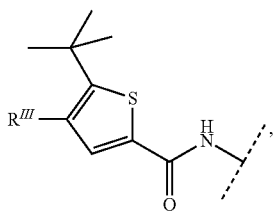

R$^{iii}$ is selected from among R$^i$R$^{ii}$N—CH$_2$— and R$^{iii}$—O—CH$_2$—;
R$^i$ is selected from among hydrogen and C$_{1-6}$alkyl;
R$^{ii}$ is selected from among C$_{1-6}$alkyl, (C$_{1-6}$alkyl)$_2$N—C$_{1-6}$alkyl, (C$_{1-6}$alkyl)NH—C$_{1-6}$alkyl- and 3-7 membered heterocyclyl, while this 3-7 membered heterocyclyl may optionally be substituted by one or more identical or different C$_{1-6}$alkyl;
or
the group —NR$^i$R$^{ii}$ together denotes a 3-7 membered, nitrogen-containing heterocyclyl which is optionally substituted by one or more identical or different C$_{1-6}$alkyl;
R$^{iii}$ is selected from among hydrogen, C$_{1-6}$alkyl, C$_{3-6}$cycloalkyl and C$_{1-6}$haloalkyl.

In another aspect (B10) the invention relates to compounds (1), wherein
R²-L'- denotes the group

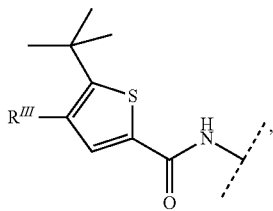

R$^{iii}$ denotes the group R$^i$R$^{ii}$N—CH$_2$—;
R$^i$ is selected from among hydrogen and methyl;
R$^{ii}$ is selected from among iso-propyl, tert-butyl, methyl, dimethylamino-C$_{1-6}$alkyl, methylamino-C$_{1-6}$alkyl- and 3-7 membered, nitrogen-containing heterocyclyl, while this 3-7 membered, nitrogen-containing heterocyclyl may optionally be substituted by one or more identical or different C$_{1-6}$alkyl.

In another aspect (B11) the invention relates to compounds (1), wherein
R²-L'- denotes the group

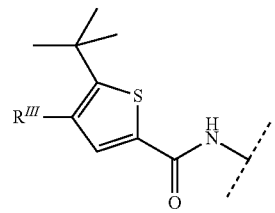

and
R$^{iii}$ is selected from among

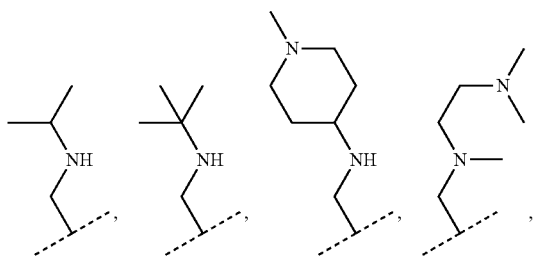

In another aspect (B12) the invention relates to compounds (1), wherein
R²-L'- denotes the group

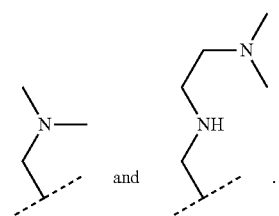

R$^{iii}$ denotes the group R$^i$R$^{ii}$N—CH$_2$— and
the group —NR$^i$R$^{ii}$ together denotes a 3-7 membered, nitrogen-containing heterocyclyl, which is optionally substituted by one or more identical or different C$_{1-6}$alkyl.

In another aspect (B13) the invention relates to compounds (1), wherein

R²-L'- denotes the group

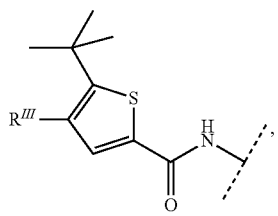

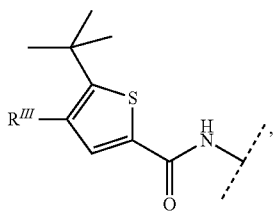

$R^{iii}$ denotes the group $R^iR^{ii}N\text{—}CH_2\text{—}$ and the group $\text{—}NR^iR^{ii}$ together denotes a 5-6 membered, nitrogen-containing heterocyclyl selected from among pyrrolidinyl, piperidinyl and piperazinyl, while this 5-6 membered heterocyclyl is optionally substituted by one or more identical or different $C_{1-6}$alkyl, particularly methyl.

In another aspect (B14) the invention relates to compounds (1), wherein $R^2\text{-}L'\text{-}$ denotes the group

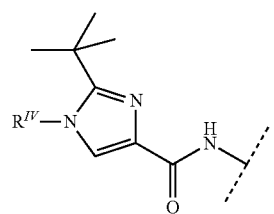

and $R^{IV}$ denotes methyl or ethyl, preferably methyl.

In another aspect (B15) the invention relates to compounds (1), wherein $R^2\text{-}L'\text{-}$ denotes the group

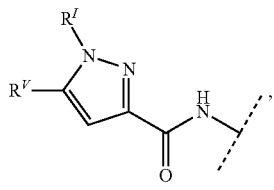

$R^I$ is selected from among iso-propyl and tert-butyl and
$R^V$ is selected from among methyl, ethyl, n-propyl, iso-propyl and cyclopropyl.

In another aspect (B16) the invention relates to compounds (1), wherein $R^2\text{-}L'\text{-}$ denotes the group

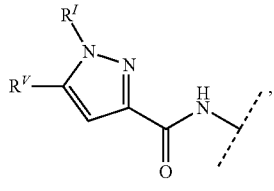

$R^I$ is selected from among iso-propyl and tert-butyl;
$R^V$ is selected from among $R^iR^{ii}N\text{—}CH_2\text{—}$ and $R^{iii}\text{—}O\text{—}CH_2\text{—}$;
$R^i$ is selected from among hydrogen and $C_{1-6}$alkyl;

$R^{ii}$ is selected from among $C_{1-6}$alkyl, $(C_{1-6}$alkyl$)_2$N—$C_{1-6}$alkyl, $(C_{1-6}$alkyl$)$NH—$C_{1-6}$alkyl- and 3-7 membered heterocyclyl, while this 3-7 membered heterocyclyl may optionally be substituted by one or more identical or different $C_{1-6}$alkyl;

or the group $\text{—}NR^iR^{ii}$ together denotes a 3-7 membered, nitrogen-containing heterocyclyl, which is optionally substituted by one or more identical or different $C_{1-6}$alkyl;

$R^{iii}$ is selected from among hydrogen, $C_{1-6}$alkyl, $C_{3-6}$cycloalkyl and $C_{1-6}$haloalkyl.

In another aspect (B17) the invention relates to compounds (1), wherein $R^2$ denotes the group

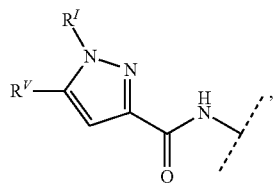

$R^I$ is selected from among iso-propyl and tert-butyl;
$R^{II}$ denotes the group $R^iR^{ii}N\text{—}CH_2\text{—}$;
$R^i$ is selected from among hydrogen and methyl;
$R^{ii}$ is selected from among iso-propyl, tert-butyl, methyl, dimethylamino-$C_{1-6}$alkyl-, methylamino-$C_{1-6}$alkyl- and 3-7 membered, nitrogen-containing heterocyclyl, while this 3-7 membered, nitrogen-containing heterocyclyl may optionally be substituted by one or more identical or different $C_{1-6}$alkyl.

In another aspect (B18) the invention relates to compounds (1), wherein $R^2$ denotes the group

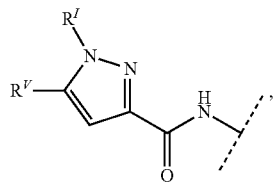

$R^I$ is selected from among iso-propyl and tert-butyl, and
$R^{II}$ is selected from among

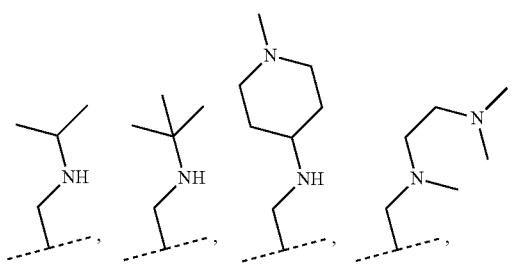

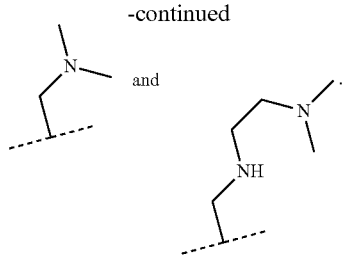

In another aspect (B19) the invention relates to compounds (1), wherein
R² denotes the group

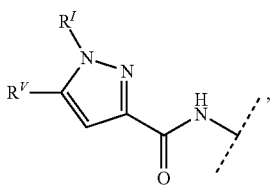

R$^I$ is selected from among iso-propyl and tert-butyl, and R$^{II}$ denotes the group R$^i$R$^{ii}$N—CH$_2$— and
the group —NR$^i$R$^{ii}$ together denotes a 3-7 membered, nitrogen-containing heterocyclyl, which is optionally substituted by one or more identical or different In another aspect (B20) the invention relates to compounds (1), wherein
R² denotes the group

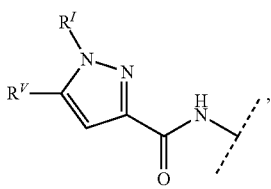

R$^I$ is selected from among iso-propyl and tert-butyl, and R$^{II}$ denotes the group R$^i$R$^{ii}$N—CH$_2$— and
the group —NR$^i$R$^{ii}$ together denotes a 5-6 membered, nitrogen-containing heterocyclyl, selected from among pyrrolidinyl, piperidinyl and piperazinyl, while this 5-6 membered heterocyclyl is optionally substituted by one or more identical or different C$_{1-6}$alkyl, particularly methyl.

In another aspect (B21) the invention relates to compounds (1), wherein
R²-L'- denotes the group

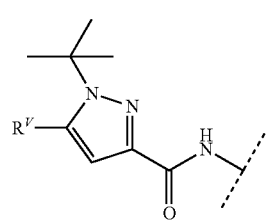

and

R$^V$ is selected from among methyl, ethyl, n-propyl, iso-propyl and cyclopropyl.

In another aspect (B22) the invention relates to compounds (1), wherein
R²-L'- denotes the group

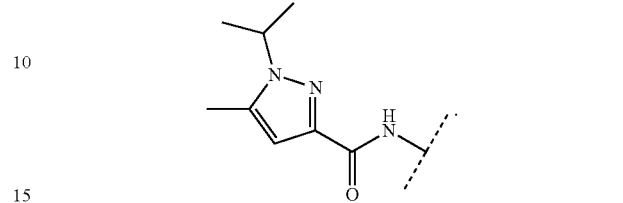

In another aspect (B23) the invention relates to compounds (1), wherein
R²-L'- is selected from among

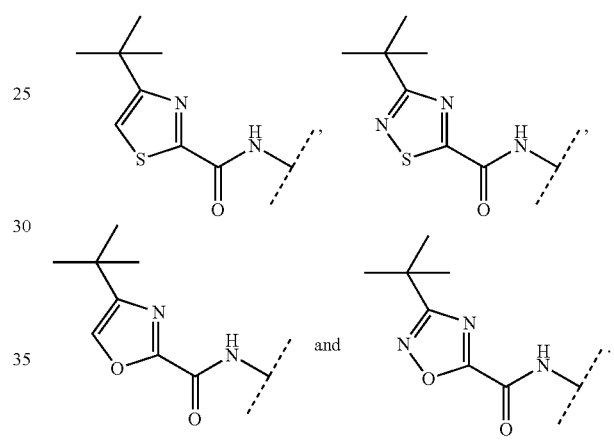

All the above-mentioned structural aspects A1 to A11, B1 to B23 and C1 and C2 are preferred embodiments of the various aspects A0, B0 or C0. The structural aspects A0 to A11, B0 to B23, and C0 to C2 relating to different molecular parts of the compounds (1) according to the invention may be permutated with one another as desired in combinations ABC, so as to obtain preferred compounds (1). Each combination ABC represents and defines individual embodiments or generic amounts of compounds according to the invention. Each individual embodiment or partial quantity defined by this combination is expressly also included and is a subject of the invention.

The present invention further relates to hydrates, solvates, polymorphs, metabolites, derivatives and prodrugs of compounds of general formula (1).

In another aspect the invention relates to compounds of general formula (1)—or the pharmaceutically acceptable salts thereof—as medicaments.

In another aspect the invention relates to compounds of general formula (1)—or the pharmaceutically acceptable salts thereof—for use in the treatment and/or prevention of cancer, infections, inflammations and autoimmune diseases.

In another aspect the invention relates to compounds of general formula (1)—or the pharmaceutically acceptable salts thereof—for use in the treatment and/or prevention of cancer.

In another aspect the invention relates to compounds of general formula (1)—or the pharmaceutically acceptable salts thereof—for use in the treatment and/or prevention of colon carcinomas, melanomas, cancer of the gall bladder, bile duct cancer and thyroid carcinomas.

In another aspect the invention relates to a process for the treatment and/or prevention of cancer comprising administering a therapeutically effective amount of a compound of general formula (1)—or one of the pharmaceutically acceptable salts thereof—to a human being.

In another aspect the invention relates to a pharmaceutical preparation containing as active substance one or more compounds of general formula (1)—or the pharmaceutically acceptable salts thereof—optionally in combination with conventional excipients and/or carriers.

In another aspect the invention relates to a pharmaceutical preparation comprising a compound of general formula (1)— or one of the pharmaceutically acceptable salts thereof—and at least one other cytostatic or cytotoxic active substance different from formula (1).

DEFINITIONS

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number (x<y), indicates that the chains or ring structure or combination of chains and ring structure as a whole, specified and mentioned in direct association, may consist of a maximum of y and a minimum of x carbon atoms.

The indication of the number of members in groups that contain one or more heteroatom(s) (heteroalkyl, heteroaryl, heteroarylalkyl, heterocyclyl, heterocycylalkyl) relates to the total atomic number of all the ring members or chain members or the total of all the ring and chain members.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$-alkyl" includes for example H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Further examples of alkyl are methyl (Me; —CH$_3$C), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl (neo-pentyl; —CH$_2$C(CH$_3$)$_3$), 2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 2,3-dimethyl-1-butyl (—CH$_2$CH(CH$_3$)CH(CH$_3$)CH$_3$), 2,2-dimethyl-1-butyl (—CH$_2$C(CH$_3$)$_2$CH$_2$CH$_3$), 3,3-dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy.

The term alkylene can also be derived from alkyl. Alkylene is bivalent, unlike alkyl, and requires two binding partners. Formally the second valency is produced by removing a hydrogen atom in an alkyl. Corresponding groups are for example —CH$_3$ and —CH$_2$—, —CH$_2$CH$_3$ and —CH$_2$CH$_2$— or >CHCH$_3$ etc.

The term "$C_{1-4}$-alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene. The above definition for alkylene also applies if alkylene is part of another group such as for example in HO—$C_{x-y}$-alkylene-amino or H$_2$N—$C_{x-y}$-alkyleneoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If formally in an alkylene as hereinbefore defined having at least two carbon atoms, two hydrogen atoms at adjacent carbon atoms are removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenyleneamino or $H_2N$—$C_{x-y}$-alkenyleneoxy.

Unlike alkyl, alkynyl consists of at least two carbon atoms, wherein at least two adjacent carbon atoms are joined together by a C—C triple bond. If formally in an alkyl as hereinbefore defined having at least two carbon atoms, two hydrogen atoms in each case at adjacent carbon atoms are removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another group, as in $C_{x-y}$-alkynylamino or $C_{x-y}$-alkynyloxy, for example.

Unlike alkylene, alkynylene consists of at least two carbon atoms, wherein at least two adjacent carbon atoms are joined together by a C—C triple bond. If formally in an alkylene as hereinbefore defined having at least two carbon atoms, two hydrogen atoms in each case at adjacent carbon atoms are removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x-y}$-alkynyleneamino or $H_2N$—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —Cl=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl) unlike haloalkyl is bivalent and requires two binding partners. Formally, the second valency is formed by removing a hydrogen atom from a haloalkyl.

Corresponding groups are for example —$CH_2F$ and —CHF—, —$CHFCH_2F$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthalene), bicyclo[2.2.1]heptyl (norbornyl), bicyclo[4.1.0]heptyl (norcaranyl), bicyclo-[3.1.1]heptyl (pinanyl), spiro[2.5]octyl, spiro[3.3]heptyl etc.

The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained.

The term cycloalkylene can thus be derived from the previously defined cycloalkyl.

Cycloalkylene, unlike cycloalkyl, is bivalent and requires two binding partners. Formally, the second valency is obtained by removing a hydrogen atom from a cycloalkyl.

Corresponding groups are for example cyclohexyl and

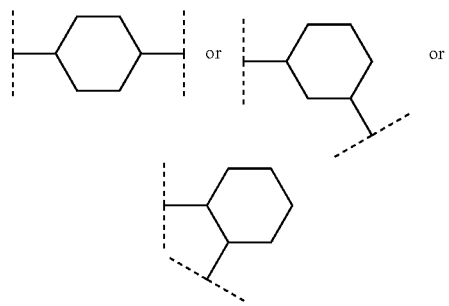

(cyclohexylene).

The above definition for cycloalkylene also applies if cycloalkylene is part of another group as in HO—$C_{x-y}$-cycloalkyleneamino or $H_2N$—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If formally in a cycloalkyl as hereinbefore defined two hydrogen atoms at adjacent cyclic carbon atoms are removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4.5]dec-2-ene etc.

The above definition for cycloalkenyl also applies when cycloalkenyl is part of another group as in $C_{x-y}$-cycloalkenylamino or $C_{x-y}$-cycloalkenyloxy, for example.

If the free valency of a cycloalkenyl is saturated, then an unsaturated alicyclic group is obtained.

The term cycloalkenylene can thus be derived from the previously defined cycloalkenyl.

Cycloalkenylene, unlike cycloalkenyl, is bivalent and requires two binding partners. Formally the second valency is obtained by removing a hydrogen atom from a cycloalkenyl. Corresponding groups are for example cyclopentenyl and

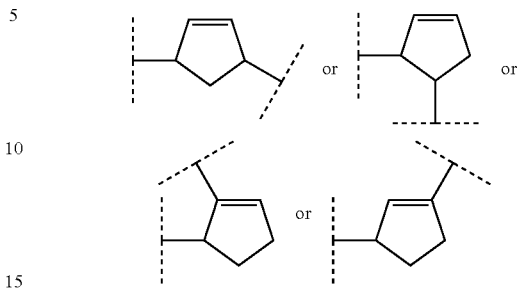

(cyclopentenylene) etc.

The above definition for cycloalkenylene also applies when cycloalkenylene is part of another group as in HO—$C_{x-y}$-cycloalkenyleneamino or $H_2N$—$C_{x-y}$-cycloalkenyleneoxy, for example.

Aryl denotes mono-, bi- or tricyclic carbocycles with at least one aromatic carbocycle. Preferably it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g. phenyl and

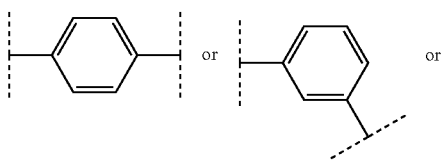

(o, m, p-phenylene), naphthyl and

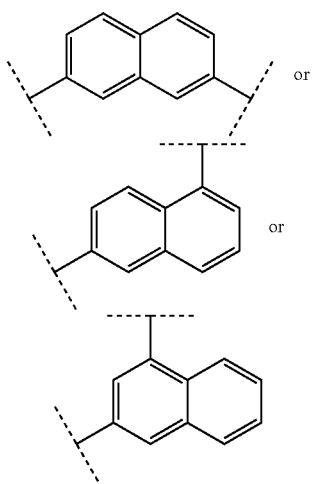

etc.

The above definition for arylene also applies when arylene is part of another group as in HO-aryleneamino or H₂N-aryleneoxy for example.

Heterocyclyl denotes ring systems, which are derived from the previously defined cycloalkyl, cycloalkenyl and aryl by replacing one or more of the groups —CH₂— independently of one another in the hydrocarbon rings by the groups —O—, —S— or —NH or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO—, sulphone —SO₂—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-azabicyclo[3.2.1]octyl, 8-azabicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3.8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4.5]decyl etc.

Further examples are the structures illustrated below, which may be attached via each hydrogen-carrying atom (exchanged for hydrogen):

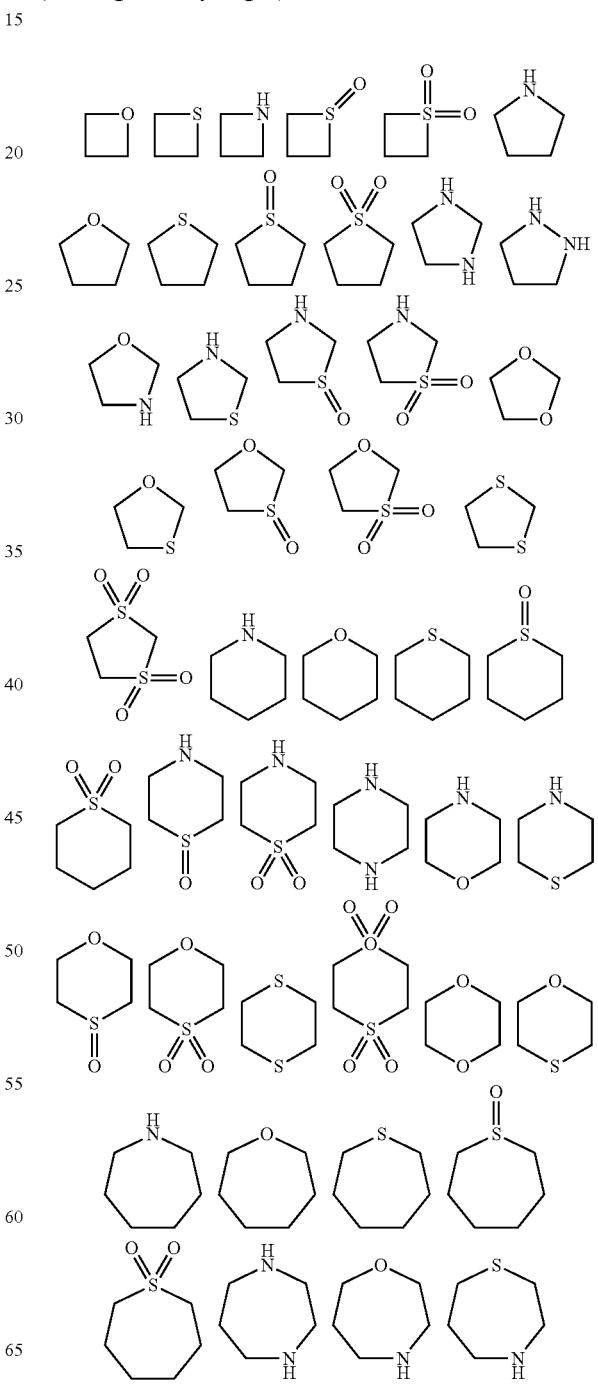

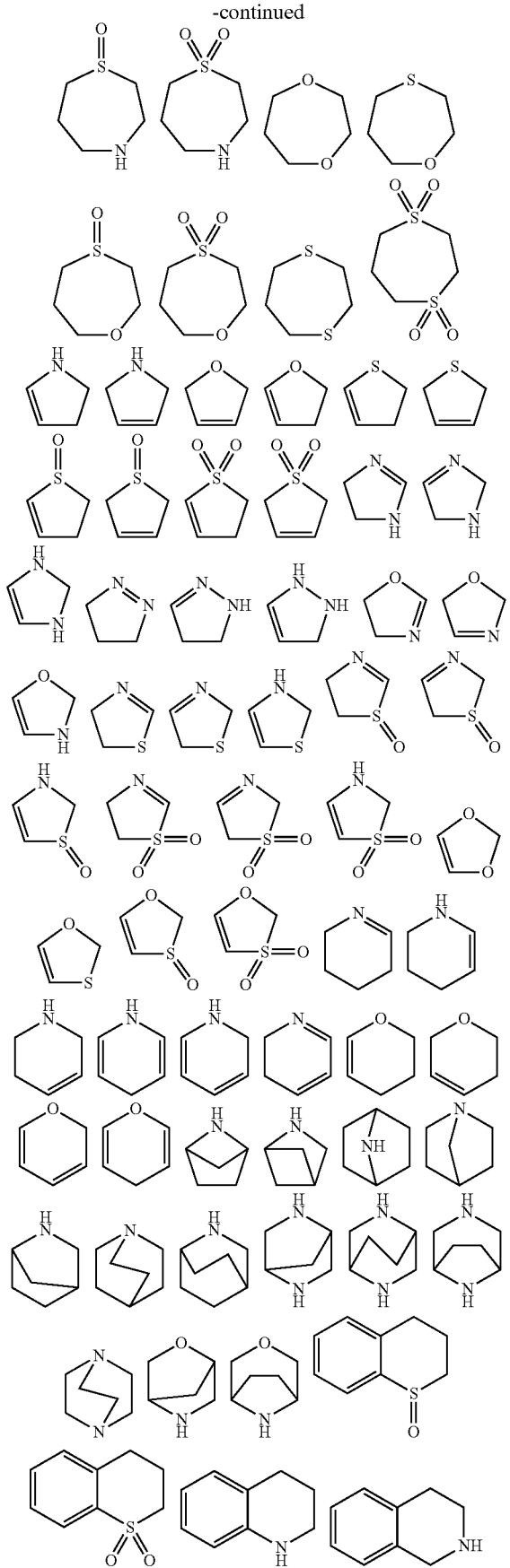
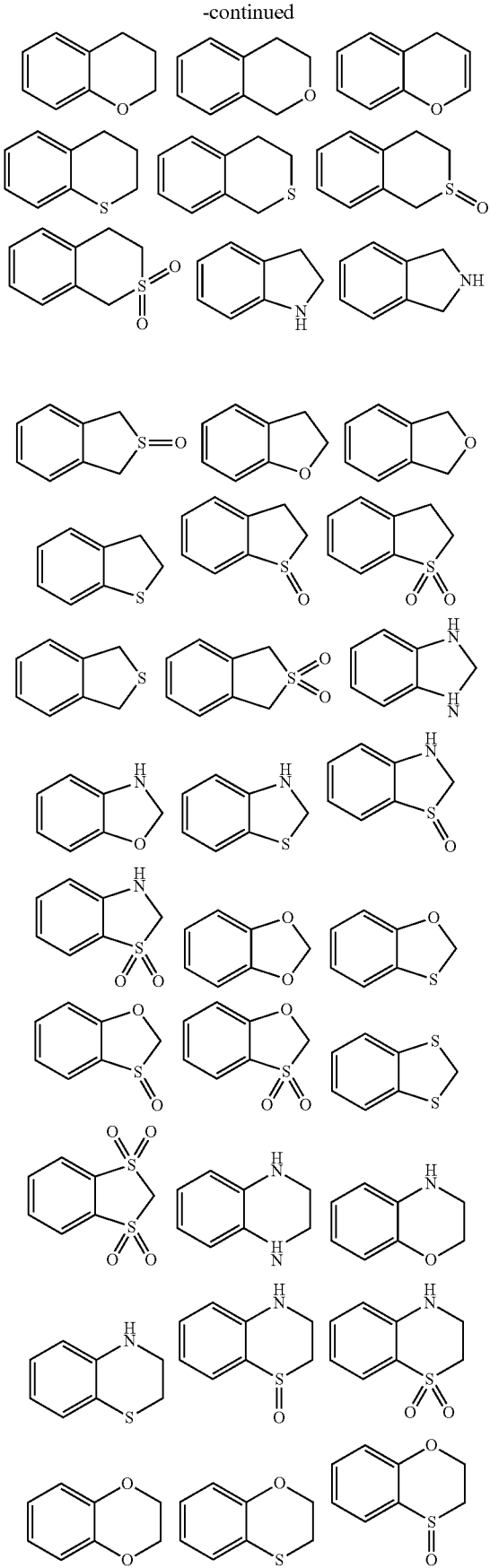

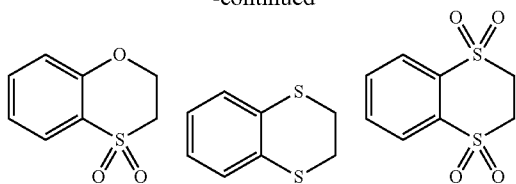

The above definition of heterocyclyl also applies if heterocyclyl is part of another group as in heterocyclylamino or heterocyclyloxy for example.

If the free valency of a heterocyclyl is saturated, then a heterocyclic group is obtained.

The term heterocyclylene is also derived from the previously defined heterocyclyl.

Heterocyclylene unlike heterocyclyl is bivalent and requires two binding partners.

Formally, the second valency is obtained by removing a hydrogen atom from a heterocyclyl. Corresponding groups are for example piperidinyl and

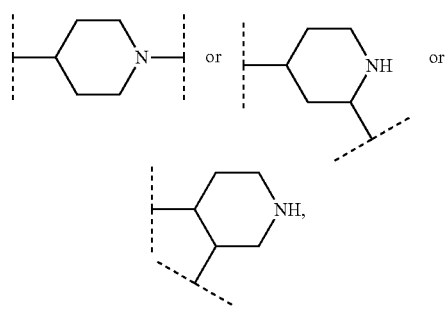

2,3-dihydro-1H-pyrrolyl and

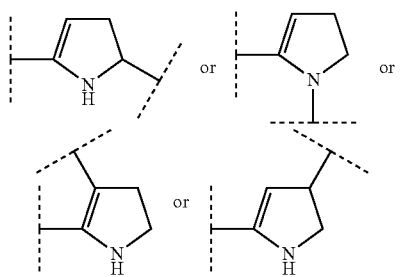

etc.

The above definition of heterocyclylene also applies if heterocyclylene is part of another group as in HO-heterocyclyleneamino or $H_2N$-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

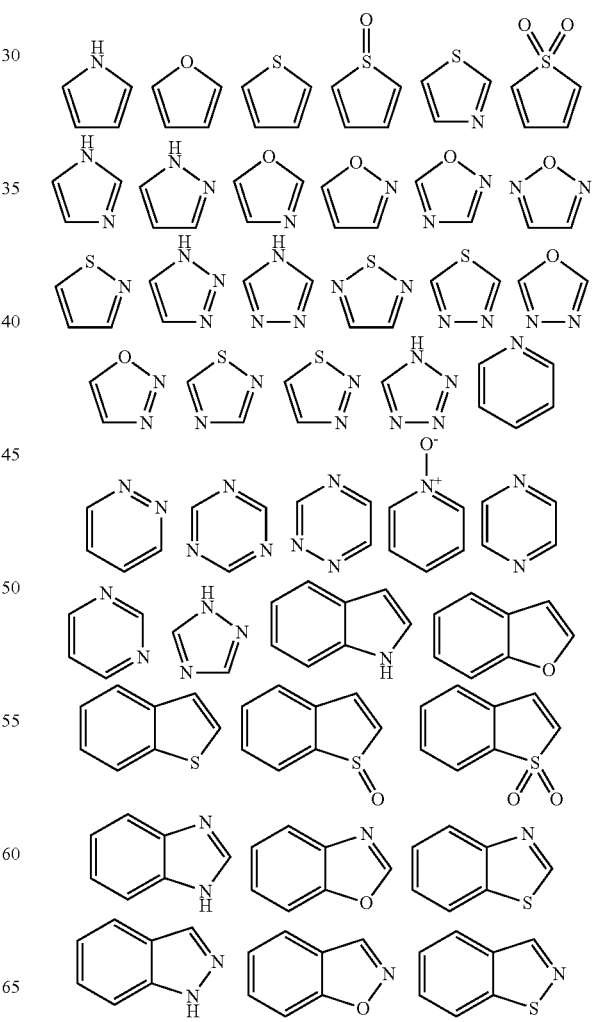

-continued

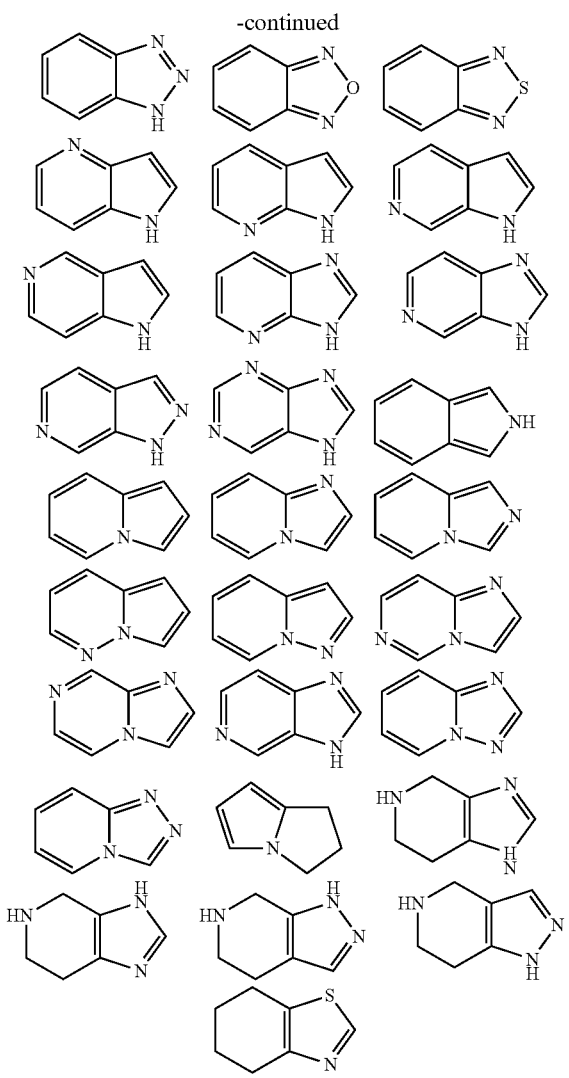

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene is also derived from the previously defined heteroaryl.

Heteroarylene, unlike heteroaryl, is bivalent and requires two binding partners. Formally, the second valency is obtained by removing a hydrogen atom from a heteroaryl.

Corresponding groups are for example pyrrolyl and

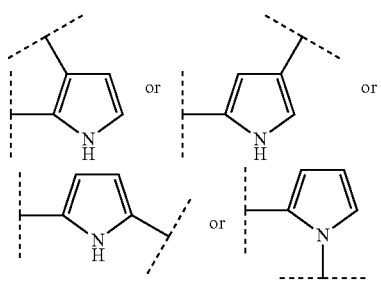

etc.

The above definition of heteroarylene also applies when heteroarylene is part of another group as in HO-heteroaryleneamino or $H_2N$-heteroaryleneoxy, for example.

By substituted is meant that a hydrogen atom which is bound directly to the atom under consideration, is replaced by another atom or another group of atoms (substituent).

Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —CH$_2$— or sulphur atoms of a ring system.

Stereochemistry/Solvates/Hydrates: Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally for the purposes of the present invention the solvated forms, e.g. hydrates, are to be regarded as of equal value to the unsolvated forms.

Salts: The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio.

The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsnilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof).

Salts of acids other than those mentioned above, which are useful for example for purifying or isolating the compounds from the reaction mixtures (e.g. trifluoracetates), are also to be regarded as part of the invention.

Some abbreviated notations and their structure correspondences are listed below:

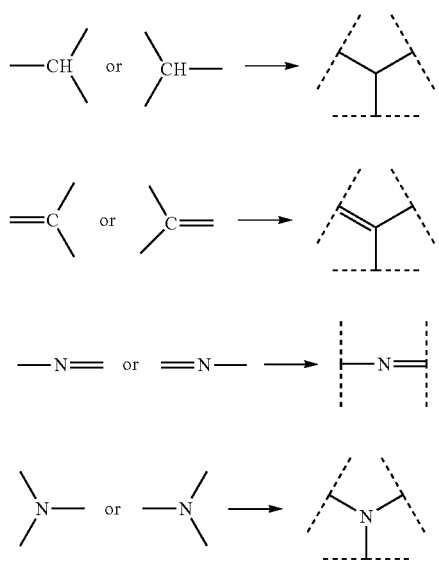

If for example in the sequence X—Y—Z the component Y is supposed to correspond to the structural section —N═, this means both X═N—Z and also X—N═Z.

In a representation such as for example

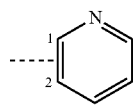

the dotted line means that the ring system may be attached to the molecule via the carbon 1 or 2, and is thus equivalent to the following representation

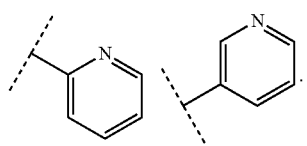

In a representation such as for example

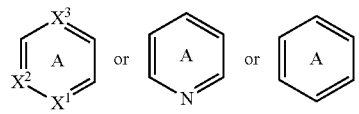

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

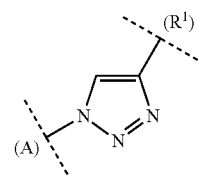

or $(R^2)$—C(O)NH— or $(R^2)$—NHC(O)—;

Groups or substituents are frequently selected from among a number of alternative groups/substituents with a corresponding group designation (e.g. $R^a$, $R^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

| List of abbreviations | |
|---|---|
| Ac | acetyl |
| aq. | aquatic, aqueous |
| ATP | adenosine triphosphate |
| Bn | benzyl |
| Boc | tert-butyloxycarbonyl |
| Bu | butyl |
| c | concentration |
| CDI | carbonyldiimidazole |
| cHex | cyclohexane |
| d | day(s) |
| TLC | thin layer chromatography |
| DCC | dicyclohexylcarbodiimide |
| DCM | dichloromethane |
| DEA | diethylamine |
| DIPEA | N-ethyl-N,N-diisopropylamine (Hünig base) |
| DMAP | 4-N,N-dimethylaminopyridine |
| DME | 1,2-dimethoxyethane |
| DMF | N,N-dimethylformamide |
| DMSO | dimethylsulphoxide |

-continued

List of abbreviations

| | |
|---|---|
| DPPA | diphenylphosphorylazide |
| EDC | 1-ethyl-3-(3-dimethylaminopropyl)-carbodiimide |
| EDTA | ethylendiamintetraacetic acid |
| EA | ethyl acetate (ethyl ester of acetic acid) |
| EGTA | ethyleneglycoltetraacetic acid |
| eq | equivalent(s) |
| ESI | electron spray ionization |
| Et | ethyl |
| $Et_2O$ | diethyl ether |
| EtOAc | ethyl acetate |
| EtOH | ethanol |
| h | hour |
| HATU | O-(7-azabenzotriazol-1-yl)-N,N,N'N'-tetramethyl-uronium hexafluorophosphate |
| hex | hexyl |
| HPLC | high performance liquid chromatography |
| Hünig base | N-ethyl-N,N-diisopropylamine (DIPEA) |
| i | iso |
| cat. | catalyst, catalytic |
| conc. | concentrated |
| LC | liquid chromatography |
| sln. | solution |
| mCPBA | m-chloroperbenzoic acid |
| Me | methyl |
| MeOH | methanol |
| min | minutes |
| MPLC | medium pressure liquid chromatography |
| MS | mass spectrometry |
| NMM | N-methylmorpholine |
| NMP | N-methylpyrrolidone |
| NP | normal phase |
| n.a. | not available |
| PBS | phosphate-buffered saline solution |
| PE | petroleum ether |
| PG | protecting group |
| Ph | phenyl |
| PMSF | benzylsulphonic acid fluoride |
| PPCA | propanephosphonic acid cycloanhydride |
| Pr | propyl |
| Py | pyridine |
| pyBOP | benzotriazol-1-yl-oxy-tris-pyrrolidino-phosphonium hexafluorophosphate |
| rac | racemic |
| red. | reduction |
| $R_f$(Rf) | retention factor |
| RP | reversed phase |
| RT | ambient temperature |
| $S_N$ | nucleophilic substitution |
| TBAF | tetrabutylammonium fluoride |
| TBME | tert-butylmethylether |
| TBTU | O-(benzotriazol-1-yl)-N,N,N,N'-tetramethyl-uronium tetrafluoroborate |
| TEA | triethylamine |
| temp. | temperature |
| tert. | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | p-toluenesulphonic acid |
| UV | ultraviolet |
| Z | benzyloxycarbonyl |

Features and advantages of the present invention will become apparent from the following detailed Examples, which illustrate the fundamentals of the invention by way of example, without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds are named according to the Beilstein rules using the Autonom software (Beilstein) or by using Lexichem (release 2.0.0; OpenEye Scientific Software). If a compound is to be represented both by a structural formula and by its nomenclature, in the event of a conflict the structural formula is decisive.

Microwave reactions are carried out in an initiator/reactor made by Biotage or in an Explorer made by CEM in sealed containers (preferably 2, 5 or 20 mL), preferably with stirring.

Chromatography

For preparative medium pressure chromatography (MPLC) silica gel made by Millipore (name: Granula Silica Si-60A 35-70 µm, NP phase) or C-18 RP-silica gel (RP-phase) made by Macherey Nagel (name: Polygoprep 100-50 C18) is used. Automated normal phase chromatography is also carried out on a CombiFlash Companion XL apparatus in combination with a CombiFlash Foxy 200 fraction collector made by Isco. For this, commercially obtainable RediSepRf (for example 120 g silica gel) one-way columns are used. In addition, the automated normal phase chromatography may also be carried out using an Isolera Flash Purification apparatus made by Biotage. For this, one-way column SNAP cartridges (e.g. 50 g silica gel) that are commercially obtainable from Biotage are used.

The thin layer chromatography is carried out on ready-made silica gel 60 TLC plates on glass (with fluorescence indicator F-254) made by Merck.

The preparative high pressure chromatography (HPLC) of the example compounds according to the invention is carried out with columns made by Waters (names: XTerra Prep. MS C18, 5 µm, 30×100 mm or XTerra Prep. MS C18, 5 µm, 50×100 mm OBD or Symmetrie C18, 5 µm, 19×100 mm or Sunfire C18 OBD, 19×100 mm, 5 µm or Sunfire Prep C 10 µm OBD 50×150 mm or X-Bridge Prep C18 5 µm OBD 19×50 mm or X-Bridge Prep C18 10 µm OBD 50×150 mm), Agilent (name: Zorbax SB-C8 5 µm PrepHT 21.2×50 mm) and Phenomenex (names: Gemini C18 5 µm AXIA 21.2×50 mm or Gemini C18 10 µm 50×150 mm). The compounds are eluted using either different gradients of $H_2O$/acetonitrile or $H_2O$/MeOH, wherein either 0.1% HCOOH is added to the water (acid conditions). For the chromatography under basic conditions $H_2O$/acetonitrile gradients are also used, and the water is made basic using the following recipe: 5 mL of an ammonium hydrogen carbonate solution (158 g on 1 L $H_2O$) and 2 mL ammonia (7M in MeOH) are made up to 1 L with $H_2O$.

The preparative high pressure chromatography (HPLC) on normal phase of the example compounds according to the invention is carried out with columns made by Macherey & Nagel (name: Nucleosil, 50-7, 40×250 mm) and VDSoptilab (name: Kromasil 100 $NH_2$, 10 µM, 50×250 mm). The compounds are eluted using different gradients of DCM/MeOH, wherein 0.1% $NH_3$ is added to the MeOH.

The analytical HPLC (reaction control) of intermediate compounds is carried out using columns made by Agilent (names: Zorbax SB-C8, 5 µm, 21.2×50 mm or Zorbax SB-C8 3.5 µm 2.1×50 mm) and Phenomenex (name: Gemini C18 3 µm 2×30 mm). The analytical equipment is also equipped with a mass detector in each case.

HPLC-Mass Spectroscopy/UV-Spectrometry

The retention times/MS-ESI$^+$ for characterising the example compounds according to the invention are produced using an HPLC-MS apparatus (high performance liquid chromatography with mass detector). Compounds that elute at the injection peak are given the retention time $t_{Ret.}$=0.00.

HPLC-MS-Method
HPLC: Agilent 1100 Series
MS: Agilent LC/MSD SL
Column: Waters, XBridge™ C18, 2.5 μm, 2.1×20 mm
   Part. No. 186003201
Eluant: A: 0.1% $NH_3$ (=pH 9-10)
   B: acetonitrile HPLC grade
Detection: MS: Positive and negative
Mass range: 120-800 m/z
Flow: 1.00 mL/min
Column temp.: 60° C.
Gradient: 0.00 min 5% B
   0.00-2.50 min 5%→95% B
   2.50-2.80 min 95% B
   2.81-3.10 min 95%→5% B The compounds according to the invention are prepared by the methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Reaction scheme 1: Methods of preparing compounds of type I

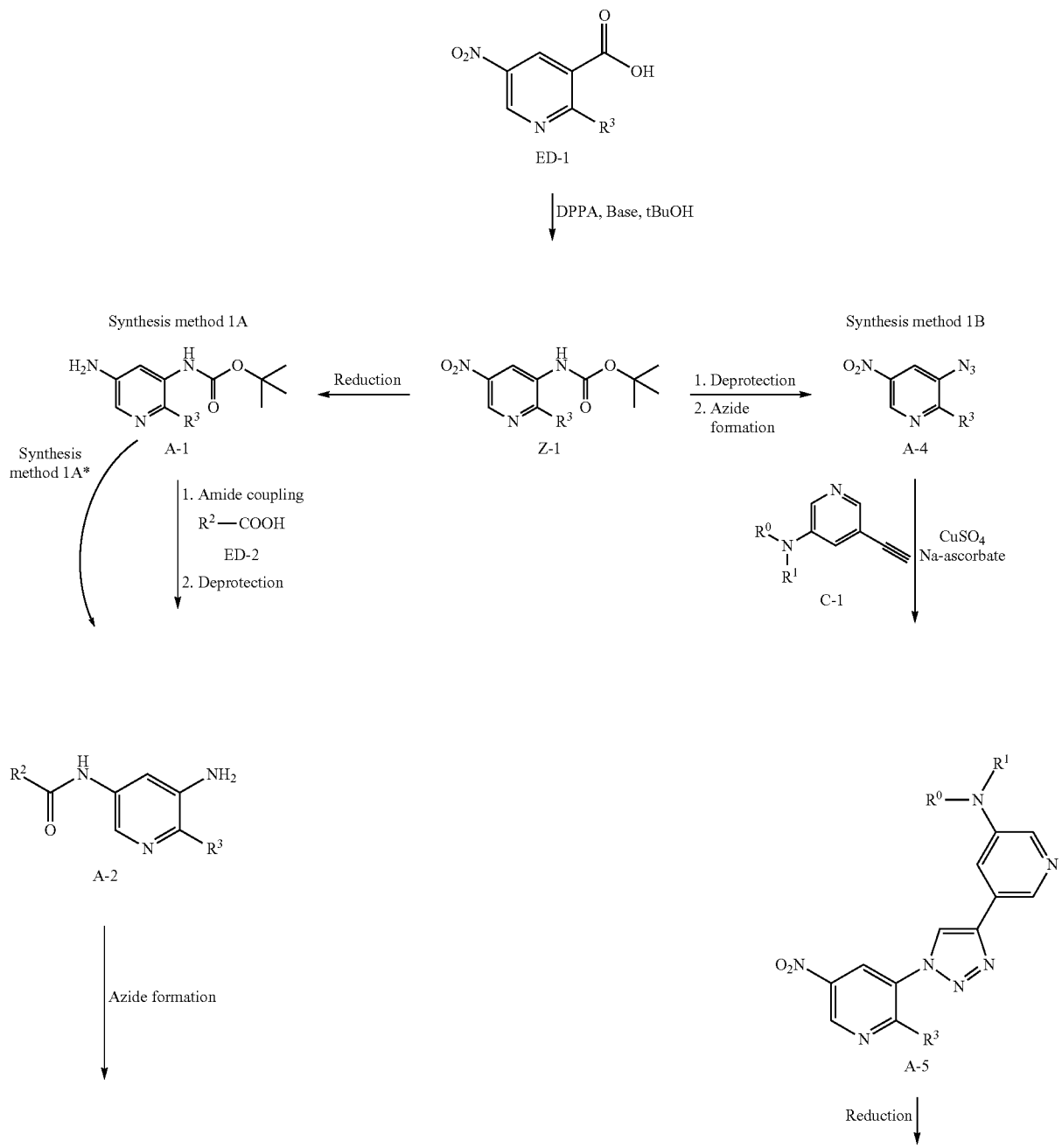

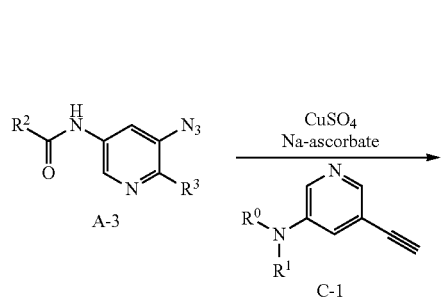 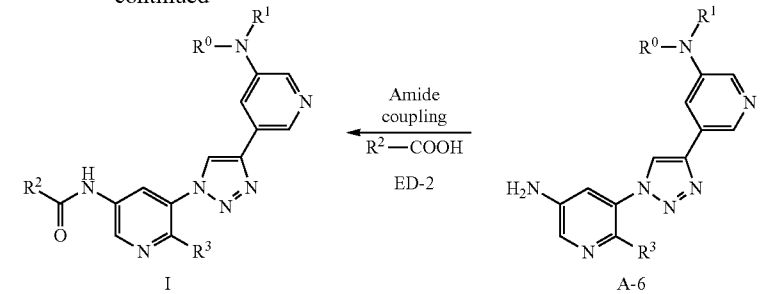

Compounds of Type I according to the invention may be prepared as shown in reaction scheme 1 by synthesis method 1A starting from the azides A-3 by cycloaddition with the alkynes C-1 in the presence of CuSO₄ and sodium ascorbate. The azides A-3 may be synthesised by azide formation with for example tert.-butylnitrite in the presence of TMSN₃ from anilines A-2, which may in turn be prepared starting from the mono-Boc-protected bis-anilines A-1 by an amide coupling reaction with suitable carboxylic acids ED-2 and subsequent deprotection. The amide linking may be carried out using coupling methods known from the literature such as for example activation to the acid chloride using SOCl₂, oxalyl chloride/DMF or GHOSEZ reagent. Moreover, coupling reagents such as for example HATU, TBTU, DCC, PPCA and other common reagents may also be used for the amide linking. The mono-Boc-protected bis-anilines A-1 may be prepared by reduction of the nitro group from the nitro compounds Z-1, which may be synthesised from the nicotinic acids ED-1 by acid decomposition (for example according to CURTIUS) using DPPA in tert.-BuOH.

In a modification of the normal synthesis method 1A, if suitable additionally functionalised carboxylic acids R²COOH (ED-2) are used, anilines A-2 may be further derivatised at these functions after or during the amide coupling, i.e. starting from aniline A-1 further reaction steps have to be carried out besides the amide linking and optionally special carboxylic acids ED-2 have to be prepared (alternative final reaction steps, synthesis method 1A*).

In a reversal of the reaction sequence the compounds of type I may also be prepared by synthesis method 1B. The nitro compounds Z-1 are first of all deprotected at the amino function and then converted into the azides A-4, which are then reacted with the alkynes C-1 by cycloaddition as described above to obtain the nitro compounds A-5. Reduction of the nitro group yields the anilines A-6, which are reacted by an amide coupling reaction with suitable carboxylic acids ED-2 to obtain the compounds of type I according to the invention.

The carboxylic acids ED-2 described are either commercially obtainable or may be prepared from the corresponding educts by methods known from the literature.

A. Preparation of the Alkyne C-1

Reaction scheme 2: Preparation of TMS-protected alkynes B-1

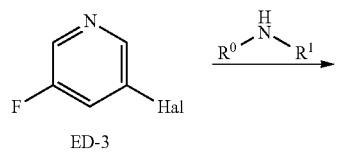

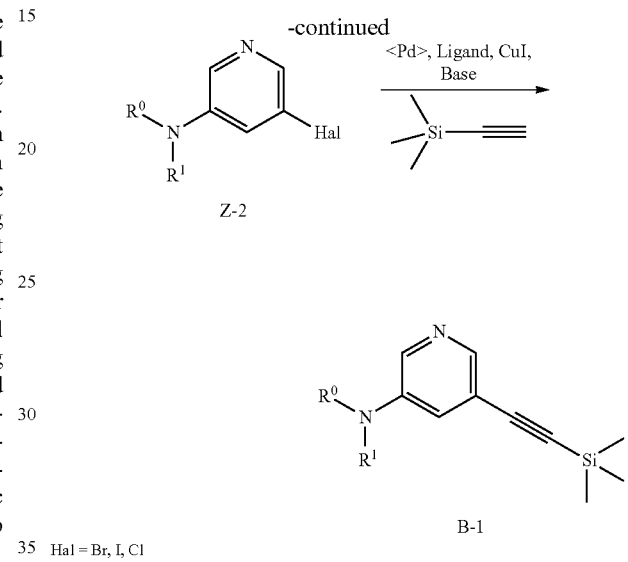

Hal = Br, I, Cl

TMS-protected alkynes B-1 are prepared by palladium-catalysed cross-coupling reactions according to SONOGASHIRA from the corresponding pyridylhalide Z-2 (preferably Br, I or Cl) using TMS-acetylene. The halide Z-2 can be synthesised from the fluoropyridines ED-3 by nucleophilic substitution reactions with secondary and primary (R⁰=H) amines R⁰R¹NH.

a) Method of Synthesising the TMS-Protected Alkyne B-1a

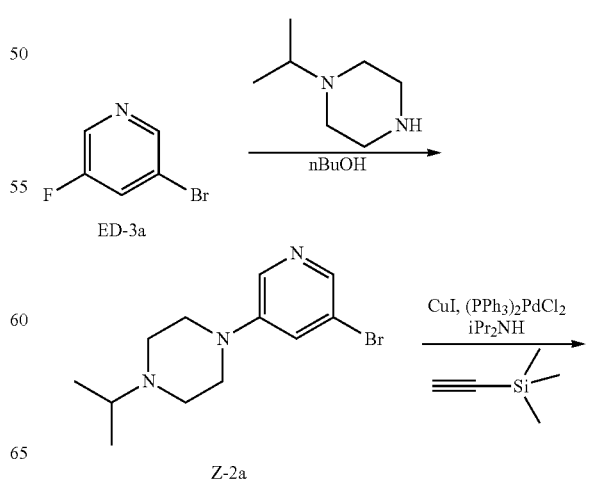

-continued

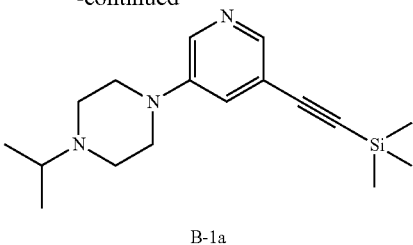

B-1a

Step 1: Synthesis of Z-2a 3-bromo-5-fluoro-pyridine ED-3a (4.26 g, 23.5 mmol) and isopropylpiperazine (7.58 g, 59.1 mmol) are placed in n-BuOH (16 mL) and stirred at 100° C. for 6 d. After cooling the reaction mixture is acidified with 0.1 N hydrochloric acid and extracted three times with EA. The aqueous phase is adjusted to pH 10 with sodium hydroxide solution and extracted three times with DCM. The combined organic phases are dried on $MgSO_4$, filtered and evaporated down using the rotary evaporator. The residue is taken up in a little DCM and added to 4 g of polymer-bound isocyanate pre-swollen in DCM (Argonaut, Art. No. 800260) and stirred for 2 h at RT. Then the resin is filtered off, washed with DCM and evaporated down using the rotary evaporator. The 3-bromo-pyridine Z-2a thus obtained (HPLC-MS: $t_{Ret.}$=1.59 min; MS $(M+H)^+$=284) is used again without any further purification steps.

Step 2: Synthesis of B-1a 3-bromo-pyridine Z-2a (3.88 g, 8.18 mmol), CuI (124 mg, 0.65 mmol) and $(PPh_3)_2PdCl_2$ (95.0 mg, 0.14 mmol) are placed in diisopropylamine (5 mL) under protective gas, combined with TMS-acetylene (1.5 mL, 10.6 mmol) and stirred for 30 min at 100° C. in the microwave reactor. After cooling the reaction mixture is diluted with 1 N hydrochloric acid and extracted three times with DCM. The acid aqueous phase is adjusted to pH 9 and extracted three times with DCM. The combined organic phases are dried on $MgSO_4$, filtered and evaporated down using the rotary evaporator. The residue is purified by normal phase chromatography. The product-containing fractions of B-1a (HPLC-MS: $t_{Ret.}$=2.13 min; MS $(M+H)^+$=203) are evaporated down and dried under high vacuum.

Analogously to this method other TMS-protected alkynes B-1 are synthesised from the pyridylhalides ED-3, the corresponding primary or secondary ($R^0$=H) amines $R^0R^1NH$ and TMS-acetylene (see Table 1).

TABLE 1

| # | Structure | $t_{Ret.}$ (HPLC) [min] | MS $(M + H)^+$ |
|---|---|---|---|
| B-1a | 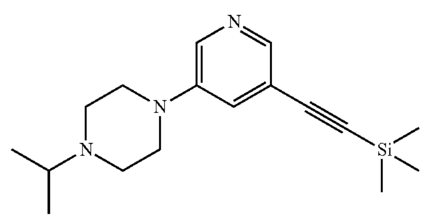 [SMILES: CC(C)N1CCN(c2cncc(C#C[Si](C)(C)C)c2)CC1] | 2.13 | 203 |
| B-1b | 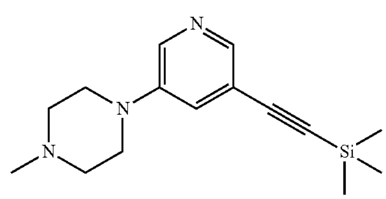 | 1.93 | 274 |
| B-1c | 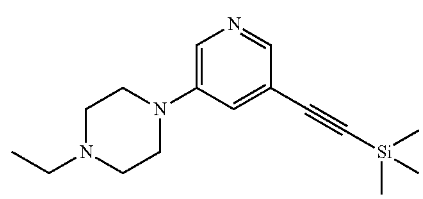 [SMILES: CCN1CCN(c2cncc(C#C[Si](C)(C)C)c2)CC1] | 2.00 | 288 |
| B-1d | 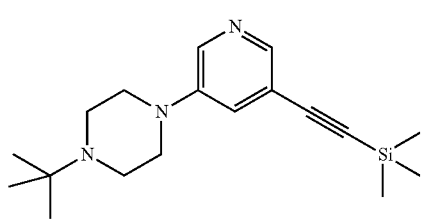 [SMILES: CC(C)(C)N1CCN(c2cncc(C#C[Si](C)(C)C)c2)CC1] | 2.23 | 316 |

TMS-protected alkynes B-1 prepared

TABLE 1-continued

TMS-protected alkynes B-1 prepared

| # | Structure | $t_{Ret.}$ (HPLC) [min] | MS (M + H)$^+$ |
|---|---|---|---|
| B-1e | 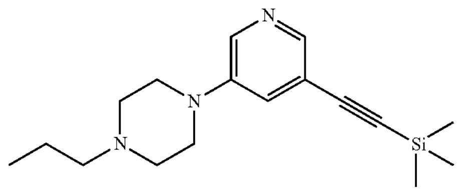 [SMILES: CCCN1CCN(c2cncc(C#C[Si](C)(C)C)c2)CC1] | 2.19 | 302 |
| B-1f | 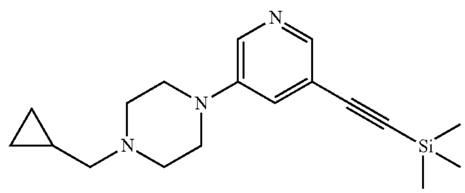 [SMILES: C[Si](C)(C)C#Cc1cncc(N2CCN(CC3CC3)CC2)c1] | 2.15 | 314 |
| B-1g | 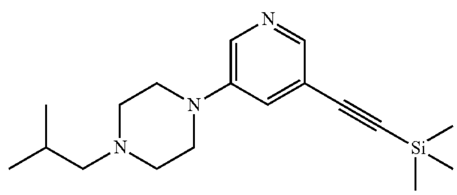 [SMILES: CC(C)CN1CCN(c2cncc(C#C[Si](C)(C)C)c2)CC1] | 2.44 | 316 |
| B-1h | 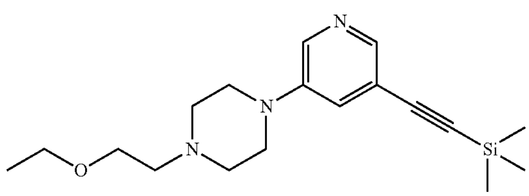 [SMILES: CCOCCN1CCN(c2cncc(C#C[Si](C)(C)C)c2)CC1] | 2.04 | 332 |
| B-1i | 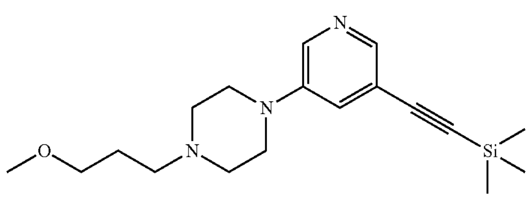 | 1.99 | 332 |
| B-1j | 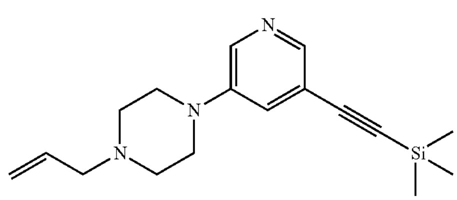 [SMILES: C=CCN1CCN(c2cncc(C#C[Si](C)(C)C)c2)CC1] | 2.12 | 300 |
| B-1k | 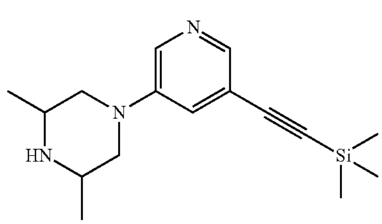 | 1.89 | 288 |

TABLE 1-continued

TMS-protected alkynes B-1 prepared

| # | Structure | $t_{Ret.}$ (HPLC) [min] | MS (M + H)+ |
|---|---|---|---|
| B-1l | 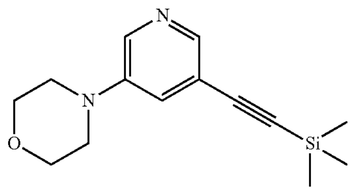 [SMILES: C[Si](C)(C)C#Cc1cncc(N2CCOCC2)c1] | 2.14 | 261 |
| B-1m | 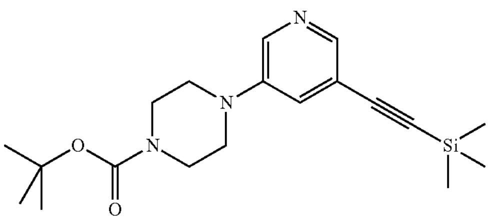 [SMILES: CC(C)(C)OC(=O)N1CCN(c2cncc(C#C[Si](C)(C)C)c2)CC1] | 2.27 | 360 |
| B-1n | 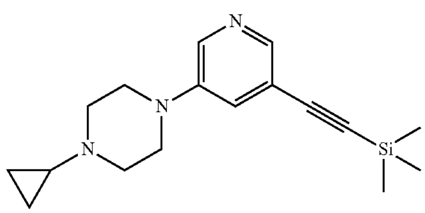 [SMILES: C[Si](C)(C)C#Cc1cncc(N2CCN(C3CC3)CC2)c1] | 2.16 | 300 |

Reaction scheme 3: Release of the alkynes C-1 from the TMS-protected alkynes B-1

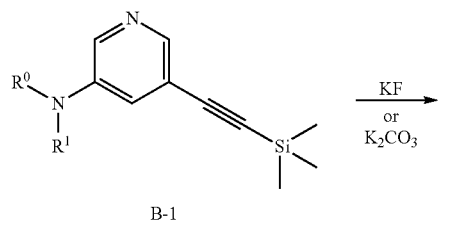

The alkynes C-1 may be liberated in situ from the TMS-protected compounds B-1 using KF, K$_2$CO$_3$ or other cleaving reagents known from the literature, immediately before they are further used. In most cases, however, isolation is possible.

B. Preparation of Special Carboxylic Acids ED-2

Reaction scheme 4: Preparation of special pyrazolecarboxylic acids ED-2 (synthesis method A).

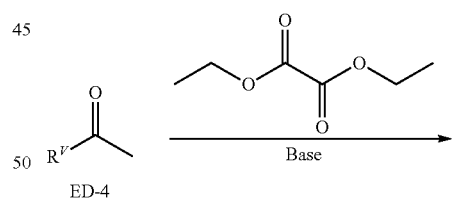

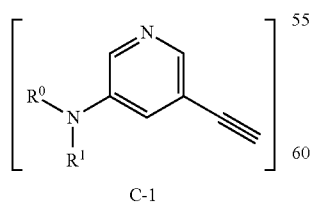

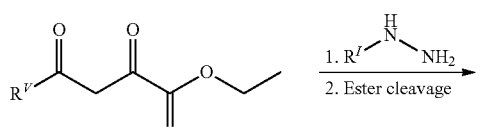

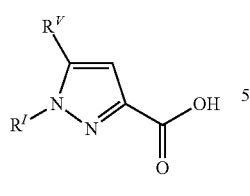

ED-2

Special pyrazole-5-carboxylic acids ED-2 may be prepared from the 1,3-diketones Z-3 as described in Reaction scheme 4 by cyclising with alkylhydrazines followed by basic ester cleavage. The 1,3-diketones Z-3 can be synthesised from the methylketones ED-4 by condensation with diethyloxalate. Depending on the ketones ED-4 and hydrazines $R^I NHNH_2$ used, optionally up to four regioisomers are formed with the reaction sequence described, from which the desired carboxylic acid ED-2 is isolated by chromatography.

Reaction scheme 5: A further possible method of preparing special pyrazolecarboxylic acids ED-2 (synthesis method B).

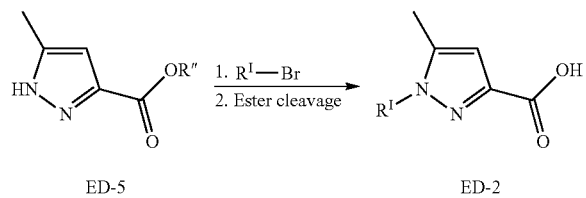

ED-5                                    ED-2

R″ = common ester protecting group, especially Me, tBu, Bn 3-methyl-pyrazolecarboxylic acids ED-2 may also be prepared as shown in Reaction scheme 5 by alkylation with alkylhalides and subsequent ester cleavage from the pyrazoles ED-5. The alkylhalides used are preferably chlorides, bromides and iodides. As the corresponding tautomer for ED-5 may optionally be present to some extent, the desired carboxylic acid ED-2 may be isolated from the mixture of the regioisomers by chromatography.

a) Method for Synthesising the Pyrazolecarboxylic Acid ED-2a (Synthesis Method A)

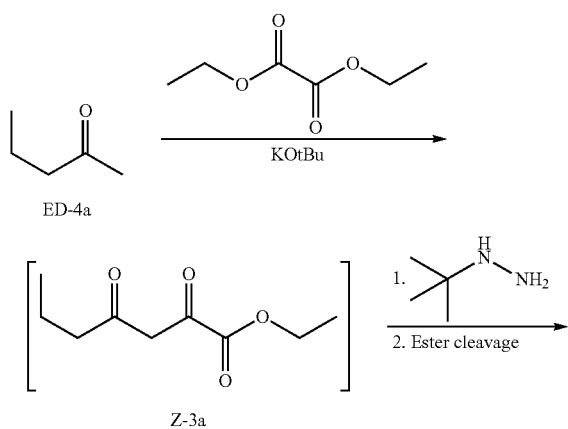

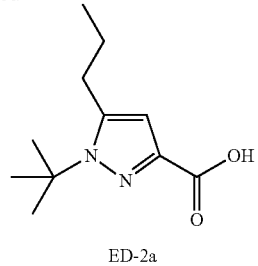

ED-2a

Methylpropylketone ED-4a (1.5 mL, 14.1 mmol) is placed in EtOH (70 mL), combined with diethyloxalate (2.3 mL, 17.0 mmol) and potassium-tert.-butoxide (1.73 g, 15.4 mmol) and stirred for 30 min at 75° C. Then the reaction mixture is cooled to RT, tert.-butylhydrazine hydrochloride (3.49 g, 18.0 mmol) is added and the mixture is stirred for 1.5 h at 75° C. The solvent is eliminated using the rotary evaporator, the residue is taken up in THF (15 mL), combined with aqueous LiOH solution (1 M, 21.0 mL) and stirred for 20 h at RT. The reaction mixture is diluted with $H_2O$ and the aqueous phase is extracted twice with DCM. The organic phases are discarded. The aqueous phase is acidified to pH 1 with hydrochloric acid and extracted five times with DCM. The combined organic phases are dried on $MgSO_4$, filtered and evaporated down using the rotary evaporator. The residue is taken up in a little DCM and purified by chromatography (DCM/MeOH=100:0 to 80:20). The product-containing fractions of ED-2a are combined and evaporated down using the rotary evaporator.

b) Method for Synthesising the Pyrazolecarboxylic Acid ED-2b (Synthesis Method B)

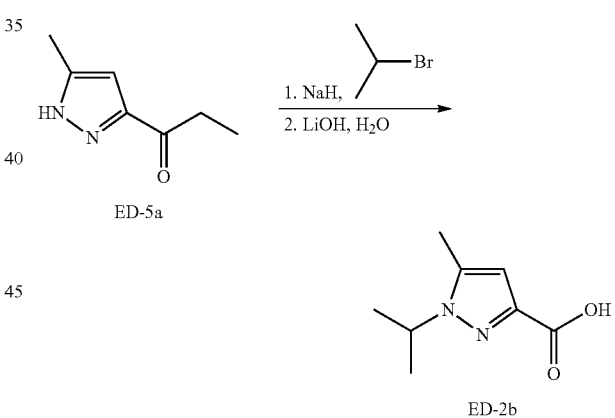

ED-5a (2.00 g, 14.3 mmol) in DMF (7 mL) is added dropwise to a suspension of NaH (694 mg, 60%, 17.4 mmol) in anhydrous DMF (8 mL) while cooling with ice and the mixture is slowly thawed to RT over 1 h. Then isopropyl bromide (2.7 mL, 28.8 mmol) is added and the mixture is stirred for 20 h at RT. The reaction mixture is mixed with a little water, then for saponification aqueous LiOH solution (414 mg in 3 mL $H_2O$) is added and the mixture is stirred for 2 h at 40° C. The reaction mixture is neutralised with hydrochloric acid, evaporated down to some extent using the rotary evaporator and the residue is purified by preparative RP-MPLC. The product-containing fractions of ED-2b (HPLC-MS: $t_{Ret.}$=0.00 min; MS (M−H)⁻=167) are combined and freeze-dried.

Analogously to these methods a) and b) further pyrazolecarboxylic acids ED-2 may be synthesised from the corresponding educts ED-4 or ED-5.

TABLE 2

Carboxylic acids ED-2 used for preparing the compounds of type I.

| # | Structure | Method |
|---|---|---|
| ED-2a | 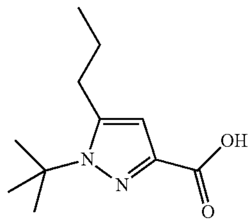 | synthesis method A |
| ED-2b | 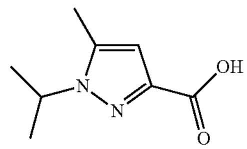 | synthesis method B |
| ED-2c | 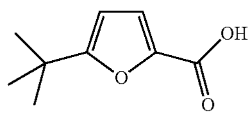 | commercially obtainable |
| ED-2d | 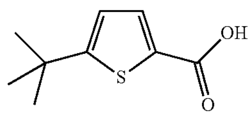 | commercially obtainable |
| ED-2e | 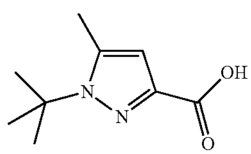 | commercially obtainable |
| ED-2f | 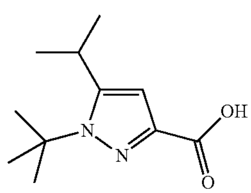 | commercially obtainable |
| ED-2g | 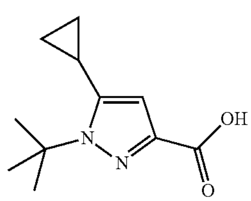 | commercially obtainable |
| ED-2h | | synthesis method A | c) Method for Synthesising the Furancarboxylic Acid Intermediate ED-2i (for Use in Synthesis Method 1A*)

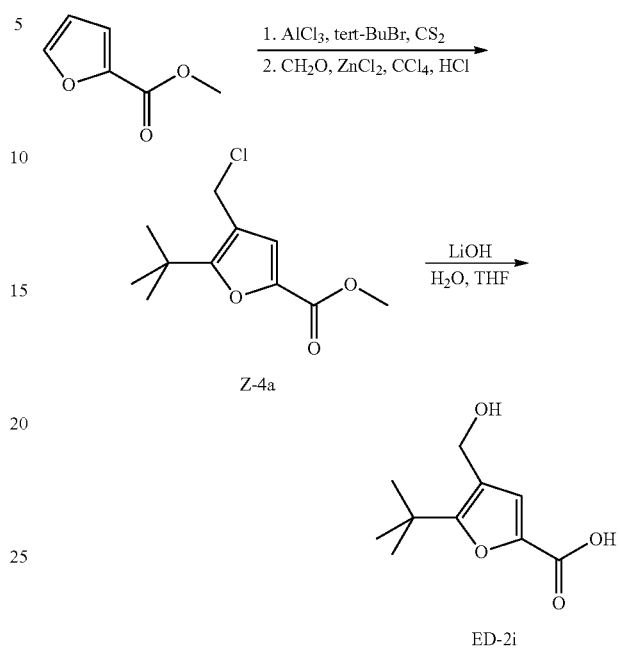

AlCl$_3$ (25.4 g, 190 mmol) is added batchwise to methyl furan-2-carboxylate (20.0 g, 159 mmol) and tert.-butylbromide (21.4 mL, 190 mmol) in CS$_2$ (200 mL) while cooling with ice and the mixture is stirred for 6 h at RT. The reaction mixture is poured onto ice water, mixed with conc. hydrochloric acid (25 mL) and stirred for 10 min. Then the aqueous phase is extracted 2× with 200 mL EA. The combined organic phase is dried on Na$_2$SO$_4$, filtered and evaporated down using the rotary evaporator. The methyl 5-tert.-butyl-furan-2-carboxylate thus obtained is used further without any additional purification steps.

Ethereal HCl solution (4 N, 200 mL) is added at RT to the resulting methyl 5-tert.-butyl-furan-2-carboxylate (10.0 g, 55.0 mmol), para-formaldehyde (9.88 g, 329 mmol) and ZnCl$_2$ (15.0 g, 110 mmol) in CCl$_4$ (200 mL) and the mixture is stirred for 4 d at RT. The reaction mixture is poured onto ice water and extracted twice with 200 mL EA. The combined organic phase is dried on Na$_2$SO$_4$, filtered and evaporated down using the rotary evaporator. The crude product is taken up in a little EA and purified by NP chromatography (PE/EA=98:2). The product-containing fractions of the 3-chloromethyl derivative Z-4a (methyl 5-tert-butyl-4-chlormethyl-furan-2-carboxylate) are combined and evaporated down using the rotary evaporator.

Aqueous LiOH solution (1 M, 35 mL) is added to the methyl ester Z-4a (3.02 g, 13.1 mmol) in THF (30 mL) and the reaction mixture is stirred for 30 h at RT. Then the mixture is evaporated down using the rotary evaporator and the aqueous residue is extracted twice with DCM (50 mL in each case). The combined organic phase is re-extracted once with sodium hydroxide solution (1 M, 50 mL). The combined aqueous phase is acidified with hydrochloric acid (6N) and extracted four times with DCM. The combined organic phase is dried on MgSO$_4$, filtered and evaporated down using the rotary evaporator. The carboxylic acid ED-2i (HPLC-MS: t$_{Ret}$=0.00 min; MS (M−H)$^-$=197) thus obtained is used further without any additional purification.

Carboxylic acid ED-2i may also be coupled to anilines A-1 and simultaneously substituted in the side chain by amines NHR'R", thus producing compounds A-2*. These may be reacted like A-2 to form compounds according to the invention (synthesis method 1A with modification 1A*)

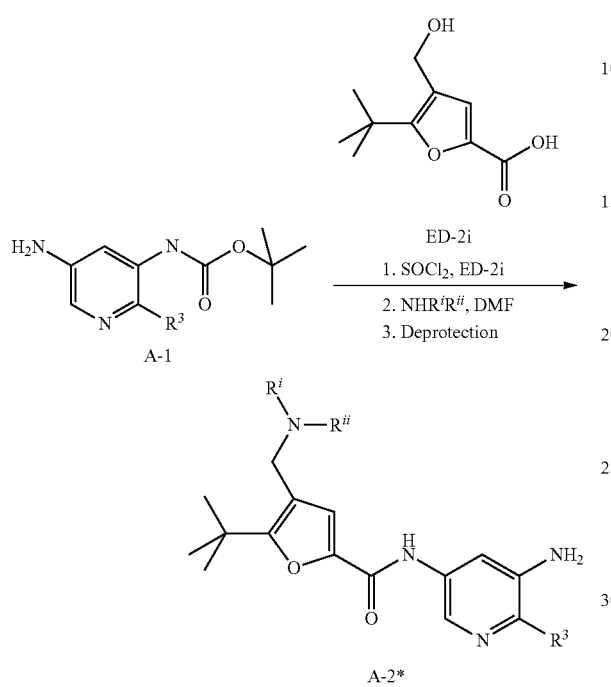

If instead of an amine NHR'R" an alcohol R'''OH, e.g. ethanol, is added or the reaction is carried out in an alcohol R'''OH, the corresponding furylmethylethers A-2** may be obtained.

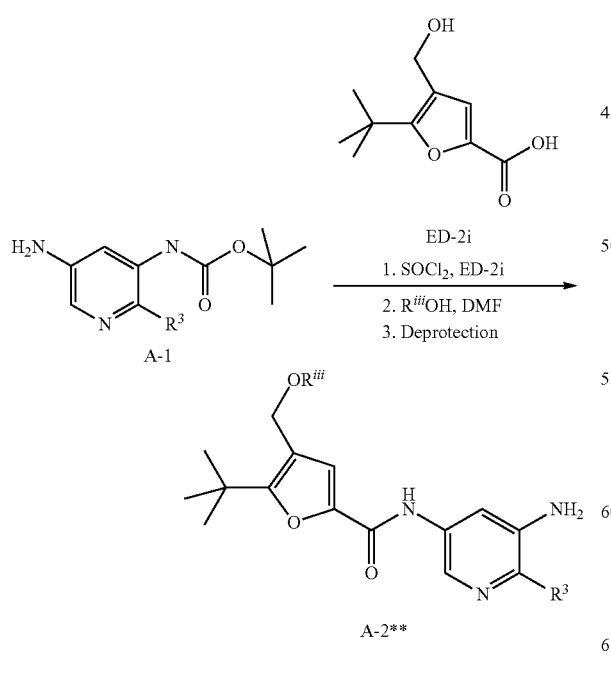

C. Preparation of the Type I Compounds According to the Invention a) Method for Synthesising A-1a

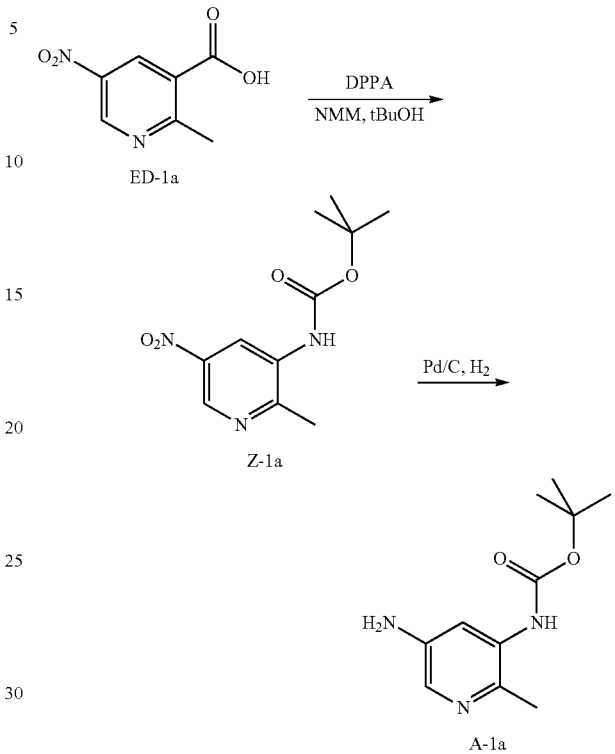

Step 1: Synthesis of Z-1a

ED-1a (15.6 g, 85.7 mmol) is placed in tert.-BuOH (300 mL), combined with DPPA (27 mL, 125 mmol) and NMM (12 mL, 108 mmol) and refluxed for 5 h. After cooling, saturated sodium chloride solution is added and the mixture is extracted several times with EA. The combined organic phases are washed with saturated sodium chloride solution, dried on $MgSO_4$, filtered and evaporated down using the rotary evaporator. The residue is taken up in water and freeze-dried. The resulting Z-1a (HPLC-MS: $t_{Ret.}$=1.73 min; MS $(M+H)^+$=254) is used without further purification.

Step 2: Synthesis of A-1a

Z-1a (15.1 g, 59.6 mmol) is placed in a hydrogenating reactor in MeOH (200 mL), combined with Pd/C (5%, 1.39 g) and stirred for 20 h under 5 bar hydrogen pressure at RT. Then the catalyst is filtered off, the residue is washed several times with MeOH and the filtrate is evaporated down using the rotary evaporator. The A-1a thus obtained (HPLC-MS: $t_{Ret.}$=1.11 min; MS $(M+H)^+$=224) is used further without any more purification.

b) Method of Synthesising the Aniline A-2a

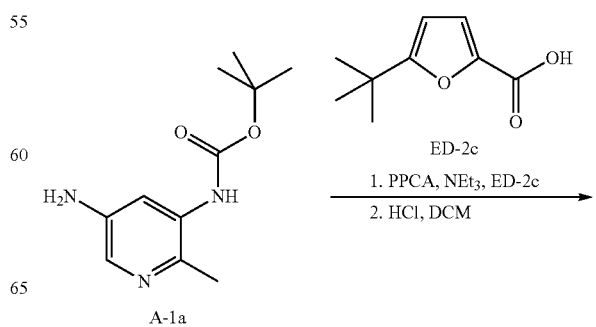

-continued

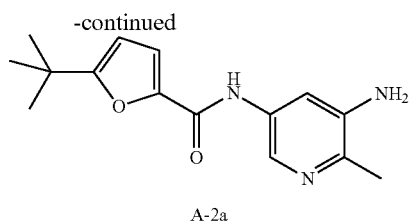

A-2a

PPCA (50% in EA, 7.5 mL, 13.0 mmol) is added dropwise at RT to A-1a (2.96 g, 13.2 mmol), ED-2c (2.07 g, 12.3 mmol) and NEt₃ (5 mL) in THF (20 mL) over 5 min and the reaction mixture is left for 3 d at RT with stirring. The reaction mixture is evaporated down using the rotary evaporator, the residue is taken up in a little DCM and purified by NP chromatography (DCM/MeOH=100:0 to 80:20). The product-containing fractions of the amide are combined and evaporated down using the rotary evaporator.

In order to cleave the Boc group the amide (1.67 g, 4.50 mmol) is placed in DCM (20 mL), combined with concentrated hydrochloric acid (2 mL) and stirred for 20 h at RT. Then the mixture is diluted with DCM and H₂O, the organic phase is separated off and extracted twice more with hydrochloric acid (8N). The combined aqueous phases are made alkaline with sodium hydroxide solution (8N) and extracted four times with DCM. The combined organic phases are dried on MgSO₄, filtered and evaporated down using the rotary evaporator. The resulting A-2a (HPLC-MS: $t_{Ret.}$=1.46 min; MS (M+H)⁺=274) is used further without any more purification.

c) Method of Synthesising the Azide A-3a

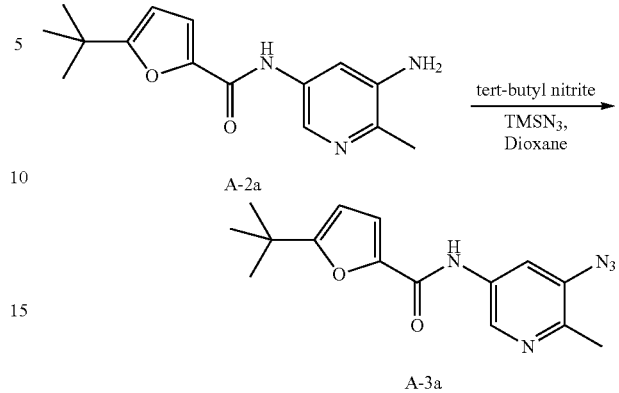

Trimethylsilyl azide (2 mL, 25.1 mmol) and tert.-butylnitrite (3.4 mL, 28.6 mmol) are added in several batches to A-2a (1.21 g, 4.41 mmol) in 1,4-dioxane (30 mL), while the reaction mixture is stirred first of all at RT and later at 55° C. for a total of 4 d. The reaction mixture is diluted with DCM and washed twice with saturated sodium hydrogen carbonate solution. The aqueous phase is extracted twice with DCM. The combined organic phases are dried on MgSO₄, filtered and evaporated down using the rotary evaporator. The residue is purified by NP chromatography (cyclohexane/EA=85:15 to 0:100). The product-containing fractions of A-3a (HPLC-MS: $t_{Ret.}$=1.89 min; MS (M+H)⁺=300) are combined and evaporated down using the rotary evaporator.

Analogously to methods b) and c) further anilines A-2 or azides A-3 may be synthesised from the mono-Boc-protected bis-anilines A-1.

TABLE 3

Anilines A-2 or azides A-3 used to prepare the Example compounds I

| # | Structure | $t_{Ret.}$ (HPLC) [min] | MS (M + H)⁺ |
|---|-----------|------------------------|-------------|
| A-2a | 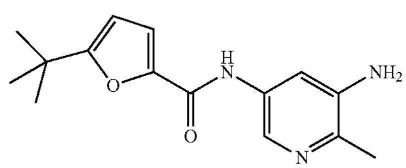 [SMILES: Cc1ncc(NC(=O)c2ccc(C(C)(C)C)o2)cc1N] | 1.46 | 274 |
| A-3a | 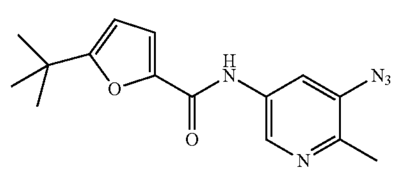 [SMILES: Cc1ncc(NC(=O)c2ccc(C(C)(C)C)o2)cc1N=[N+]=[N-]] | 1.89 | 300 |
| A-2b | 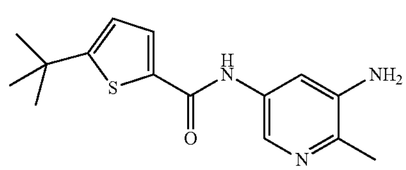 [SMILES: Cc1ncc(NC(=O)c2ccc(C(C)(C)C)s2)cc1N] | 1.57 | 290 |

TABLE 3-continued

Anilines A-2 or azides A-3 used to prepare the Example compounds I

| # | Structure | $t_{Ret.}$ (HPLC) [min] | MS (M + H)+ |
|---|---|---|---|
| A-3b | 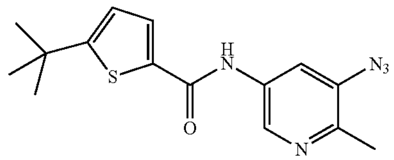 [SMILES: Cc1ncc(NC(=O)c2ccc(C(C)(C)C)s2)cc1N=[N+]=[N-]] | not determined | 316 |
| A-2c | 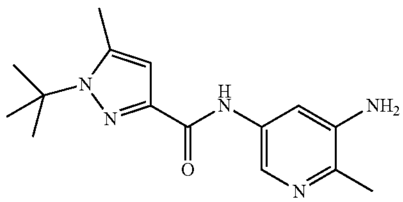 [SMILES: Cc1ncc(NC(=O)c2cc(C)n(C(C)(C)C)n2)cc1N] | 1.37 | 288 |
| A-3c | 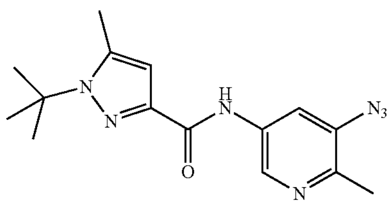 [SMILES: Cc1ncc(NC(=O)c2cc(C)n(C(C)(C)C)n2)cc1N=[N+]=[N-]] | not determined | 314 |
| A-2d | 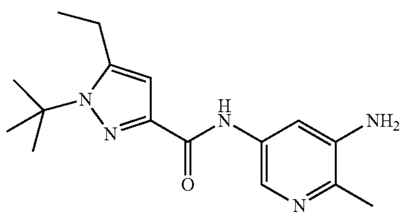 [SMILES: CCc1cc(C(=O)Nc2cnc(C)c(N)c2)nn1C(C)(C)C] | 1.60 | 302 |
| A-3d | 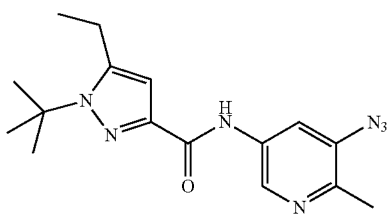 [SMILES: CCc1cc(C(=O)Nc2cnc(C)c(N=[N+]=[N-])c2)nn1C(C)(C)C] | 2.01 | 328 |
| A-2e | 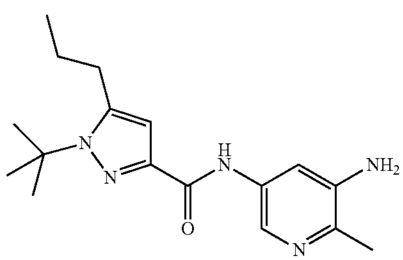 [SMILES: CCCc1cc(C(=O)Nc2cnc(C)c(N)c2)nn1C(C)(C)C] | 1.80 | 316 |
| A-3e | 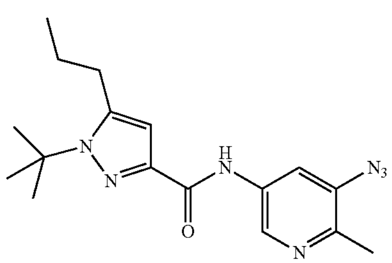 [SMILES: CCCc1cc(C(=O)Nc2cnc(C)c(N=[N+]=[N-])c2)nn1C(C)(C)C] | 2.15 | 342 |

TABLE 3-continued

Anilines A-2 or azides A-3 used to prepare the Example compounds I

| # | Structure | t_Ret. (HPLC) [min] | MS (M + H)+ |
|---|---|---|---|
| A-2f | 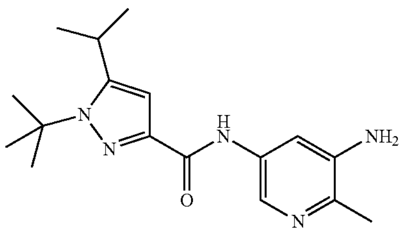 [SMILES: Cc1ncc(NC(=O)c2cc(C(C)C)n(C(C)(C)C)n2)cc1N] | 1.64 | 316 |
| A-3f | 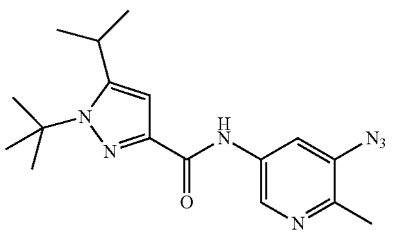 [SMILES: Cc1ncc(NC(=O)c2cc(C(C)C)n(C(C)(C)C)n2)cc1N=[N+]=[N-]] | not determined | 342 |
| A-2g | 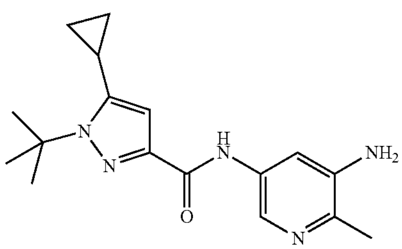 [SMILES: Cc1ncc(NC(=O)c2cc(C3CC3)n(C(C)(C)C)n2)cc1N] | 1.58 | 314 |
| A-3g | 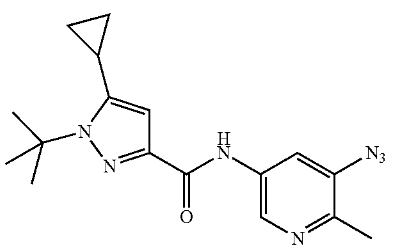 [SMILES: Cc1ncc(NC(=O)c2cc(C3CC3)n(C(C)(C)C)n2)cc1N=[N+]=[N-]] | not determined | 340 |
| A-2h | 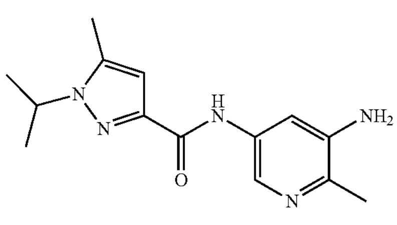 [SMILES: Cc1ncc(NC(=O)c2cc(C)n(C(C)C)n2)cc1N] | 1.23 | 274 |
| A-3h | | 1.73 | 300 | d) Method of Synthesising Example Compound I-1

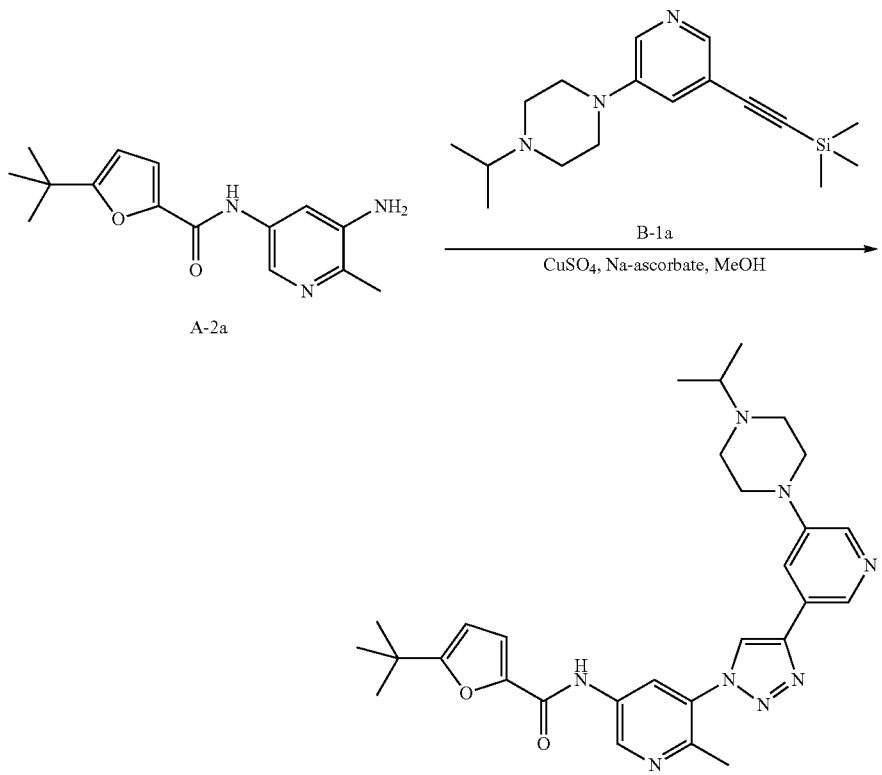

B-1a (124 mg, 410 μmol) and KF (35.7 mg, 614 μmol) are placed in MeOH (3 mL) and the mixture is stirred for 1 h at RT. After the TMS group has been cleaved completely, the azide A-3a (60.4 mg, 202 μmol), sodium ascorbate (33.1 mg, 167 μmol in $H_2O$) and $CuSO_4$ solution (6.3 μL, 0.8 M in $H_2O$) are added successively and the mixture is stirred for 2 d at 40° C. The reaction mixture is evaporated down using the rotary evaporator, the residue is taken up in a little DMF/MeOH and purified by preparative RP-HPLC. The product-containing fractions of I-1 (HPLC-MS: $t_{Ret.}$=1.92 min; MS $(M+H)^+$= 529) are freeze-dried.

Analogously to methods a) to d) described above for synthesising the Example compound I-1 (synthesis method 1A), further compounds I-2 to I-50 according to the invention may be synthesised from the anilines A-1, the carboxylic acids ED-2 and the TMS-protected alkynes B-1 (cf. Table 4). In addition, other examples compounds of type I may be prepared using the methods described.

TABLE 4

| | Example compounds of type I | | |
|---|---|---|---|
| # | Structure | $t_{Ret.}$ (HPLC) [min] | MS $(M + H)^+$ |
| I-1 | | 1.92 | 529 |

TABLE 4-continued
Example compounds of type I
| # | Structure | $t_{Ret.}$ (HPLC) [min] | MS $(M + H)^+$ |
|---|---|---|---|
| I-2 | 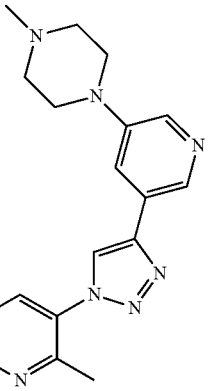 | 1.74 | 501 |
| I-3 | 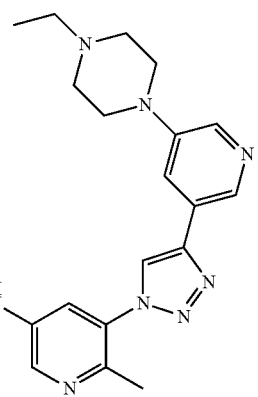 | 1.85 | 515 |
| I-4 | 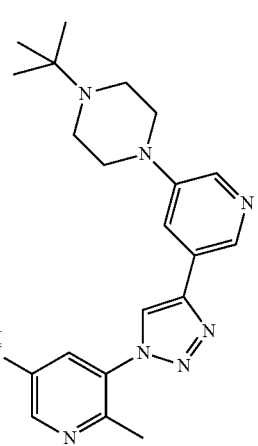 | 1.99 | 543 |

TABLE 4-continued
Example compounds of type I
| # | Structure | t_Ret. (HPLC) [min] | MS (M + H)+ |
|---|---|---|---|
| I-5 | 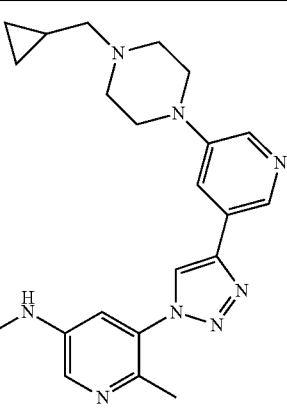 | 1.94 | 541 |
| I-6 | 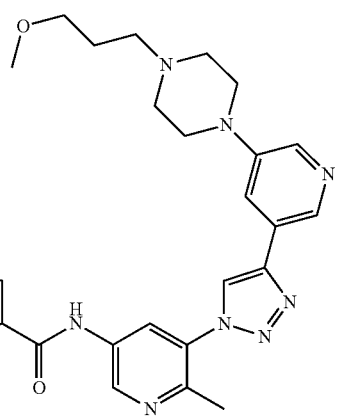 | 1.82 | 559 |
| I-7 | 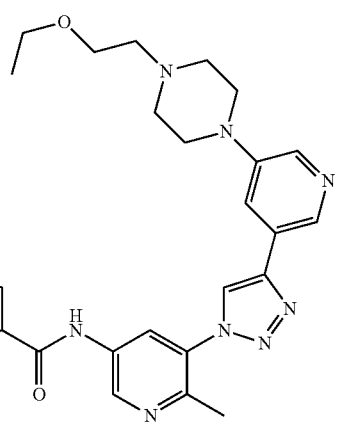 | 1.86 | 559 |

TABLE 4-continued
Example compounds of type I
| # | Structure | t_Ret. (HPLC) [min] | MS (M + H)+ |
|---|---|---|---|
| I-8 | 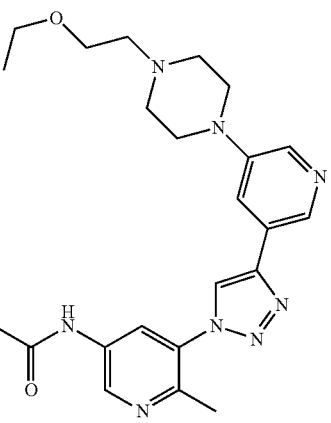 | 1.91 | 575 |
| I-9 | 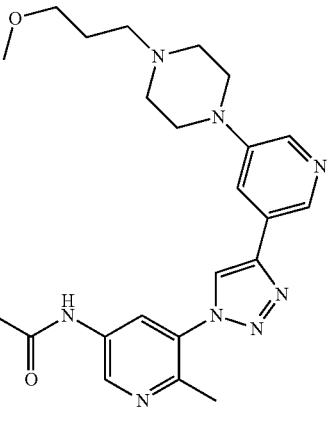 | 1.91 | 575 |
| I-10 | 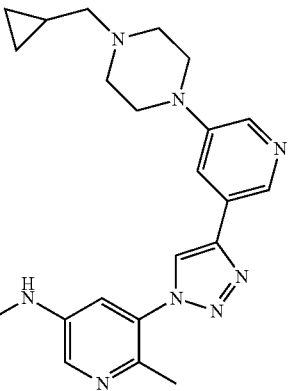 | 2.03 | 557 |

TABLE 4-continued

Example compounds of type I

| # | Structure | $t_{Ret.}$ (HPLC) [min] | MS $(M + H)^+$ |
|---|---|---|---|
| I-11 | 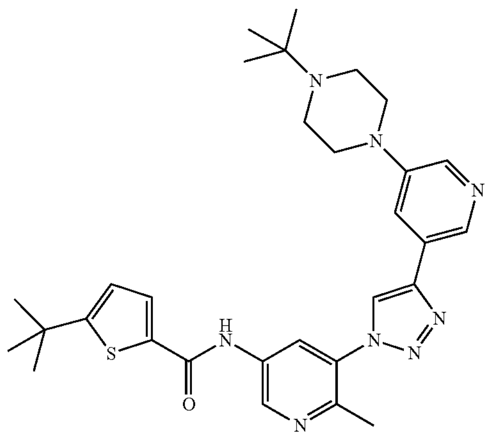 [SMILES: Cc1ncc(NC(=O)c2ccc(C(C)(C)C)s2)cc1-n1cc(-c2cncc(N3CCN(C(C)(C)C)CC3)c2)nn1] | 2.14 | 559 |
| I-12 | 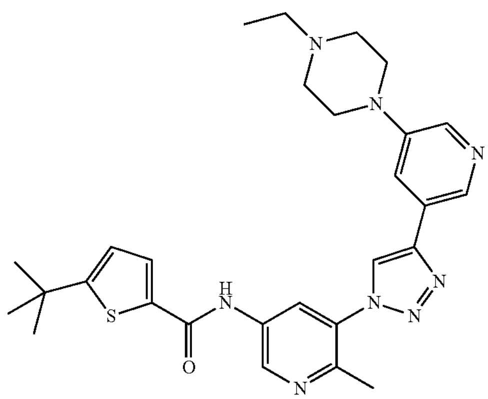 [SMILES: CCN1CCN(c2cncc(-c3cn(-c4cc(NC(=O)c5ccc(C(C)(C)C)s5)cnc4C)nn3)c2)CC1] | 1.91 | 531 |
| I-13 | 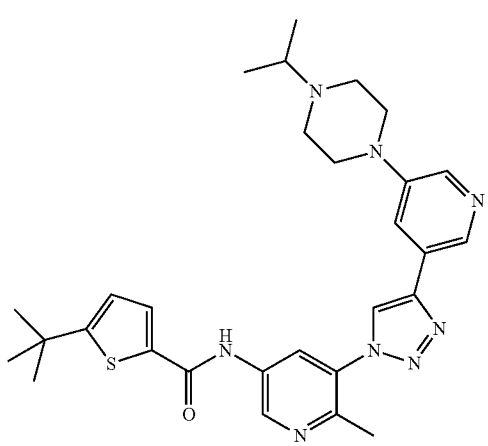 [SMILES: Cc1ncc(NC(=O)c2ccc(C(C)(C)C)s2)cc1-n1cc(-c2cncc(N3CCN(C(C)C)CC3)c2)nn1] | 2.05 | 545 |

TABLE 4-continued
Example compounds of type I
| # | Structure | t_Ret. (HPLC) [min] | MS (M + H)+ |
|---|---|---|---|
| I-14 | 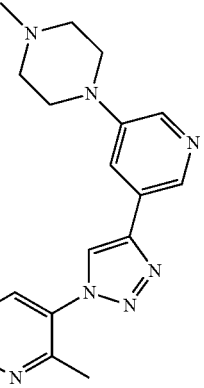 | 1.87 | 517 |
| I-15 | 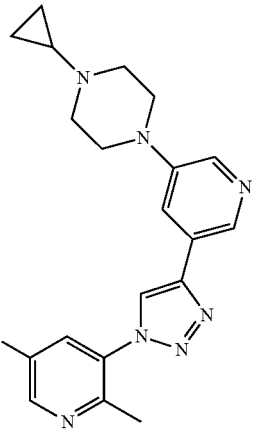 | 1.95 | 541 |
| I-16 | 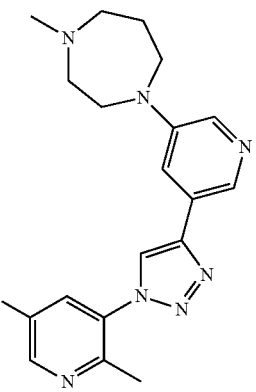 | 1.75 | 529 |

TABLE 4-continued
Example compounds of type I
| # | Structure | t$_{Ret.}$ (HPLC) [min] | MS (M + H)$^+$ |
|---|---|---|---|
| I-17 | 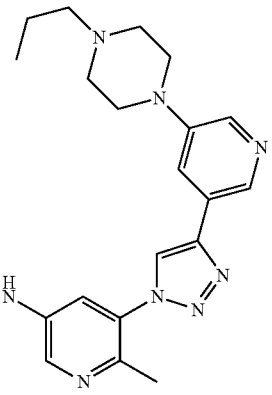 | 2.04 | 543 |
| I-18 | 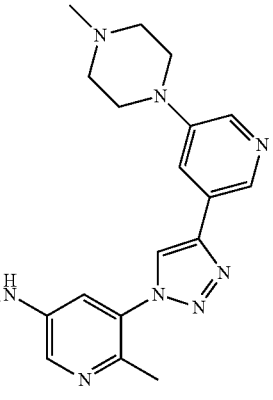 | 1.71 | 515 |
| I-19 | 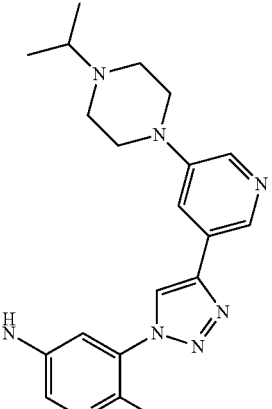 | 1.89 | 543 |

TABLE 4-continued
Example compounds of type I
| # | Structure | $t_{Ret.}$ (HPLC) [min] | MS $(M + H)^+$ |
|---|---|---|---|
| I-20 | 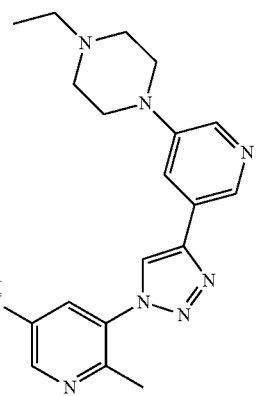 | 1.76 | 529 |
| I-21 | 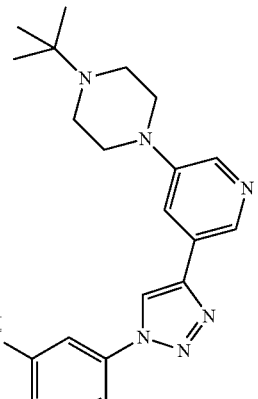 | 1.97 | 557 |
| I-22 | 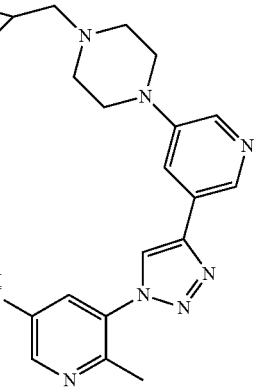 | 1.92 | 555 |

TABLE 4-continued
Example compounds of type I
| # | Structure | $t_{Ret.}$ (HPLC) [min] | MS $(M + H)^+$ |
|---|---|---|---|
| I-23 | 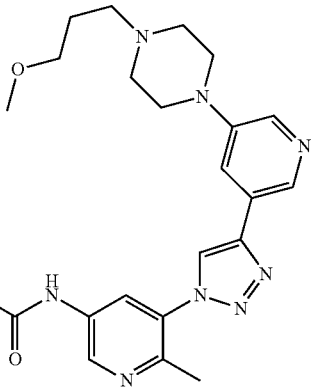 | 1.79 | 573 |
| I-24 | 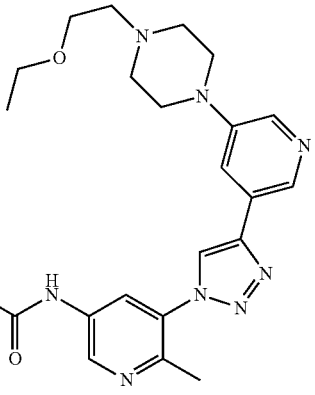 | 1.83 | 573 |
| I-25 | 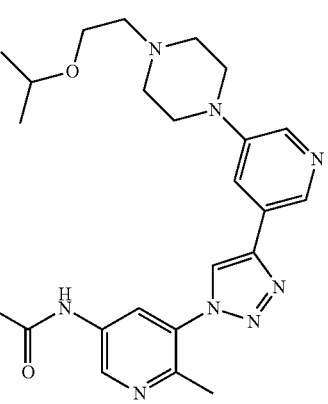 | 2.00 | 587 |

TABLE 4-continued
Example compounds of type I
| # | Structure | t$_{Ret.}$ (HPLC) [min] | MS (M + H)$^+$ |
|---|---|---|---|
| I-26 | 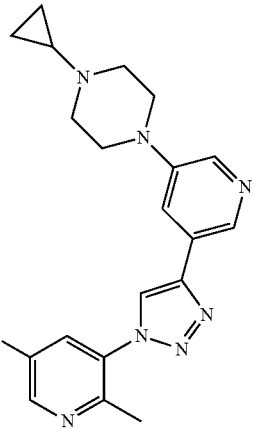 | 1.80 | 555 |
| I-27 | 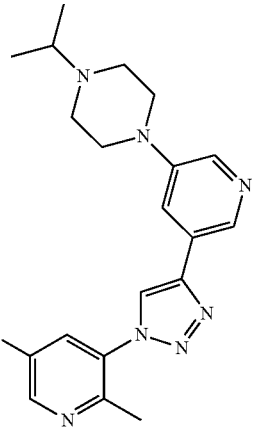 | 1.80 | 557 |
| I-28 | 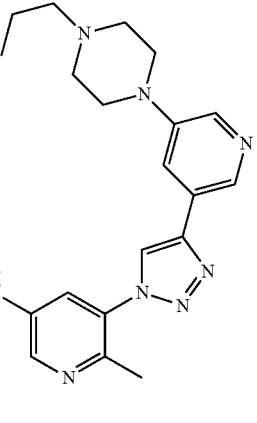 | 2.05 | 557 |

TABLE 4-continued
Example compounds of type I
| # | Structure | t_Ret. (HPLC) [min] | MS (M + H)+ |
|---|---|---|---|
| I-29 | 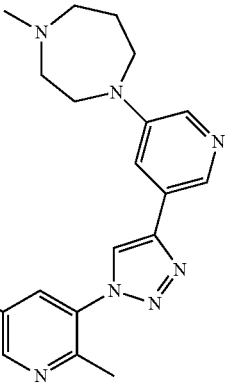 | 2.00 | 557 |
| I-30 | 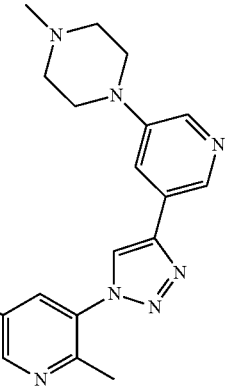 | 1.84 | 529 |
| I-31 | 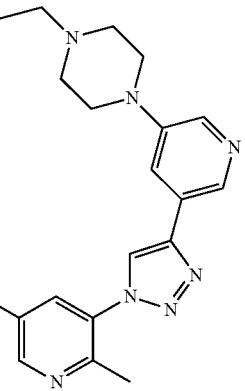 | 1.90 | 543 |

TABLE 4-continued
Example compounds of type I
| # | Structure | t_Ret. (HPLC) [min] | MS (M + H)+ |
|---|---|---|---|
| I-32 | 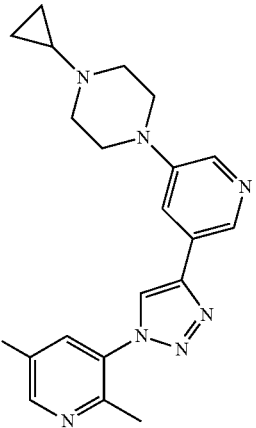 | 2.14 | 569 |
| I-33 | 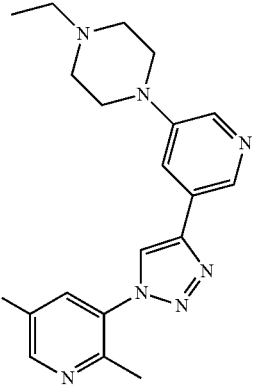 | 2.05 | 557 |
| I-34 | 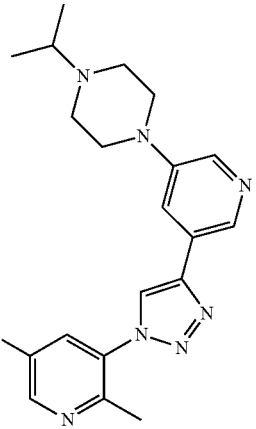 | 2.13 | 571 |

TABLE 4-continued

Example compounds of type I

| # | Structure | $t_{Ret.}$ (HPLC) [min] | MS (M + H)⁺ |
|---|---|---|---|
| I-35 | 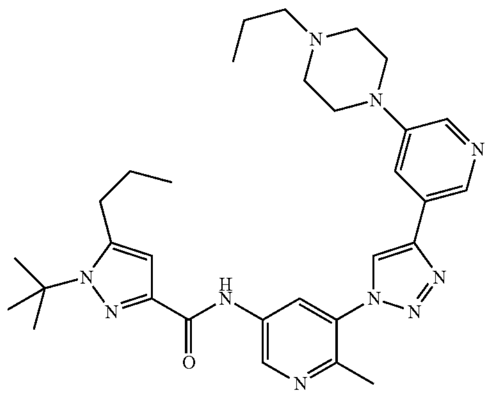 [SMILES: CCCc1cc(C(=O)Nc2cnc(C)c(-n3cc(-c4cncc(N5CCN(CCC)CC5)c4)nn3)c2)nn1C(C)(C)C] | 2.17 | 571 |
| I-36 | 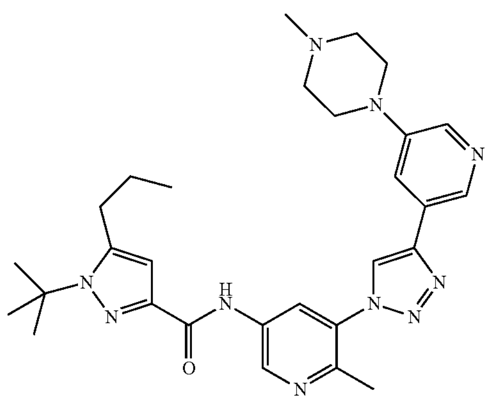 [SMILES: CCCc1cc(C(=O)Nc2cnc(C)c(-n3cc(-c4cncc(N5CCN(C)CC5)c4)nn3)c2)nn1C(C)(C)C] | 1.97 | 543 |
| I-37 | 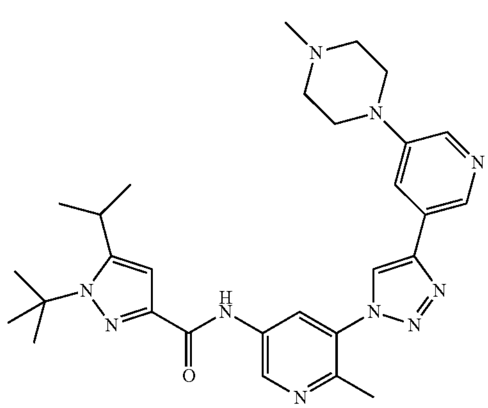 [SMILES: Cc1ncc(NC(=O)c2cc(C(C)C)n(C(C)(C)C)n2)cc1-n1cc(-c2cncc(N3CCN(C)CC3)c2)nn1] | 1.91 | 543 |

TABLE 4-continued
Example compounds of type I
| # | Structure | t_Ret. (HPLC) [min] | MS (M + H)+ |
|---|---|---|---|
| I-38 | 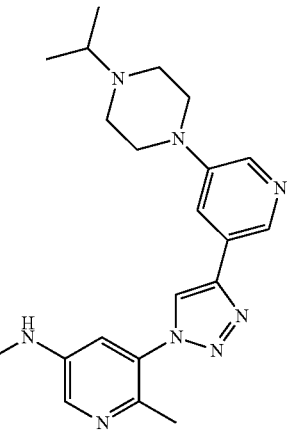 | 2.07 | 571 |
| I-39 | 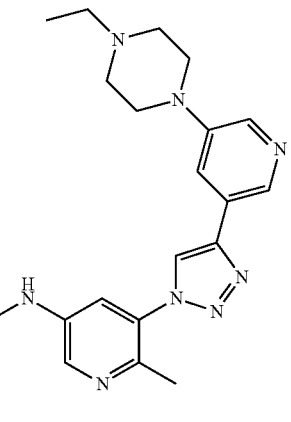 | 1.98 | 557 |
| I-40 | 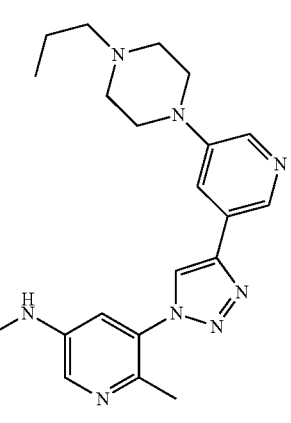 | 2.10 | 571 |

TABLE 4-continued
Example compounds of type I
| # | Structure | t_Ret. (HPLC) [min] | MS (M + H)+ |
|---|---|---|---|
| I-41 | 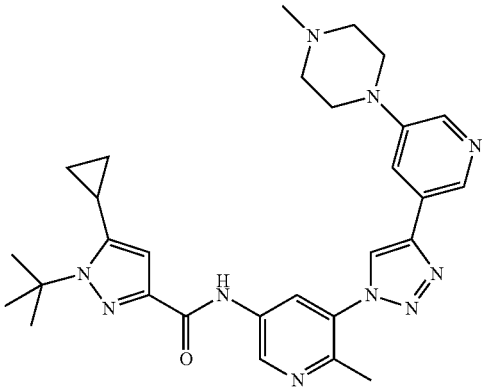 [SMILES: Cc1ncc(NC(=O)c2cc(C3CC3)n(C(C)(C)C)n2)cc1-n1cc(-c2cncc(N3CCN(C)CC3)c2)nn1] | 1.85 | 541 |
| I-42 | 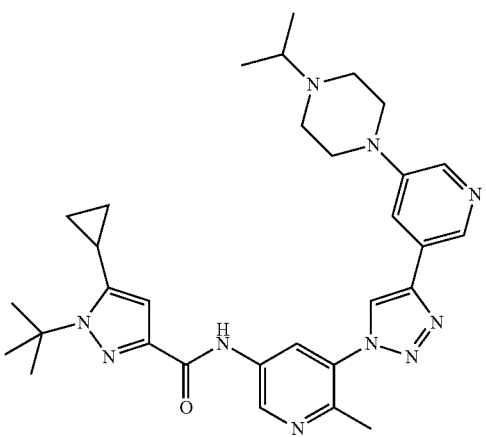 [SMILES: Cc1ncc(NC(=O)c2cc(C3CC3)n(C(C)(C)C)n2)cc1-n1cc(-c2cncc(N3CCN(C(C)C)CC3)c2)nn1] | 2.02 | 569 |
| I-43 | 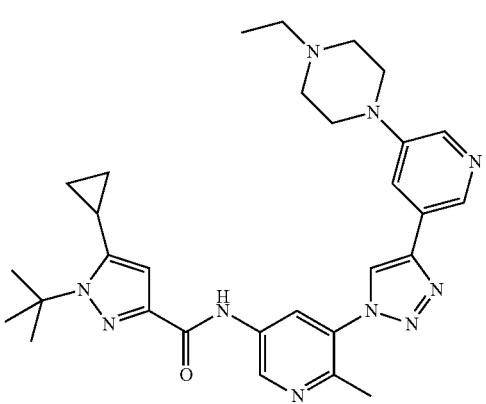 [SMILES: CCN1CCN(c2cncc(-c3cn(-c4cc(NC(=O)c5cc(C6CC6)n(C(C)(C)C)n5)cnc4C)nn3)c2)CC1] | 2.08 | 555 |

TABLE 4-continued
Example compounds of type I
| # | Structure | $t_{Ret.}$ (HPLC) [min] | MS $(M + H)^+$ |
|---|---|---|---|
| I-44 | 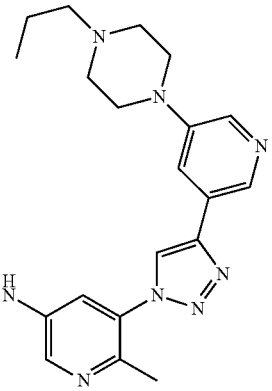 | 2.06 | 569 |
| I-45 | 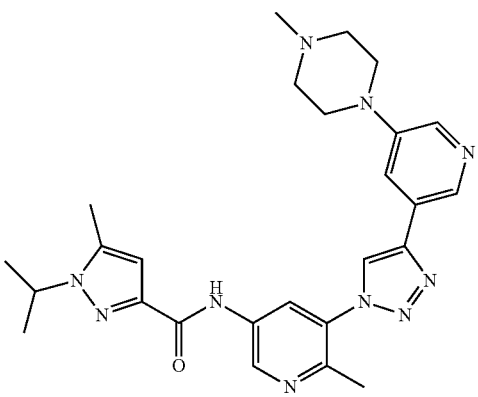 [SMILES: Cc1ncc(NC(=O)c2cc(C)n(C(C)C)n2)cc1-n1cc(-c2cncc(N3CCN(C)CC3)c2)nn1] | 1.62 | 501 |
| I-46 | 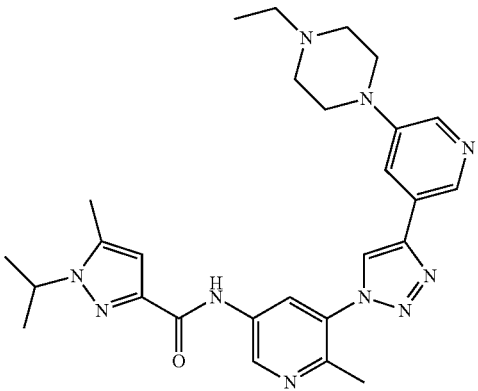 [SMILES: CCN1CCN(c2cncc(-c3cn(-c4cc(NC(=O)c5cc(C)n(C(C)C)n5)cnc4C)nn3)c2)CC1] | 1.71 | 515 |

TABLE 4-continued
Example compounds of type I
| # | Structure | t_Ret. (HPLC) [min] | MS (M + H)+ |
|---|---|---|---|
| I-47 | 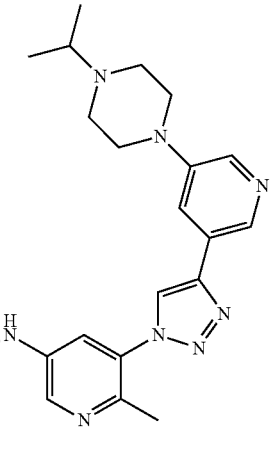 | 1.80 | 529 |
| I-48 | 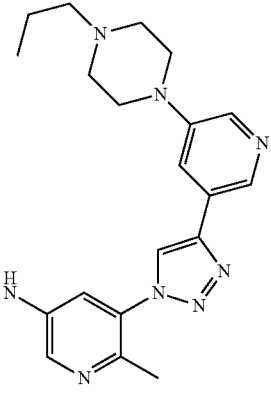 | 1.84 | 529 |
| I-49 | 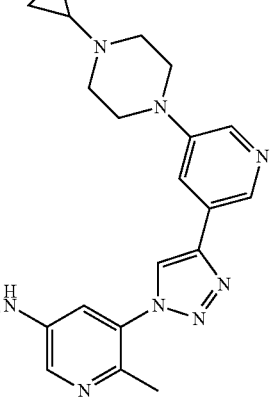 | 1.80 | 527 |

TABLE 4-continued

Example compounds of type I

| # | Structure | $t_{Ret.}$ (HPLC) [min] | MS $(M + H)^+$ |
|---|---|---|---|
| I-50 | 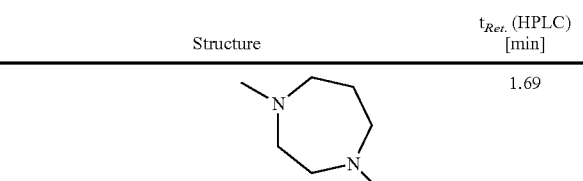 | 1.69 | 515 |

Further References Relating to Reaction Schemes 1 to 5 and Example Compounds of Types I and II:

Where there is an indication in the foregoing reaction methods to the effect that other similar compounds may be prepared analogously using the reaction specifically described, this also includes the possibility that there may be the need for variations in the reaction temperature, length of reaction, nature of purification (equipment, gradient), any equivalents to be used, the protecting groups used, etc., which the skilled man will immediately recognise and he will readily adapt the described reaction accordingly.

For amide coupling reactions, methods of activating the carboxylic acids are used which are known from the literature. Thus, for example, the acids may be converted with $SOCl_2$, oxalyl chloride/DMF or the GHOSEZ reagent (1-chloro-N,N,2-trimethylpropenylamine) into the acid chlorides, which are reacted with the corresponding amines, with the addition of an auxiliary base such as for example TEA, DIPEA, pyridine or other common organic bases, to obtain the amides. Alternatively, the carboxylic acids may be activated with special coupling reagents such as for example HATU, TBTU, DCC, EDC, PyBOP, CDI, PPCA and other reagents known from the literature and reacted with amines and auxiliary bases as described above to obtain the amides.

The group —$NR^0R^1$ in type I and type II compounds according to the invention may optionally be modified in other reaction steps not shown in the Schemes to form other groups —$NR^0R^1$, thus obtaining further compounds I and II according to the invention. These reaction steps may be reactions of substitution, alkylation, acylation or addition.

Pyridylalkynes C-1 may be prepared, using methods known from the literature, from the corresponding pyridyl-halides by a palladium-catalysed SONOGASHIRA cross-coupling reaction with trimethylsilylacetylene in the presence of copper(I)iodide. The trimethylsilyl-protected alkynes thus obtained are reacted in situ by cleavage of the trimethysilyl group with $K_2CO_3$ or KF to form the terminal alkynes. Alternatively alkynes C-1 may also be prepared from the corresponding pyridylcarbaldehydes by reaction according to BESTMANN-OHIRA. The pyridylcarbaldehydes needed for this may be synthesised by methods known from the literature, e.g. by VILSMAIER-HAACK formylation of the corresponding heteroaromatic groups.

In addition, reference is made to the following publications regarding the synthesis of other educt components:

WO 2004/050642, WO 2005/056535, WO 2005/090333, WO 2005/115991, US 2006/100204, WO 2008/003770, WO 2009/003999, WO 2009/003998, WO 2008/089034, WO 2007/056016, WO 2007/075896, WO 2008/021388, WO 2005/023761

The following Examples describe the biological activity of the compounds according to the invention without restricting the invention to these Examples.

Compounds of general formula (1) are characterised by their many possible applications in the therapeutic field. Particular mention should be made of those applications in which the inhibition of specific signal enzymes, particularly the inhibiting effect on the proliferation of cultivated human tumour cells but also on the proliferation of other cells such as endothelial cells, for example, are involved.

Kinase Test B-Raf (V600E)

In a dilution series 10 µL/well of test substance solution are placed in a multiwell plate. The dilution series is selected so that generally a range of concentrations of 2 µM to 0.119 nM or 0.017 nM is covered. If necessary the initial concentration of 2 µM is changed to 50 µM, 10 µM, 0.4 µM or 0.2857 µM and further dilution is carried out accordingly. The final concentration of DMSO is 5%. 10 µL/well of the B-Raf (V600E)-kinase solution are pipetted in (containing 0.5 ng B-Raf (V600E)-kinase, e.g. from Upstate) in 20 mM tris-HCl pH 7.5, 0.1 mM EDTA, 0.1 mM EGTA, 0.286 mM sodium orthovanadate, 10% glycerol, 1 mg/mL bovine serum albumin, 1 mM dithiothreitol) and the mixture is incubated for 1 h at RT with shaking. The kinase reaction is started by the addition of 20 µL/well ATP solution [final concentration: 250 µM ATP, 30 mM tris-HCl pH 7.5, 0.02% Brij, 0.2 mM sodium orthovanadate, 10 mM magnesium acetate, 0.1 mM EGTA, phosphatase cocktail (Sigma, # P2850, dilution recommended by the manufacturer)] and 10 µL/well MEK1 solution [containing 50 ng biotinylated MEK1 (prepared from purified MEK1 according to standard procedure, e.g. with EZ-Link Sulpho-NHS-LC-Biotin reagent, Pierce, #21335)] and carried out for 60 min at RT with constant shaking. The reaction is stopped by the addition of 12 µL/well of a 100 mM EDTA solution and incubation is continued for a further 5 min. 55 µL/well of the reaction solution are transferred into a streptavidin-coated plate (e.g. Streptawell HighBond, Roche, #11989685001)

and gently shaken for 1 h at RT in order to bind biotinylated MEK1 to the plate. After elimination of the liquid the plate is washed five times with 200 μL/well of 1×PBS and 100 μL/well solution of primary antibody plus europium-labelled secondary antibody [Anti Phospho-MEK (Ser217/221), Cell Signaling, #9121 and Eu-N1 labelled goat-anti-rabbit antibody, Perkin Elmer, # AD0105] is added, the primary antibody is diluted 1:2000 and the secondary antibody is diluted to 0.4-0.5 μg/mL in Delfia Assay Buffer (Perkin Elmer, #1244-111). After 1 h shaking at RT the solution is poured away and washed five times with 200 μL/well Delfia Wash Buffer (Perkin Elmer, #4010-0010/#1244-114). After the addition of 200 μL/well Enhancement Solution (Perkin Elmer, #4001-0010/#1244-105) the mixture is shaken for 10 min at RT and then measured in a Wallac Victor using the program "Delfia Time Resolved Fluorescence (Europium)". $IC_{50}$ values are obtained from these dosage-activity curves using a software program (GraphPadPrizm).

The $IC_{50}$ values of the example compounds determined using the above assay are shown in Table 5.

TABLE 5

| # | B-RAF $IC_{50}$ (1 h) [nM] |
|---|---|
| I-1 | 4 |
| I-2 | 2 |
| I-3 | 3 |
| I-4 | 4 |
| I-5 | 3 |
| I-6 | 5 |
| I-7 | 5 |
| I-8 | 8 |
| I-9 | 7 |
| I-10 | 6 |
| I-11 | 6 |
| I-12 | 3 |
| I-13 | 5 |
| I-14 | 2 |
| I-15 | 20 |
| I-16 | 9 |
| I-17 | 10 |
| I-18 | 8 |
| I-19 | 8 |
| I-20 | 7 |
| I-21 | 9 |
| I-22 | 11 |
| I-23 | 14 |
| I-24 | 16 |
| I-25 | 16 |
| I-26 | 55 |
| I-27 | 12 |
| I-28 | 7 |
| I-29 | 19 |
| I-30 | 15 |
| I-31 | 12 |
| I-32 | 71 |
| I-33 | 16 |
| I-34 | 23 |
| I-35 | 22 |
| I-36 | 18 |
| I-37 | 17 |
| I-38 | 29 |
| I-39 | 25 |
| I-40 | 26 |
| I-41 | 16 |
| I-42 | 22 |
| I-43 | 22 |
| I-44 | 30 |
| I-45 | 9 |
| I-46 | 6 |
| I-47 | 6 |
| I-48 | 8 |
| I-49 | 22 |
| I-50 | 5 |

Measurement of the Inhibition of the Proliferation of Cultivated Human Melanoma Cells (SK-MEL-28, B-RAF$^{V600E}$ Mutated)

For measuring the proliferation of cultivated human tumour cells, cells of the melanoma cell line SK-MEL-28 [from American Type Culture Collection (ATCC)] are cultivated in MEM medium, supplemented with 10% foetal calf serum, 2% sodium bicarbonate, 1 mM sodium pyruvate, 1% non-essential amino acids (e.g. from Cambrex, # BE13-114E) and 2 mM glutamine. SK-MEL-28 cells are placed in 96-well flat bottomed dishes in a density of 2500 cells per well in supplemented MEM medium (see above) and incubated overnight in an incubator (at 37° C. and 5% $CO_2$). The active substances are added to the cells in different concentrations, so that a concentration range of 50 μM to 3.2 nM is covered. If necessary the initial concentration of 50 μM is changed to 10 μM or 2 μM and further dilution is carried out accordingly (up to 0.6 nM or 0.12 nM). After an incubation period of a further 72 h 20 μL AlamarBlue reagent (Serotec Ltd., # BUF012B) are added to each well and the cells are incubated for a further 3-6 h. The colour change of the AlamarBlue reagent is determined in a fluorescence spectrophotometer (e.g. Gemini, Molecular Devices). $EC_{50}$ values are calculated using a software program (Graph Pad Prizm).

All the example compounds I-1 to I-44 exhibit a good to very good activity in this cellular SK-MEL-28 assay, i.e. an $EC_{50}$ value of less than 300 nM, generally less than 200 nM. Example compounds I-45 to I-50 exhibit a range of $EC_{50}$ values of 150-450 nM in the cellular SK-MEL-28 assay.

Measurement of the Inhibition of the Proliferation of Cultivated Human Melanoma Cells (A375, B-RAF$^{V600E}$ Mutated)

For measuring the proliferation of cultivated human tumour cells, cells of the melanoma cell line A375 [from the American Type Culture Collection (ATCC)] are cultivated in DMEM medium, supplemented with 10% foetal calf serum and 2% sodium bicarbonate. Test substances are tested on A375 cells according to the procedure described for SK-MEL-28 cells (see above), but seeding them at 5000 cells per well.

All the example compounds I-1 to I-44 exhibit a good to very good activity in the cellular A375 assay, i.e. an $EC_{50}$ value of less than 150 nM, generally less than 100 nM. Example compounds I-45 to I-50 exhibit a range of $EC_{50}$ values of 400-700 nM in the cellular A375 assay.

The active substances are characterised in that they have a significantly lower antiproliferative activity on cell lines which have no B-RAF mutation. Thus, for example, example compounds I-1 to I-50 have an $EC_{50}$ value on melanoma cells (e.g. A375) without a B-Raf V600E mutation which is generally higher than that of B-RAF mutated melanoma cells (e.g. A375) by at least a factor of 10.

The $EC_{50}$ value of the phospho-ERK reduction and the $EC_{50}$ value of the antiproliferative activity in B-RAF mutated cell lines correlate well with cellular selectivity of the active substances.

Measurement of the Reduction of the Phospho-ERK Signal in Cultivated Human Melanoma Cells (SK-MEL-28, B-RAF$^{V600E}$ Mutated)

To measure the reduction in the phospho-ERK signal of cultivated human tumour cells, cells of the melanoma cell line SK-MEL-28 [from the American Type Culture Collection (ATCC)] in MEM medium, supplemented with 10% foetal calf serum, 2% sodium bicarbonate, 1 mM sodium pyruvate, 1% non-essential amino acids (e.g. obtained from Cambrex, # BE13-114E) and 2 mM glutamine, are cultivated. SK-MEL-28 cells are placed in 96-well flat bottomed dishes in a density of 7500 cells per well in supplemented MEM medium (see above) and incubated overnight in an incubator (at 37° C. and 5% $CO_2$). The active substances are added to the cells in different concentrations, so that a concentration range of 10 µM to 2.4 nM is covered. If necessary the initial concentration of 10 µM is changed to 50 µM or 2.5 µM and further dilution is carried out accordingly (up to 12.2 nM or 0.6 nM). After an incubation period of a further 2 h the cells are fixed with 4% formaldehyde and permeabilised with 0.1% triton X-100 in PBS. non-specific antibody binding is reduced by incubating with 5% skimmed milk powder dissolved in TBS-T. Phosphorylated ERK is detected with a murine monoclonal anti-diphosphorylated ERK1/2 antibody (from Sigma, #M8159). After washing steps using 0.1% Tween 20 in PBS the bound first antibody is detected by the second antibody (peroxidase coupled polyclonal rabbit anti mouse IgG from DAKO #P0161). After further washing steps the substrate (TMB Peroxidase Substrate Solution made by Bender MedSystems #BMS406) is added. The colour reaction is stopped after a few minutes with 1 M phosphoric acid. The staining is measured at 450 nm with a Spectra Max Plus reader made by Molecular Devices. $EC_{50}$ values are calculated using a software program (Graph Pad Prizm).

The $EC_{50}$ value of the phospho-ERK reduction of the example compounds determined using the above assay is generally less than 150 nM, for the most part less than 100 nM.

The substances of the present invention are B-RAF-kinase inhibitors. As can be demonstrated by DNA staining followed by FACS or Cellomics Array Scan analysis, the inhibition of proliferation achieved by means of the compounds according to the invention is brought about above all by preventing entry into the DNA synthesis phase. The treated cells arrest in the G1 phase of the cell cycle.

Accordingly, the compounds according to the invention are also tested on other tumour cells. For example these compounds are effective on the colon carcinoma line, e.g. Colo205, and may be used in this and other indications. This demonstrates the usefulness of the compounds according to the invention for the treatment of different types of tumours.

On the basis of their biological properties the compounds of general formula (1) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma, vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4, 3-alethine, 131-I-TM-601, 3CPA, 7-ethyl-10-hydroxycamptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992, BIBF 1120, bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-IOO, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alfa-2b, interleukin-2, ionafarnib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, MLN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, PEG-filgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, RAF-265, ramosetron, ranpimase, RDEA-119/BAY 869766, rebeccamycin analogues, revimid, RG-7167, rhizoxin, rhuMab, risedronate, rituximab, rofecoxib, Ro-31-7453, RO-5126766, RPR 109881A, rubidazon, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, xeloda, XELOX, XL-281, XL-518/R-7420, YM-511, YM-598, ZD-4190, ZD-6474, ZD-4054, ZD-0473, ZD-6126, ZD-9331, ZD1839, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (1) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (1) | 80 mg |
| | lactose | 55 mg |
| | corn starch | 190 mg |
| | microcrystalline cellulose | 35 mg |
| | polyvinylpyrrolidone | 15 mg |
| | sodiumcarboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (1) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of general formula (1)

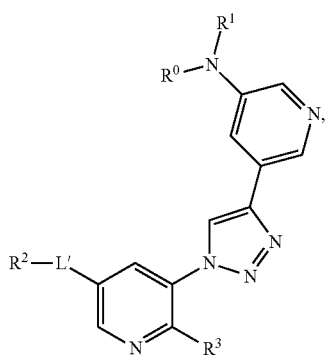

wherein
$R^0$ is selected from among hydrogen and $C_{1-6}$alkyl and
$R^1$ is hydrogen or a group optionally substituted by one or more identical or different $R^{b1}$ and/or $R^{c1}$, selected from among $C_{1-6}$alkyl, $C_{2-6}$alkenyl, $C_{1-6}$alkynyl, $C_{1-6}$haloalkyl, $C_{3-6}$cycloalkyl, $C_{4-6}$-cycloalkenyl and 3-11 membered heterocyclyl;
  each $R^{b1}$ is selected independently of one another from among —$OR^{c1}$, $SR^{c1}$, —$NR^{c1}R^{c1}$, halogen, —C(O)$R^{c1}$, —C(O)O$R^{c1}$, —C(O)N$R^{c1}R^{c1}$, —CN, —NHC(O)$R^{c1}$ and —NHC(O)O$R^{c1}$;
  each $R^{c1}$ independently of one another denotes hydrogen or a group selected from among $C_{1-6}$alkyl, $C_{2-6}$alkenyl, $C_{2-6}$alkinyl, $C_{3-6}$cycloalkyl, $C_{4-6}$cycloalkenyl, $C_{1-6}$alkyl-O—$C_{1-6}$alkyl, ($C_{1-4}$alkyl)HN—$C_{1-6}$alkyl, ($C_{1-4}$alkyl)$_2$N—$C_{1-6}$alkyl, $C_{1-6}$haloalkyl, 4-16 membered heterocyclylalkyl and 3-11 membered heterocyclyl, wherein heterocyclyl in the above-mentioned groups may optionally be substituted by one or more identical or different $C_{1-6}$alkyl;
or
  the group —$NR^0R^1$ together denotes a 3-11-membered, nitrogen-containing heterocyclyl, which is optionally substituted by one or more identical or different substituents $R^{a2}$ and/or $R^{b2}$;
    each $R^{a2}$ independently denotes a group optionally substituted by one or more identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$-cycloalkenyl and 3-11 membered heterocyclyl;
    each $R^{b2}$ is independently selected from among —$OR^{c2}$, —$SR^{c2}$, —$NR^{c2}R^{c2}$, halogen, —C(O)$R^{c2}$, —C(O)O$R^{c2}$, —C(O)N$R^{c2}R^{c2}$, —CN, —NHC(O)$R^{c2}$ and —NHC(O)O$R^{c2}$;
    each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-11 membered heterocyclyl, while this heterocyclyl may optionally be substituted by one or more identical or different substituents selected from among halogen, $C_{1-6}$alkyl and —C(O)—$C_{1-6}$alkyl;
$R^2$-$L^1$- is selected from among

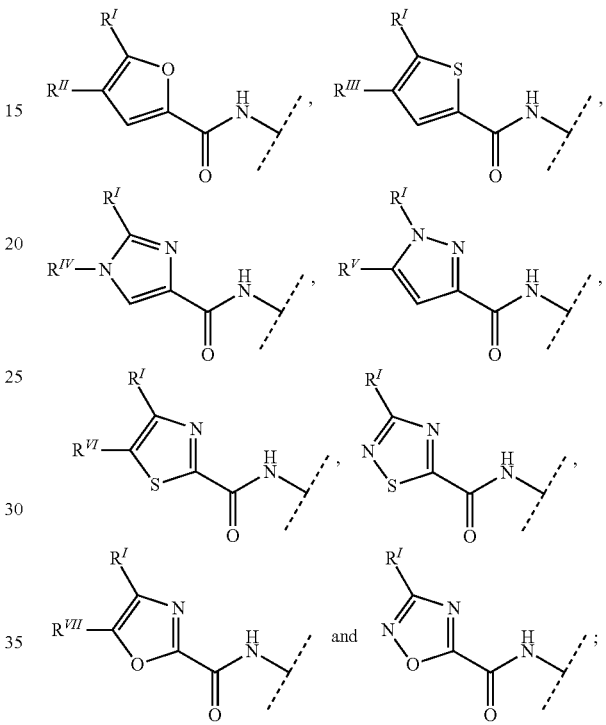

$R^I$ is selected from among tert-butyl, iso-propyl, cyclopropyl, —$CF_3$, —$CF_2(CH_3)$, —$CF(CH_3)_2$, —$CH_2CF_3$, —$CHF_2$, —$CH_2F$ and —$C(CH_3)_2CN$;
$R^{II}$, $R^{III}$ and $R^V$ are selected independently of one another from among hydrogen, methyl, ethyl, n-propyl, iso-propyl, cyclopropyl, $R^iR^{ii}N$—$CH_2$— and $R^{iii}O$—$CH_2$—;
$R^i$ is selected from among hydrogen and $C_{1-6}$alkyl;
$R^{ii}$ is selected from among $C_{1-6}$alkyl, ($C_{1-6}$alkyl)$_2$N—$C_{1-6}$alkyl-, ($C_{1-6}$alkyl)NH—$C_{1-6}$alkyl-, $C_{3-6}$cycloalkyl and 3-7 membered heterocyclyl, while this 3-7 membered heterocyclyl may optionally be substituted by $C_{1-6}$alkyl;
or
  the group —$NR^iR^{ii}$ together denotes a 3-7 membered, nitrogen-containing heterocyclyl, which may optionally be substituted by one or more identical or different $C_{1-6}$alkyl;
$R^{iii}$ is selected from among hydrogen, $C_{1-6}$alkyl, $C_{3-6}$cycloalkyl and $C_{1-6}$haloalkyl;
$R^{IV}$ is selected from among hydrogen, methyl, ethyl and n-propyl;
$R^{VI}$ and $R^{VII}$ are selected independently of one another from among hydrogen, methyl, ethyl, n-propyl, iso-propyl and cyclopropyl;
$R^3$ is selected from among $C_{1-4}$alkyl, $C_{1-4}$haloalkyl, $C_{1-4}$alkyl-O—, $C_{1-4}$haloalkyl-O—, —$NH_2$, and —NH($C_{1-4}$alkyl);

or a tautomer, racemate, enantiomer, diastereomer or mixtures thereof or a salt thereof.

2. The compound according to claim 1, wherein $R^3$ denotes methyl.

3. The compound according to claim 1, wherein $R^0$ is selected from among hydrogen and methyl and $R^1$ is hydrogen or a group optionally substituted by one or more, identical or different $R^{b1}$ and/or $R^{c1}$, selected from among methyl, ethyl, n-propyl, iso-propyl, tert-butyl, cyclopropyl, cyclobutyl, cyclopentyl, cyclohexyl and 5-7 membered heterocyclyl;

each $R^{b1}$ is independently selected from among —$OR^{c1}$, —$NR^{c1}R^{c1}$ halogen and —$C(O)OR^{c1}$;

each $R^{c1}$ independently of one another denotes hydrogen or a group selected from among methyl, ethyl, iso-propyl and 5-7 membered heterocyclyl, wherein this 5-7 membered heterocyclyl may optionally be substituted by one or more identical or different substituents, selected from among methyl, ethyl or iso-propyl.

4. The compound according to claim 1, wherein the group —$NR^0R^1$ together denotes a 3-11 membered, nitrogen-containing heterocyclyl which is optionally substituted by one or more identical or different substituents $R^{a2}$ and/or $R^{b2}$;

each $R^{2a}$ independently of one another denotes a group optionally substituted by one or more identical or different $R^{b2}$ and/or $R_{c2}$, selected from among iso-propyl, methyl, ethyl, tert-butyl, n-propyl, n-butyl, iso-butyl, 3-pentyl, allyl, cyclopropyl, cyclobutyl, cyclopentyl, cyclohexyl and 3-11 membered heterocyclyl;

each $R^{b2}$ is selected independently of one another from among —$OR^{c2}$, —$NR^{c2}R^{c2}$, halogen, —$C(O)OR^{c2}$, —$C(O)NR^{c2}R^{c2}$ and —CN;

each $R^{c2}$ independently of one another denotes hydrogen or a group selected from among methyl, ethyl, iso-propyl, tert-butyl, cyclopropyl, cyclobutyl, cyclopentyl, cyclohexyl and 3-11 membered heterocyclyl.

5. The compound according to claim 1, wherein $R^2$-L'- is selected from among

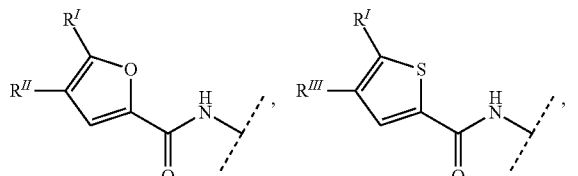

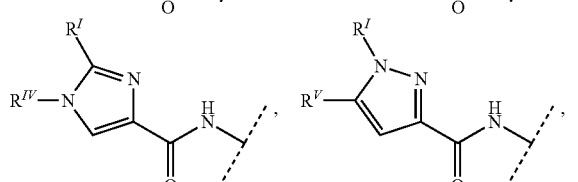

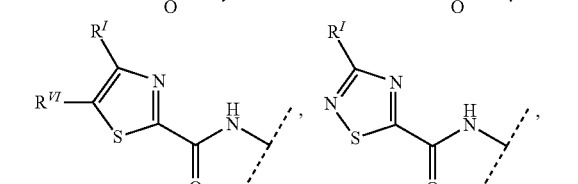

-continued

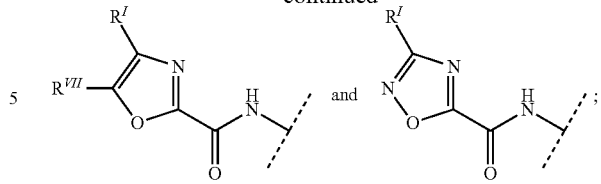

$R^I$ is selected from among tert-butyl and iso-.

6. The compound according to claim 5, wherein $R^2$-L'- denotes the group

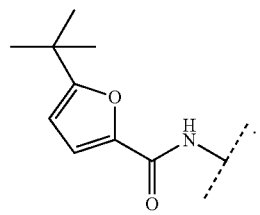

7. The compound according to claim 5, wherein $R^2$-L'- denotes the group

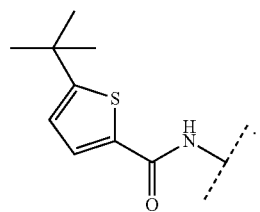

8. The compound according to claim 5, wherein $R^2$-L'- denotes the group

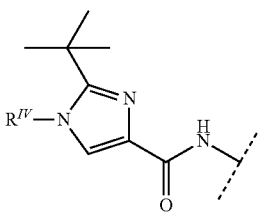

and $R^{IV}$ denotes methyl or ethyl.

9. The compound according to claim 5, wherein $R^2$-L'- denotes the group

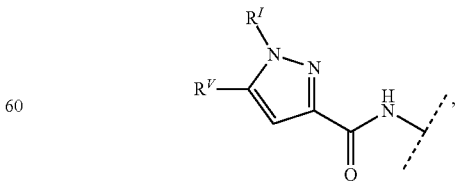

$R^I$ is selected from among iso-propyl and tert-butyl and $R^V$ is selected from among methyl, ethyl, n-propyl, iso-propyl and cyclopropyl.

10. The compound according to claim 5, wherein R²-L¹- is selected from among

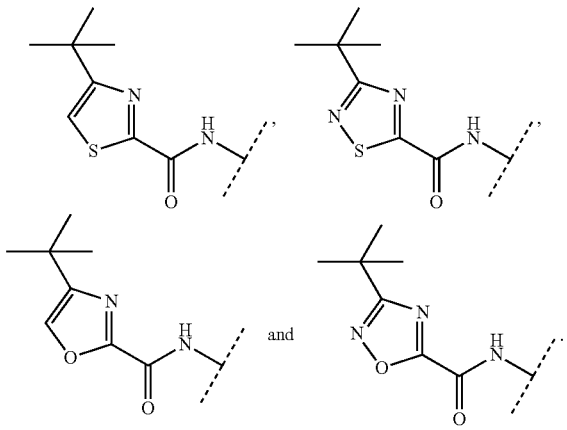

and

11. A compound selected from the group consisting of:

I-1  5-tert.-butyl-furan-2-carboxylic acid (5-{4-[5-(4-isopropyl-piperazin-1-yl)-pyridin-3-yl]-[1,2,3]triazol-1-yl}-6-methyl-pyridin-3-yl)-amide;
I-2  5-tert.-butyl-furan-2-carboxylic acid (6-methyl-5-{4-[5-(4-methyl-piperazin-1-yl)-pyridin-3-yl]-[1,2,3]triazol-1-yl}-pyridin-3-yl)-amide;
I-3  5-tert.-butyl-furan-2-carboxylic acid (5-{4-[5-(4-ethyl-piperazin-1-yl)-pyridin-3-yl]-[1,2,3]triazol-1-yl}-6-methyl-pyridin-3-yl)-amide;
I-4  5-tert.-butyl-furan-2-carboxylic acid (5-{4-[5-(4-tert.-butyl-piperazin-1-yl)-pyridin-3-yl]-[1,2,3]triazol-1-yl}-6-methyl-pyridin-3-yl)-amide;
I-5  5-tert.-butyl-furan-2-carboxylic acid (5-{4-[5-(4-cyclopropylmethyl-piperazin-1-yl)-pyridin-3-yl]-[1,2,3]triazol-1-yl}-6-methyl-pyridin-3-yl)-amide;
I-6  5-tert.-butyl-furan-2-carboxylic acid [5-(4-{5-[4-(3-methoxy-propyl)-piperazin-1-yl]-pyridin-3-yl}-[1,2,3]triazol-1-yl)-6-methyl-pyridin-3-yl]-amide;
I-7  5-tert.-butyl-furan-2-carboxylic acid [5-(4-{5-[4-(2-ethoxy-ethyl)-piperazin-1-yl]-pyridin-3-yl}-[1,2,3]triazol-1-yl)-6-methyl-pyridin-3-yl]-amide;
I-8  5-tert.-butyl-thiophene-2-carboxylic acid [5-(4-{5-[4-(2-ethoxy-ethyl)-piperazin-1-yl]-pyridin-3-yl}-[1,2,3]triazol-1-yl)-6-methyl-pyridin-3-yl]-amide;
I-9  5-tert.-butyl-thiophene-2-carboxylic acid [5-(4-{5-[4-(3-methoxy-propyl)-piperazin-1,2,3]triazol-1-yl}-6-methyl-pyridin-3-yl]-amide;
I-10  5-tert.-butyl-thiophene-2-carboxylic acid (5-{(4-[5-(4-cyclopropylmethyl-piperazin-1-yl)-pyridin-3-yl]-[1,2,3]triazol-1-yl}-6-methyl-pyridin-3-yl)-amide;
I-11  5-tert.-butyl-thiophene-2-carboxylic acid (5-{4-[5-(4-tert.-butyl-piperazin-1-yl)-pyridin-3-yl]-[1,2,3]triazol-1-yl}-6-methyl-pyridin-3-yl)-amide;
I-12  5-tert.-butyl-thiophene-2-carboxylic acid (5-{4-[5-(4-ethyl-piperazin-1-yl)-pyridin-3-yl]-[1,2,3]triazol-1-yl}-6-methyl-pyridin-3-yl)-amide;
I-13  5-tert.-butyl-thiophene-2-carboxylic acid (5-{4-[5-(4-isopropyl-piperazin-1-yl)-pyridin-3-yl]-[1,2,3]triazol-1-yl}-6-methyl-pyridin-3-yl)-amide;
I-14  5-tert.-butyl-thiophene-2-carboxylic acid (6-methyl-5-{4-[5-(4-methyl-piperazin-1-yl)-pyridin-3-yl]-[1,2,3]triazol-1-yl}-pyridin-3-yl)-amide;
I-15  1-tert.-butyl-5-methyl-1H-pyrazol-3-carboxylic acid (5-{4-[5-(4-cyclopropyl-piperazin-1-yl)-pyridin-3-yl]-[1,2,3]triazol-1-yl}-6-methyl-pyridin-3-yl)-amide;
I-16  1-tert.-butyl-5-methyl-1H-pyrazole-3-carboxylic acid (6-methyl-5-{4-[5-(4-methyl-[1,4]diazepan-1-yl)-pyridin-3-yl]-[1,2,3]triazol-1-yl}-pyridin-3-yl)-amide;
I-17  1-tert.-butyl-5-methyl-1H-pyrazol-3-carboxylic acid (6-methyl-5-{4-[5-(4-propyl-piperazin-1-yl)-pyridin-3-yl]-[1,2,3]triazol-1-yl}-pyridin-3-yl)-amide;
I-18  1-tert.-butyl-5-methyl-1H-pyrazol-3-carboxylic acid (6-methyl-5-{4-[5-(4-methyl-piperazin-1-yl)-pyridin-3-yl]-[1,2,3]triazol-1-yl}-pyridin-3-yl)-amide;
I-19  1-tert.-butyl-5-methyl-1H-pyrazol-3-carboxylic acid (5-{4-[5-(4-isopropyl-piperazin-1-yl)-pyridin-3-yl]-[1,2,3]triazol-1-yl}-6-methyl-pyridin-3-yl)-amide;
I-20  1-tert.-butyl-5-methyl-1H-pyrazol-3-carboxylic acid (5-{4-[5-(4-ethyl-piperazin-1-yl)-pyridin-3-yl]-[1,2,3]triazol-1-yl}-6-methyl-pyridin-3-yl)-amide;
I-21  1-tert.-butyl-5-methyl-1H-pyrazol-3-carboxylic acid (5-{4-[5-(4-tert.-butyl-piperazin-1-yl)-pyridin-3-yl]-[1,2,3]triazol-1-yl}-6-methyl-pyridin-3-yl)-amide;
I-22  1-tert.-butyl-5-methyl-1H-pyrazol-3-carboxylic acid (5-{4-[5-(4-cyclopropylmethyl-piperazin-1-yl)-pyridin-3-yl]-[1,2,3]triazol-1-yl}-6-methyl-pyridin-3-yl)-amide;
I-23  1-tert.-butyl-5-methyl-1H-pyrazol-3-carboxylic acid [5-(4-{5-[4-(3-methoxy-propyl)-piperazin-1-yl]-pyridin-3-yl}-[1,2,3]triazol-1-yl)-6-methyl-pyridin-3-yl]-amide;
I-24  1-tert.-butyl-5-methyl-1H-pyrazol-3-carboxylic acid [5-(4-{5-[4-(2-ethoxy-ethyl)-piperazin-1-yl]-pyridin-3-yl}-[1,2,3]triazol-1-yl)-6-methyl-pyridin-3-yl]-amide;
I-25  1-tert.-butyl-5-methyl-1H-pyrazol-3-carboxylic acid [5-(4-{5-[4-(2-isopropoxy-ethyl)-piperazin-1-yl]-pyridin-3-yl}-[1,2,3]triazol-1-yl)-6-methyl-pyridin-3-yl]-amide;
I-26  1-tert.-butyl-5-ethyl-1H-pyrazol-3-carboxylic acid (5-{4-[5-(4-cyclopropyl-piperazin-1-yl)-pyridin-3-yl]-[1,2,3]triazol-1-yl}-6-methyl-pyridin-3-yl)-amide;
I-27  1-tert.-butyl-5-ethyl-1H-pyrazol-3-carboxylic acid (5-{4-[5-(4-isopropyl-piperazin-1-yl)-pyridin-3-yl]-[1,2,3]triazol-1-yl}-6-methyl-pyridin-3-yl)-amide;
I-28  1-tert.-butyl-5-ethyl-1H-pyrazol-3-carboxylic acid (6-methyl-5-{4-[5-(4-propyl-piperazin-1-yl)-pyridin-3-yl]-[1,2,3]triazol-1-yl}-pyridin-3-yl)-amide;
I-29  1-tert.-butyl-5-methyl-1H-pyrazol-3-carboxylic acid (5-{4-[5-(4-isopropyl-[1,4]diazepan-1-yl)-pyridin-3-yl]-[1,2,3]triazol-1-yl}-6-methyl-pyridin-3-yl)-amide;
I-30  1-tert.-butyl-5-ethyl-1H-pyrazol-3-carboxylic acid (6-methyl-5-{4-[5-(4-methyl-piperazin-1-yl)-pyridin-3-yl]-[1,2,3]triazol-1-yl}-pyridin-3-yl)-amide;
I-31  1-tert.-butyl-5-ethyl-1H-pyrazol-3-carboxylic acid (5-{4-[5-(4-ethyl-piperazin-1-yl)-pyridin-3-yl]-[1,2,3]triazol-1-yl}-6-methyl-pyridin-3-yl)-amide;
I-32  1-tert.-butyl-5-propyl-1H-pyrazol-3-carboxylic acid (5-{4-[5-(4-cyclopropyl-piperazin-1-yl)-pyridin-3-yl]-[1,2,3]triazol-1-yl}-6-methyl-pyridin-3-yl)-amide;
I-33  1-tert.-butyl-5-propyl-1H-pyrazol-3-carboxylic acid (5-{4-[5-(4-ethyl-piperazin-1-yl)-pyridin-3-yl]-[1,2,3]triazol-1-yl}-6-methyl-pyridin-3-yl)-amide;
I-34  1-tert.-butyl-5-propyl-1H-pyrazol-3-carboxylic acid (5-{4-[5-(4-isopropyl-piperazin-1-yl)-pyridin-3-yl]-[1,2,3]triazol-1-yl}-6-methyl-pyridin-3-yl)-amide;
I-35  1-tert.-butyl-5-propyl-1H-pyrazol-3-carboxylic acid (6-methyl-5-{4-[5-(4-propyl-piperazin-1-yl)-pyridin-3-yl]-[1,2,3]triazol-1-yl}-pyridin-3-yl)-amide;
I-36  1-tert.-butyl-5-propyl-1H-pyrazol-3-carboxylic acid (6-methyl-5-{4-[5-(4-methyl-piperazin-1-yl)-pyridin-3-yl]-[1,2,3]triazol-1-yl}-pyridin-3-yl)-amide;

I-37 1-tert.-butyl-5-isopropyl-1H-pyrazol-3-carboxylic acid (6-methyl-5-{1-[5-(4-methyl-piperazin-1-yl)-pyridin-3-yl]-[1,2,3]triazol-1-yl}-pyridin-3-yl)-amide;

I-38 1-tert.-butyl-5-isopropyl-1H-pyrazol-3-carboxylic acid (5-{4-[5-(4-isopropyl-piperazin-1-yl)-pyridin-3-yl]-[1,2,3]triazol-1-yl}-6-methyl-pyridin-3-yl)-amide;

I-39 1-tert.-butyl-5-isopropyl-1H-pyrazol-3-carboxylic acid (5-{4-[5-(4-ethyl-piperazin-1-yl)-pyridin-3-yl]-[1,2,3]triazol-1-yl}-6-methyl-pyridin-3-yl)-amide;

I-40 1-tert.-butyl-5-isopropyl-1H-pyrazol-3-carboxylic acid (6-methyl-5-{4-[5-(4-propyl-piperazin-1-yl)-pyridin-3-yl]-[1,2,3]triazol-1-yl}-pyridin-3-yl)-amide;

I-41 1-tert.-butyl-5-cyclopropyl-1H-pyrazol-3-carboxylic acid (6-methyl-5-{4-[5-(4-methyl-piperazin-1-yl)-pyridin-3-yl]-[1,2,3]triazol-1-yl}-pyridin-3-yl)-amide;

I-42 1-tert.-butyl-5-cyclopropyl-1H-pyrazol-3-carboxylic acid (5-{4-[5-(4-isopropyl-piperazin-1-yl)-pyridin-3-yl]-[1,2,3]triazol-1-yl}-6-methyl-pyridin-3-yl)-amide;

I-43 1-tert.-butyl-5-cyclopropyl-1H-pyrazol-3-carboxylic acid (5-{4-[5-(4-ethyl-piperazin-1-yl)-pyridin-3-yl]-[1,2,3]triazol-1-yl}-6-methyl-pyridin-3-yl)-amide;

I-44 1-tert.-butyl-5-cyclopropyl-1H-pyrazol-3-carboxylic acid (6-methyl-5-{4-[5-(4-propyl-piperazin-1-yl)-pyridin-3-yl]-[1,2,3]triazol-1-yl}-pyridin-3-yl)-amide;

I-45 1-isopropyl-5-methyl-1H-pyrazol-3-carboxylic acid (6-methyl-5-{4-[5-(4-methyl-piperazin-1-yl)-pyridin-3-yl]-[1,2,3]triazol-1-yl}-pyridin-3-yl)-amide;

I-46 1-isopropyl-5-methyl-1H-pyrazol-3-carboxylic acid (5-{4-[5-(4-ethyl-piperazin-1-yl)-pyridin-3-yl]-[1,2,3]triazol-1-yl}-6-methyl-pyridin-3-yl)-amide;

I-47 1-isopropyl-5-methyl-1H-pyrazol-3-carboxylic acid (5-{4-[5-(4-isopropyl-piperazin-1-yl)-pyridin-3-yl]-[1,2,3]triazol-1-yl}-6-methyl-pyridin-3-yl)-amide;

I-48 1-isopropyl-5-methyl-1H-pyrazol-3-carboxylic acid (6-methyl-5-{4-[5-(4-propyl-piperazin-1-yl)-pyridin-3-yl]-[1,2,3]triazol-1-yl}-pyridin-3-yl)-amide;

I-49 1-isopropyl-5-methyl-1H-pyrazol-3-carboxylic acid (5-{4-[5-(4-cyclopropyl-piperazin-1-yl)-pyridin-3-yl]-[1,2,3]triazol-1-yl}-6-methyl-pyridin-3-yl)-amide and I-50 1-isopropyl-5-methyl-1H-pyrazol-3-carboxylic acid (6-methyl-5-{4-[5-(4-methyl-[1,4]diazepan-1-yl)-pyridin-3-yl]-[1,2,3]triazol-1-yl}-pyridin-3-yl)-amide;

or a the pharmaceutically acceptable salt thereof.

12. A Pharmaceutically acceptable salt of a compound according to claim 1.

13. A method of treating cancer, comprising administering to a patient a therapeutically effective amount of a compound according to claim 1 or a pharmaceutically acceptable salt thereof.

14. A pharmaceutical composition comprising a therapeutically effective amount of a compound according to claim 1 or a pharmaceutically acceptable salt thereof optionally in combination with conventional excipients and/or carriers.

15. The pharmaceutical composition according to claim 14 and at least one other further cytostatic or cytotoxic active substance different from formula (1).

* * * * *